United States Patent
Weaver et al.

(10) Patent No.: US 9,567,404 B2
(45) Date of Patent: *Feb. 14, 2017

(54) ANTI-VASA ANTIBODIES, AND METHODS OF PRODUCTION AND USE THEREOF

(71) Applicant: OvaScience, Inc., Cambride, MA (US)

(72) Inventors: David T. Weaver, Newton, MA (US); Bo Zhang, Lynnfield, MA (US)

(73) Assignee: OvaScience, Inc., Waltham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/203,040

(22) Filed: Jul. 6, 2016

(65) Prior Publication Data

US 2016/0311929 A1 Oct. 27, 2016

Related U.S. Application Data

(63) Continuation of application No. 14/856,380, filed on Sep. 16, 2015, now Pat. No. 9,403,913.

(60) Provisional application No. 62/089,054, filed on Dec. 8, 2014, provisional application No. 62/051,130, filed on Sep. 16, 2014.

(51) Int. Cl.
*C12N 15/85* (2006.01)
*C07K 16/40* (2006.01)
*G01N 33/573* (2006.01)

(52) U.S. Cl.
CPC ............ *C07K 16/40* (2013.01); *G01N 33/573* (2013.01); *C07K 2317/14* (2013.01); *C07K 2317/51* (2013.01); *C07K 2317/515* (2013.01); *C07K 2317/52* (2013.01); *C07K 2317/56* (2013.01); *C07K 2317/565* (2013.01); *C07K 2317/622* (2013.01); *G01N 2333/914* (2013.01)

(58) Field of Classification Search
None
See application file for complete search history.

(56) References Cited

U.S. PATENT DOCUMENTS

| | | |
|---|---|---|
| 6,875,854 B1 | 4/2005 | Castrillon |
| 7,955,846 B2 | 6/2011 | Tilly et al. |
| 8,642,329 B2 | 2/2014 | Tilly et al. |
| 8,647,869 B2 | 2/2014 | Tilly et al. |
| 8,652,840 B2 | 2/2014 | Tilly et al. |
| 9,403,913 B2 * | 8/2016 | Weaver .................. C07K 16/40 |
| 2011/0244485 A1 | 10/2011 | Yoshizaki et al. |

FOREIGN PATENT DOCUMENTS

| | | |
|---|---|---|
| WO | WO-96/39518 A1 | 12/1996 |
| WO | WO-01/36445 A1 | 5/2001 |
| WO | WO-2005/121321 A2 | 12/2005 |
| WO | WO-2006/006693 A1 | 1/2006 |
| WO | WO-2006/067913 A1 | 6/2006 |
| WO | WO-2010074192 A1 | 7/2010 |
| WO | WO-2011/016238 A1 | 2/2011 |
| WO | WO-2012/142500 A2 | 10/2012 |
| WO | WO-2014/106235 A1 | 7/2014 |

OTHER PUBLICATIONS

Kunert et al., Appl Microbiol Biotechnol. Apr. 2016;100(8):3451-61. doi: 10.1007/s00253-016-7388-9. Epub Mar. 3, 2016.*
Kipriyanov et al., Mol Biotechnol. Sep. 1999;12(2):173-201.*
Alamyar, E., et al., "IMGT® tools for the nucleotide analysis of immunoglobulin (IG) and T cell receptor (TR) V-(D)-J repertoires, polymorphisms, and IG mutations: IMGT/V-QUEST and IMGT/HighV-QUEST for NGS," Methods Mol. Biol., vol. 882, pp. 569-604 (2012).
Castrillon, D. H., et al., "The human VASA gene is specifically expressed in the germ cell lineage," PNAS, vol. 97, No. 17, pp. 9585-9590 (Aug. 15, 2000).
Fundamental Immunology, Raven Press, 1993, William E. Paul, editor, p. 242.
Gavis, E. R., et al., "A conserved 90 nucleotide element mediates translational repression of nanos RNA," Development, vol. 122, pp. 2791-2800 (1996).
Ginsburg, M., et al., "Primordial germ cells in the mouse embryo during gastrulation," Development, vol. 110, pp. 521-528 (1990).
International Search Report and Written Opinion issued by the U.S. Patent and Trademark Office as International Searching Authority for International Application No. PCT/US2015/050449 dated Apr. 14, 2016 (12 pages).
Janeway et al., Immunobiology, 3rd edition, 1997, Garland Publishing Inc., pp. 3:1-3:11.
Johnson, J., et al., "Germline stem cells and follicular renewal in the postnatal mammalian ovary," Nature, vol. 428, No. 6979, pp. 145-150 (Mar. 11, 2004).
Lasko, P. F. and Ashburner, M., "The product of the *Drosophila* gene Vasa is very similar to eukaryotic initiation factor-4A," Nature vol. 335, No. 6191, pp. 611-617 (Oct. 13, 1988).
LeFranc, M. P., "IMGT® databases, web resources and tools for immunoglobulin and T cell receptor sequence analysis, http://imgt.cines.fr," Leukemia, vol. 17, pp. 260-266 (2003).
Liang, L., et al., "Localization of vasa protein to the *Drosophila* pole plasm is independent of its RNA-binding and helicase activities," Development, vol. 120, No. 5, pp. 1201-1211 (Jun. 1994).

(Continued)

*Primary Examiner* — Michael Szperka
(74) *Attorney, Agent, or Firm* — Wilmer Cutler Pickering Hale and Dorr LLP

(57) ABSTRACT

Anti-VASA antibodies (mAbs), particularly humanized mAbs that specifically bind to VASA with high affinity, are disclosed. The amino acid sequences of the CDRs of the light chains and the heavy chains, as well as consensus sequences for these CDRs, of these anti-VASA mAbs are provided. The disclosure also provides nucleic acid molecules encoding the anti-VASA mAbs, expression vectors, host cells, methods for making the anti-VASA mAbs, and methods for expressing the anti-VASA mAbs. Finally, methods of using the anti-VASA mAbs to isolate and/or purify cells expressing VASA are disclosed.

6 Claims, 15 Drawing Sheets

(56) References Cited

OTHER PUBLICATIONS

Medrano, J. V., et al., "Divergent RNA-Binding Proteins, DAZL and VASA, Induce Meiotic Progression in Human Germ Cells Derived In Vitro," Stem Cells, vol. 30, pp. 441-451 (Dec. 12, 2011).
Noce, T., et al., "Vasa Homolog Genes in Mammalian Germ Cell Development," Cell Structure and Function, vol. 26, pp. 131-136 (2001).
Portolano et al., J Immunol. Feb. 1, 1993; 150(3); 880-7.
Renault, Andrew D., "Vasa is expressed in somatic cells of the embryonic gonad in a sex-specific manner in *Drosophila melanogaster*," Biology Open, vol. 2012, pp. 1-6 (Aug. 20, 2012).
Rudikoff et al., Proc Natl Acad Sci USA. Mar. 1982; 79(6): 1979-83.
Telfer, E. E. and Albertini, D. F., "The quest for human ovarian stem cells," Nature Medicine, vol. 18, No. 3, pp. 353-354 (2012).
Tilly, J. L. and Telfer, E. E., "Purification of germline stem cells from adult mammalian ovaries: a step closer towards control of the female biological clock?," Mol. Hum. Repro., vol. 15, No. 7, pp. 393-398 (Jul. 2009).
Verma, R., et al., "Antibody engineering: comparison of bacterial, yeast, insect and mammalian expression systems," J. Immunol. Methods, vol. 216, No. 1-2, pp. 165-181 (Jul. 1, 1998).
White, Y. A. R., et al., "Oocyte formation by mitotically-active germ cells purified from ovaries of reproductive age women," Nature Medicine, vol. 18, No. 3 pp. 413-421 (Mar. 2012).
Zou, K., et al., "Production of offspring from a germline stem cell line derived from neonatal ovaries," Nature Cell Biology, vol. 11, 20 pages (2009).

\* cited by examiner

Human VASA Amino Acid Sequence (Accession: NP_077726; SEQ ID NO: 1))

```
  1   mgdedweaei nphmssyvpi fekdrysgen qdnfnrtpas ssemddgpsr rdhfmksgfa
 61   sgrnfgnrda gecnkrdnts tmggfgvgks fgnrgfsnsr fedgdssgfw ressndcedn
121   ptrnrgfskr ggyrdgnnse asgpyrrggr gsfrgcrggf glgspnndld pdecmqrtgg
181   lfgsrrpvls gtgngdtsqs rsgsgsergg ykglneevit gsgknswkse aeggessdtq
241   gpkvtyippp ppededsifa hyqtginfdk ydtilvevsg hdappailtf eeanlcqtln
301   nniakagytk ltpvqkysip iilagrdlma caqtgsgkta afllpilahm mhdgitasrf
361   kelqepecii vaptrelvnq iylearkfsf gtcvravviy ggtqlghsir qivqgcnilc
421   atpgrlmdii gkekiglkqi kylvldeadr mldmgfgpem kkliscpgmp skeqrqtlmf
481   satfpeeiqr laaeflksny lfvavgqvgg acrdvqqtvl qvgqfskrek lveilrnigd
541   ertmvfvetk kkadfiatfl cqekisttsi hgdreqrere qalgdfrfgk cpvlvatsva
601   argldienvq hvinfdlpst ideyvhrigr tgrcgntgra isffdlescn hlaqplvkvl
661   tdaqqdvpaw leeiafstyi pgfsqstrgn vfasvdtrkg kstlntagfs ssqapnpvdd
721   eswd
```

FIG. 1

Mouse VASA Homolog Amino Acid Sequence (Accession: NP_001139357, SEQ ID NO: 2))

```
  1   mgdedweaei lkphvssyvp vfekdkyssg angdtfnrts assemedgps grddfmrsgf
 61   psgrslgsrd igesskkent sttggfgrgk gfgnrgflnn kfeegdssgf wkesnndced
121   nqtrsrgfsk rggcqdgnds easgpfrrgg rgsfrgcrgg fglgrpnses dqdqgtqrgg
181   glfgsrkpaa sdsgngdtyq srsgsgrggy kglneevvtg sgknswkset eggessdsqg
241   pkvtyipppp pededsifah yqtginfdky dtilvevsgh dappailtfe eanlcqtlnn
301   niakagytkl tpvqkysipi vlagrdlmac aqtgsgktaa fllpilahmm rdgitasrfk
361   elqepeciiv aptrelinqi ylearkfsfg tcvravviyg gtqfghsvrq ivqgcnilca
421   tpgrlmdiig kekiglkqvk ylvldeadrm ldmgfgpemk kliscpgmps keqrqtllfs
481   atfpeeiqrl agdflkssyl fvavgqvgga crdvqqtilq vgqyskrekl veilrnigde
541   rtmvfvetkk kadfiatflc qekisttsih gdreqrereq algdfrcgkc pvlvatsvaa
601   rgldienvqh vinfdlpsti deyvhrigrt grcgntgrai sffdtdsdnh laqplvkvls
661   daqqdvpawl eeiafstyvp psfssstrgg avfasvdtrk nyqgkhtlnt agisssqapn
721   pvddeswd
```

FIG. 2

Human: ...nvfasvdtrk gkstlntagfsssqapnpvddeswd
(SEQ ID NO: 1 residues 690-724)
Mouse: ...avfasvdtrknyqgkhtlntagisssqapnpvddeswd
(SEQ ID NO: 2 residues 691-728)
FIG. 3
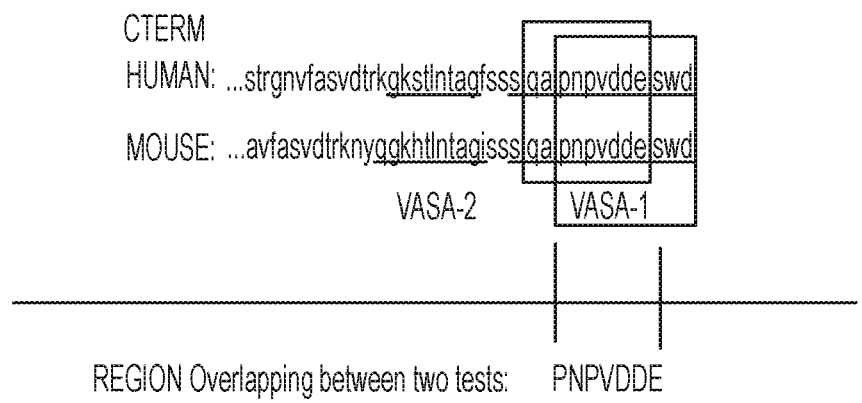
FIG. 4A
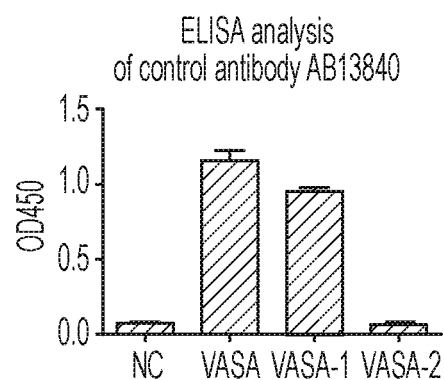
FIG. 4B VASA peptide sequence: GKSTLNTAGFSSSQAPNPVDDESWD
VASA-1 peptide sequence: SQAPNPVDDE
VASA-2 peptide sequence: GKSTLNTAGF Light Chain Variable Region Sequence Alignments

| SEQ ID NO. | CLONE NAME | | CDR1 | CDR2 | |
|---|---|---|---|---|---|
| 3 | 1N23VL5-5 | FTVMTQTPLSLPVSLGDQASISCR-SSQSLVHSNGNTYLHWYLQKPGQSPKLLIYKVSNRF | 60 |
| 4 | 1N23VL5-8_0816 | STVMTQTPLSLPVSLGDQASISCR-SSQSLVHSNGNTYLHWYLQKPGQSPKLLIYKVSNRF | 60 |
| 5 | 1N23VL1-8 | LVLMTQTPLSLPVSLGDQASISCR-SSQSLVHSNGNTYLHWYLQKPGQSPKLLIYKVSNRF | 60 |
| 6 | 1N23VL1-2_0820 | SVLMTQTPLSLPVSLGDQASISCR-SSQSLVHSNGNTYLHWYLQKPGQSPKLLIYKVSNRF | 60 |
| 7 | 1N23VL1-4_0820 | YVLMTQTPLSLPVSLGDQASISCR-SSQSLVHSNGNTYLHWYLQKPGQSPKLLIYKVSNRF | 60 |
| 8 | 1K23VL2-5 | QVLMTQAPLSLPVSLGDQASISCR-SSQSLVHSNGNTYLHWYLQKPGQSPKLLIYKVSNRF | 60 |
| 9 | 1N23VL1-2 | RFQVSQTPLSLPVSLGDQASISCR-SSQSLVHSNGNTYLHWYLQKPGQSPKLLIYKVSNRF | 60 |
| 10 | 1K23VL2-6 | VFVMTQAPLSLPVSLGDQASISCR-SSQSLVHSNGNTYLHWYLQKPGQSPKLLIYKVSNRF | 60 |
| 11 | 1K23VL2-8_0822 | LTVMTQAPLSLPVSLGDQASTSCR-SSQSLVHSNGNTYLHWYLQKPGQSPKLLIYKVSNRF | 60 |
| 12 | 1K23VL2-3_0829 | STVMTQAPLSLPVSLGDQASISCR-SSQNIVHSNGNTYLHWYLQKPGQSPKLLIYKVSNRF | 60 |
| 13 | 2K4VL1-3_0820 | SVLMTQTPLSLPVSLGDQASISSR-SSQNIVHSNGNTYLHWYLQKPGQSPKLLIYKISNRF | 60 |
| 14 | 2K4VL1-4 | LVLMTQTPLSLPVSLGDQASISCR-SSQNIVHSNGNTYLEWYLQKPGQSPKLLIYKVSNRF | 60 |
| 15 | 2K4VL1-1 | LVLMTQTPLSLPVSLGDQASISCR-SSQNIVHSNGNTYLEWYLQKPGQSPKLLIYKVSNRF | 60 |
| 16 | 2K4VL1-6_0820 | LVLMTQTPLSLPVSLGDQASISCR-SSQNIVHSNGNTYLEWYLQKPGQSPKLLIYKVSNRF | 60 |
| 17 | 1C9VL2-4 | LTVMTQAAPSVPVTPGESVSISCR-STKSLLHSNGNTYLSWFLQRPGQSPQLLIYRMSNLA | 60 |
| 18 | 1C9VL2-6 | YTVMTQAAPSVPVTPGESVSISCR-STKSLLHSNGNTYLSWFLQRPGQSPQLLIYRMSNLA | 60 |
| 19 | 1C9VL2-3_0816 | SGLMTQAAPSVPVTPGESVSISCR-STKSLLHSNGNTYLSWFLQRPGQSPQLLIYRMSNLA | 60 |
| 20 | 2K4VL2-5_0816 | PGLMTQAAPSVPVTPGESVSISCR-SSKSLLHSNGNTYLYWFLQRPGQSPQLLIYRMSNLA | 60 |
| 21 | 2K4VL2-4 | SLVMTQAAPSVPVTPGESVSISCR-SSKSLLHSNGNTYLYWFLQRPGQSPQLLIYRMSNLA | 60 |
| 22 | 2K4VL2-6_0816 | STVMTQAAPSVPVTPGESVSISCR-SSKSLLHSNGNTYLYWFLQRPGQSPQLLIYRMSNLA | 60 |
| 23 | 1J20VL5-2_0907 | DIVMTQSAPSVPVTPGESVSISCR-SSKSLLHSNGNTYLYWFLQRPGQSPQLLIYRMSNLA | 60 |

FIG. 9A

| | | |
|---|---|---|
| 24 | 1J20VL5-6_0907 | DIVMTQSAPSVPVTPGESVSISCR-SSKSLLHSNGNTYLYWFLQRPGQSPQLLIYRMSNLA 60 |
| 25 | 1J20VL4-3_0907 | DIVLTQSAPSVPVTPGESVSISCR-SSKSLLHSNGNTYLYWFLQRPGQSPQLLIYRMSNLA 60 |
| 26 | 1L20VL5-0912_0917 | DGVMTQSAPSVPVTPGESVSISCR-SSKSLLHSNGNTYLYWFLQRPGQSPQLLIYRMSNLA 60 |
| 27 | 1K3VL2-5 | LIVMTQAAPSVPVTPGESVSISCR-SSKSLLHSNGNTYLYWFLQRPGQSPQLLIYRMSNLA 60 |
| 28 | 1K3VL2-3 | LIVMTQAAPSVPVTPGESVSISCR-SSKSLLHSNGNTYLYWFLQRPGQSPQLLIYRMSNLA 60 |
| 29 | 1K3VL2-4 | SIVMTQAAPSVPVTPGESVSISCR-SSKSLLHSNGNTYLYWFLQRPGQSPQLLIYRMSNLA 60 |
| 30 | 2K4VL2-5 | VFVMTQAAPSVPVTPGESVSISCR-SSKSLLHSNGNTYLYWFLQRPGQSPQLLIYRMSNLA 60 |
| 31 | 1L5VL2-4 | DIVMTQAAPSVPVTPGESVSISCR-SSKSLLHSNGNTYLYWFLQRPGQSPQLLIYRMSNLA 60 |
| 32 | 1L5VL3-1 | LIVMTQAAPSVPVTPGESVSISCR-SSKSLLHSNGNTYLYWFLQRPGQSPQLLIYRMSNLA 60 |
| 33 | CTC6_VL | DIVMTQAAPSVPVTPGESVSISCR-STKSLLHSNGNTYLYWFLQRPGQSPQRLIYHMSNLA 60 |
| 34 | CTD6_VL | DIVMTQAAPSVSVTPGESVSISCR-STKSLLHSNGNTYLYWLLQRPGQSPQRLIYHMSNLA 60 |
| 35 | CTA4_VL | DIKMTQSPSSVFASLGERVTITCK-ASQ-----NINSFLTWFHQKPGKSPTTLIYRITNRLI 55 |
| 36 | CTB4_VL | DIKMTQSPSSVFASLGERVTITCK-ASQ-----NINSFLTWFHQKPGKSPTTLIYRITNRLI 55 |
| 37 | 1E9_VL | SYVLTQ-PPSVSVSPGQTASVTCSGSSSNI----GNNYVSWYQQLPGTAPKLLIYDNNKRP 55 |
| 38 | 1A12_VL | SYVLTQ-PPSVSVSPGQTASVTCSGD-KL-----GNKYASWYQQKPGQSPVLVIYQDKKRP 55 |

FIG. 9A Cont.

Light Chain Variable Region Sequence Alignments (continued)

| SEQ ID NO. | CLONE NAME | CDR3 | |
|---|---|---|---|
| 3 | 1N23VL5-5 | SGVPDRFSGSGSGTDFTLKINRVEAEDLGVYFCSQSAHVP-WTFGGGTKLEIK- | 112 |
| 4 | 1N23VL5-8_0816 | SGVPDRFSGSGSGTDFTLKINRVEAEDLGVYFCSQSAHVP-WTFGGGTKLEIK- | 112 |
| 5 | 1N23VL1-8 | SGVPDRFSGSGSGTDFTLKINRVEAEDLGVYFCSQSAHVP-WTFGGGTKLEDW- | 112 |
| 6 | 1N23VL1-2_0820 | SGVPDRFSGSGSGTDFTLKINRVEAEDLGVYFCSQSAHVP-WTFGGGTKLEIK- | 112 |
| 7 | 1N23VL1-4_0820 | SGVPDRFSGSGSGTDFTLKINRVEAEDLGVYFCSQSAHVP-WTFGGGTKLEDW- | 112 |
| 8 | 1K23VL2-5 | SGVPDRFSGSGSGTDFTLKINRVEAEDLGVYFCSQSAHVP-WTFGGGTKLEIK- | 112 |
| 9 | 1N23VL1-2 | SGVPDRFSGSGSGTDFTLKINRVEAEDLGVYFCSQSAHVP-WTFGGGTKLEIK- | 112 |
| 10 | 1K23VL2-6 | SGVPDRFSGSGSGTDFTLKINRVEAEDLGVYFCSQSAHVP-WTFGGGTKLEIK- | 112 |
| 11 | 1K23VL2-8_0822 | SGVPDRFSGSGSGTDFTLKINRVEAEDLGVYFCSQSAHVP-WTFGGGTKLEIK- | 112 |
| 12 | 1K23VL2-3_0829 | SGVPDRFSGSGSGTDFTLKINRVEAEDLGVYFCSQSAHVP-WTFGGGTKKTGS- | 112 |
| 13 | 2K4VL1-3_0820 | SGVPDRFSGSGSGTDFTLKISRVEAEDLGVYFCSQSTHVP-PTFGGGTKLEIK- | 112 |
| 14 | 2K4VL1-4 | SGVPDRFSGSGSGTDFTLKISRVEAEDLGVYYCFQGSHV---LTFGGGTKLEIK- | 111 |
| 15 | 2K4VL1-1 | SGVPDRFSGSGSGTDFTLKISRVEAEDLGVYYCFQGSHV---LTFGGGTKLEIK- | 111 |
| 16 | 2K4VL1-6_0820 | SGVPDRFSGSGSGTDFTLKISRVEAEDLGVYYCFQGSHV---LTFGGGTKLEIK- | 111 |
| 17 | 1C9VL2-4 | SGVPDRFSGSGSGTAFTLRISRVEAEDVGVYYCMQHLEYP-LTFGAGTKLEIK- | 112 |
| 18 | 1C9VL2-6 | SGVPDRFSGSGSGTAFTLRISRVEAEDVGVYYCMQHLEYP-LTFGAGTKLEIK- | 112 |
| 19 | 1C9VL2-3_0816 | SGVPDRFSGSGSGTAFTLRISRVEAEDVGVYYCMQHLEYP-LTFGAGTKLEIK- | 112 |
| 20 | 2K4VL2-5_0816 | SGVPDRFSGSGSGTAFTLRISRVEAEDVGVYYCMQHLEYP-LTFGAGTKLEIK- | 112 |
| 21 | 2K4VL2-4 | SGVPDRFSGSGSGTAFTLRISRVEAEDVGVYYCMQHLEYP-LTFGAGTKLEIK- | 112 |

FIG. 9B

| | | | |
|---|---|---|---|
| 22 | 2K4VL2-6_0816 | SGVPDRFSGSGSGTAFTLRISRVEAGDVGVYYCMQHLEYP-LTFGAGTKLEIK- | 112 |
| 23 | 1J20VL5-2_0907 | SGVPDRFSGSGSGTAFTLRISRVEAEDVGVYYCMQHLEYP-LTFGAGTKLELK- | 112 |
| 24 | 1J20VL5-6_0907 | SGVPDRFSGSGSGTAFTLRISRVEAEDVGVYYCMQHLEYP-LTFGAGTKLELK- | 112 |
| 25 | 1J20VL4-3_0907 | SGVPDRFSGSGSGTAFTLRISRVEAEDVGVYYCMQHLEYP-LTFGAGTKLELK- | 112 |
| 26 | 1L20VL5-0912_0917 | SGVPDRFSGSGSGTAFTLRISRVEAEDVGVYYCMQHLEYP-LTFGAGTKLELK- | 112 |
| 27 | 1K3VL2-5 | SGVPDRFSGSGSGTAFTLRISRVEAEDVGVYYCMQHLEYP-LTFGAGTKLELR- | 112 |
| 28 | 1K3VL2-3 | SGVPDRFSGSGSGTAFTLRISRVEAEDVGVYYCMQHLEYP-LTFGAGTKLELK- | 112 |
| 29 | 1K3VL2-4 | SGVPDRFSGSGSGTAFTLRISRVEAEDVGVYYCMQHLEYP-LTFGAGTKLELK- | 112 |
| 30 | 2K4VL2-5 | SGVPDRFSGSGSGTAFTLRISRVEAEDVGVYYCMQHLEYP-LTFGAGTKLELK- | 112 |
| 31 | 1L5VL2-4 | SGVPDRFSGSGSGTAFTLRISRVAAEDVGVYYCLQQLEYP-FTFGGGTKLEIK- | 112 |
| 32 | 1L5VL3-1 | SGVPDRFSGSGRGSGTAFTLRISRVEAEDVGVYYCLQQLEYP-FTFGGGTKLEIK- | 112 |
| 33 | CTC6_VL | SGVPDRFSGRGSGTDFTLRISRVEAEDVGVYYCMQGLEYP-LTFGAGTKLGLK- | 112 |
| 34 | CTD6_VL | SGVPDRFSGRGSGTDFTLRISRVEAEDVGVYYCMQGLEYP-LTFGAGTKVELK- | 112 |
| 35 | CTA4_VL | DGVPSRFSGSGSGQDYSLTINSLEFEDMGIYYCLQYDFP-LTFGAGTKVELK- | 107 |
| 36 | CTB4_VL | DGVPSRFSGSGSGQDYSLTINSLELEDMGIYYCLQYDDFP-LTFGAGTKVELK- | 107 |
| 37 | 1E9_VL | SGIPDRFSGSKSGTSATLGITGLQTGDEADYCSSYTSSSWVFGGGKVTVLG | 110 |
| 38 | 1A12_VL | SGIPERFSGSNSGNTATLTISGTQAMDEADYCQAWDSRT-VVIGRGHLTVLG | 108 |

FIG. 9B Cont.

Heavy Chain Variable Region Sequence Alignments

| SEQ ID NO. | CLONE NAME | | CDR1 | CDR2 | |
|---|---|---|---|---|---|
| 39 | 1K3VH6-7 | LVQLQQSGAELARPGASVKLSCKASGYTFTSYW | MQWVKQRPGQGLEW | GAIYPG--NGDT | 58 |
| 40 | 1K3VH6-8_0816 | LVQLQQSGAELARPGASVKLSCKASGYTFTSYW | MQWVKQRPGQGLEW | GAIYPG--NGDT | 58 |
| 41 | 1K3VH3-8 | LVQLKQSGAELARPGASVKLSCKASGYTFTSYW | MQWVKQRPGQGLEW | GAIYPG--NGDT | 58 |
| 42 | 2K4VH3-8 | LVQLKQSGAELARPGASVKLSCKASGYTFTSYW | MQWVKQRPGQGLEW | GAIYPG--NGDT | 58 |
| 43 | 1K3VH3-4 | SVQLKQSGAELARPGASVKLSCKASGYTFTSYW | MQWVKQRPGQGLEW | GAIYPG--NGDT | 58 |
| 44 | 1K3VH3-3_0816 | SVQLKQSGAELARPGASVKLSCKASGYTFTSYW | MQWVKQRPGQGLEW | GAIYPG--NGDT | 58 |
| 45 | 2K4VH2-8 | RSQLKESGAELARPGASVKLSCKASGYTFTSYW | MQWVKQRPGQGLEW | GAIYPG--NGDT | 58 |
| 46 | 2K4VH1-1 | SVKLQESGAELARPGASVKLSCKASGYTFTSYW | MQWVKQRPGQGLEW | GAIYPG--NGDT | 58 |
| 47 | 2K4VH1-4 | SVKLQESGAELARPGASVKLSCKASGYTFTSYW | MQWVKQRPGQGLEW | GAIYPG--NGET | 58 |
| 48 | 1C9_VH404-8_1024 | QVQLQESGAELARPGASVKLSCKASGFTFTNYW | MQWIKQRPGQGLEW | GAIYPG--DGET | 58 |
| 49 | 1C9_VH405-12_1024 | QVQLQESGAELARPGAPVKLSCKASGFTFTNYW | MQWIKQRPGQGLEW | GAIYPG--DGET | 58 |
| 50 | 1C9_VH411-1_1024 | QVQLQESGAELARPGASVKLSCKASGFTFTNYW | MQWIKQRPGQGLEW | GAIYPG--DGET | 58 |
| 51 | 1C9_VH406-4_1024 | QVQLQESGAELARPGASVKLSCKASGYTFTTSYW | MQWIKQRPGQGLEW | GAIYPG--NGDT | 58 |
| 52 | 1L20VH2-3_0903 | QVQLKESGAELARPGASVKLSCKASGYTFTTSYW | MQWVKQRPGQGLEW | GAIYPG--NGDT | 58 |
| 53 | 1L20VH2-1_0907 | QVQLKESGAELARPGASVKLSCKASGYTFTTSYW | MQWVKQRPGQGLEW | GAIYPG--NGDT | 58 |
| 54 | 1L20VH2-3_0910 | QVQLKESGAELARPGASVKLSCKASGYTFTTSYW | MQWVKQRPGQGLEW | GAIYPG--NGDT | 58 |
| 55 | 1J20VH1-7_0910 | SVKLQESGAELARPGASVKLSRKASGYTFTTSYW | MQWVKQRPGQGLEW | GAIYPG--NGDT | 58 |
| 56 | 1J20VH1-1-6_0829 | QVQLQQSGAALVRPGASVKLSCKASGYSFTSYW | MNWVKQRPGLGLEW | GMIHPS--DSET | 58 |
| 57 | 1L5VH003-5-8_0907 | EVQLQQSGAALVRPGASVKLSCKASGYSFTSYW | MNWVKQRPGLGLEW | GMIHPS--DSET | 58 |
| 58 | 1L5VH003-6-3_0907 | EVQLQQSGAALVRPGASVKLSCKASGYSFTSYW | MNWVKQRPGLGLEW | GMIHPS--DSET | 58 |
| 59 | 1L5VH001-7-6_0907 | EVQLQQSGAALVRPGASVKLSCKASGYSFTSYW | MNWVKQRPGLGLEW | GMIHPS--DSET | 58 |

FIG. 10A

| # | Name | Sequence | Pos |
|---|---|---|---|
| 60 | 1L5VH001-6-5_0907 | EVQLQQSGAALVRPGASVKLSCKASGYSFTSYWMNWVKQRPGLGLEWIGMIHPS--DSET | 58 |
| 61 | 1L5VH001-6-11 | EVQLQQSGAALVRPGASVKLSCKASGYSFTSYWMNWVKQRPGLGLEWIGMIHPS--DSET | 58 |
| 62 | 1L5VH003-6-2_0910 | EVQLQQSGAALVRPGASVKLSCKASGYSFTSYWMNWVKQRPGLGLEWIGMIHPS--DSET | 58 |
| 63 | 1L5VH001-6-12_0907 | RVQLQQSGAALVRPGASVKLSCKASGYSFTSYWMNWVKQRPGLGLEWIGMIHPS--DSET | 58 |
| 64 | 1L5VH003-3-4_0907 | QVQLKQSGAALVRPGASVKLSCKASGYSFTSYWMNWVKQRPGLGLEWIGMIHPS--DSET | 58 |
| 65 | 1L5VH003-3-8_0907 | QVQLKQSGAALVRPGASVLSRKSSGYTFTTFWINWVRQRPGQGLEWIGNIYPG--DAAT | 58 |
| 66 | CTC2_VH | QVQLQQPGSEFVKPGASVKLSCKSSGYTFTTFWINWVRQRPGQGLEWIGNIYPG--DAAT | 58 |
| 67 | CTD2_VH | QVQLQQPGSEFVKPGASVRLSCKSSGYTFTTFWINWVRQRPGQGLEWIGNIYPG--DAAT | 58 |
| 68 | CTA5_VH | EVRLVETGGGIVQPEGSLKLSCAASGFTFNANAMNWVRQVPGKGLEWVARIRSKTRNYAI | 60 |
| 69 | CTB11_VH | EVRLVETGGGIVQPEGSLKLSCAASGFTFNANAMNWVRQVPGKGLEWVARIRSKTRNYAI | 60 |
| 70 | 1N23VH3-5 | LVQLKQSGPSLVKPSQTLSLTCSVTGDSVTSGYWNWIRKFPGNKLEYMGYISYS---GNT | 57 |
| 71 | 1N23VH3-7 | LVQLKQSGPSLVKPSQTLSLTCSVTGDSVTSGYWNWIRKFPGNKLEYMGYISYS---GNT | 57 |
| 72 | 1N23VH2-1 | LVQLKESGPSLVKPSQTLSLTCSVTGDSVTSGYWNWIRKFPGNKLEYMGYISYS---GNT | 57 |
| 73 | 1K23VH2-1_0910 | SVQLKESGPSLVKPSQTLSLTCSVTGDSVTSGYWNWIRKFPGNKLEYMGYISYS---GNT | 57 |
| 74 | 1K23VH1-4_0907 | DVKLQESGPSLVKPSQTLSLTCSVTGDSVTSGYWNWIRKFPGNKLEYMGYISYS---GNT | 57 |
| 75 | 1K23VH1-10_0907 | DVKLQESGPSLVKPSQTLSLTCSVTGDSVTSGYWNWIRKFPGNKLEYMGYISYS---GNT | 57 |
| 76 | 1N23VH1-5 | LVKLQESGPSLVKPSQTLSLTCSVTGDSVTSGYWNWIRKFPGNKLEYMGYISYS---GNT | 57 |
| 77 | 1K23VH8-4_0907 | EVKLVESGPSLVKPSQTLSLTCSVTGDSVTSGYWNWIRKFPGNKLEYMGYISYS---GNT | 57 |
| 78 | 1K23VH8-5_0907 | EVKLVESGPSLVKPSQTLSLTCSVTGDSVTSGYWNWIRKFPGNKLEYMGYISYS---GNT | 57 |
| 79 | 1K23VH8-9_0907 | QVQLQQSGGGLVKPGGSLRLSCTASGFTFSSYWMTWVRQAPGKGLEWVANIKRD--GSEK | 58 |
| 80 | 1E9_VH1E3 | QVQLQQSGGGLVKPGGSLRLSCTASGFTFSSYWMTWVRQAPGKGLEWVANIKRD--GSEK | 58 |
| 81 | 1E9_VH1D5 | QVNLRESGGGVVQPGRSLRLSCAASGFTFSNYGMHWVRQAPGKGLEWVAAISYD--GINK | 58 |
| 82 | 1A12_VH | QVNLRESGGGVVQPGRSLRLSCAASGFTFSNYGMHWVRQAPGKGLEWVAAISYD--GINK | 58 |

FIG. 10A Cont.

Heavy Chain Variable Region Sequence Alignments (continued)

| SEQ ID NO. | CLONE NAME | | CDR3 | |
|---|---|---|---|---|
| 39 | 1K3VH6-7 | RYTQKFKGKATLTADKSSSTAYMQLSSLASEDSAVYYCARG | ----GLAWFAYW | GQGTLVTVSA | 117 |
| 40 | 1K3VH6-8_0816 | RYTQKFKGKATLTADKSSSTAYMQLSSLASEDSAVYYCARG | ----GLAWFAYW | GQGTLVTVSA | 117 |
| 41 | 1K3VH3-8 | RYTQKFKGKATLTADKSSSTAYMQLSSLASEDSAVYYCARG | ----GLAWFAYW | GQGTLVTVSA | 117 |
| 42 | 2K4VH3-8 | RYTQKFKGKATLTADKSSSTAYMQLSSLASEDSAVYYCARG | ----GLAWFAYW | GQGTLVTVSA | 117 |
| 43 | 1K3VH3-4 | RYTQKFKGKATLTADKSSSTAYMQLSSLASEDSAVYYCARG | ----GLAWFAYW | GQGTLVTVSA | 117 |
| 44 | 1K3VH3-3_0816 | RYTQKFKGKATLTADKSSSTAYMQLSSLASEDSAVYYCARG | ----GLAWFAYW | GQGTLVTVSA | 117 |
| 45 | 2K4VH2-8 | RYTQKFKGKATLTADKSSSTAYMQLSSLASEDSAVYYCARG | ----GLAWFAYW | GQGTLVTVSA | 117 |
| 46 | 2K4VH1-1 | RYTQKFKGKATLTADKSSSTAYMQLSSLASEDSAVYYCARG | ----GLAWFAYW | GQGTLVTVSA | 117 |
| 47 | 2K4VH1-4 | RYTQKFKGKATLTADKSSSTAYMQLSSLASEDSAVYYCARG | ----GLAWFAYW | GQGTLVTVSA | 117 |
| 48 | 1C9_VH404-8_1024 | RHTQKFKGKATLTADKSSSTAYMQLSSLASEDSAVYYCASGYP | ----YFAYW | GQGTLVTVSA | 116 |
| 49 | 1C9_VH405-12_1024 | RHTQKFKGKATLTADKSSSTAYMQLSSLASEDSAVYYCASGYP | ----YFAYW | GQGTLVTVSA | 116 |
| 50 | 1C9_VH411-1_1024 | RHTQKFKGKATLTADKSSSTAYMQLSSLASEDSAVYYCASGYP | ----YFAYW | GQGTLVTVSA | 116 |
| 51 | 1C9_VH406-4_1024 | RHTQKFKGKATLISADKSSSTAYMQLSSLASEDSAVYYCASGYP | ----YFAYW | GQGTLVTVSA | 116 |
| 52 | 1L20VH2-3_0903 | RYTQKFKGKATLTADKSSSTANMQLSLASEDSAVYYCAKGD | ----GNFWFAYW | GQGTLVTVSA | 118 |
| 53 | 1J20VH2-1_0907 | RYTQKFKGKATLTADKSSSTANMQLSLASEDSAVYYCAKGD | ----GNFWFAYW | GQGTLVTVSA | 118 |
| 54 | 1L20VH2-3_0910 | RYTQKFKGKATLTADKSSSTANMQLSLASEDSAVYYCAKGD | ----GNFWFAYW | GQGTLVTVSA | 118 |
| 55 | 1J20VH1-7_0910 | RYTQKFKGKATLTADKSSSTANMQLSLASEDSAVYYCAKGD | ----GNFWFAYW | GQGTLVTVSA | 118 |
| 56 | 1J20VH1-1-6_0829 | RLNQKFKDKATLTVDKSSSTAYMQLSPTSEDSAVYYCACRY | ----DRSYFDYW | GQGTTLTVSS | 118 |
| 57 | 1L5VHOC3-5-8_0907 | RLNQKFKDKATLTVDKSSSTAYMQLSPTSEDSAVYYCACRY | ----DRSYFDYW | GQGTTLTVSS | 118 |
| 58 | 1L5VHOC3-6-3_0907 | RLNQKFKDKATLTVDKSSSTAYMQLSPTSEDSAVYYCACRY | ----DRSYFDYW | GQGTTLTVSS | 118 |
| 59 | 1L5VHOC1-7-6_0907 | RLNQKFKDKATLTVDKSSSTAYMQLSPTSEDSAVYYCACRY | ----DRSYFDYW | GQGTTLTVSS | 118 |
| 60 | 1L5VHOC1-6-5_0907 | RLNQKFKDKATLTVDKSSSTAYMQLSPTSEDSAVYYCACRY | ----DRSYFDYW | GQGTTLTVSS | 118 |
| 61 | 1L5VHOC1-6-11_0907 | RLNQKFKDKATLTVDKSSSTAYMQLSPTSEDSAVYYCACRY | ----DRSYFDYW | GQGTTLTVSS | 118 |

FIG. 10B

| | | | |
|---|---|---|---|---|
| 62 | 1L5VH003-6-2_0910 | RLNQKFKDKATLTVDKSSTAYMQLSSPTSEDSAVYYCACRY----DRSYFDYWGQGTTLTVSS | 118 |
| 63 | 1L5VH001-6-12_0907 | RLNQKFKDKATLTVDKSSTAYMQLSSPTSEDSAVYYCACRY----DRSYFDYWGQGTTLTVSS | 118 |
| 64 | 1L5VH003-3-4_0907 | RLNQKFKDKATLTVDKSSTAYMQLSSPTSEDSAVYYCACRY----DRSYFDYWGQGTTLTVSS | 118 |
| 65 | 1L5VH003-3-8_0907 | RLNQKFKDKATLTVDKSSTAYMQLSSPTSEDSAVYYCACRY----DRSYFDYWGQGTTLTVSS | 118 |
| 66 | CTC2_VH | RFNEKFKGKATLSVDTSSTAYMHLFSLTSDDSAVYYCVRS--------GDFWGQGTTLTVSS | 113 |
| 67 | CTD2_VH | RFNEKFKGKATLSVDTSSTAYMHLFSLTSDDSAVYYCVRS--------GDFWGQGTTLTVSS | 113 |
| 68 | CTA5_VH | YYADSVKDRFTISRDDSQSMIYLQMFNLKTEDTAMYYCVRD-------GNWWGQGTSVTVSS | 115 |
| 69 | CTB11_VH | YYADSVKDRFTISRDDSQSMIYLQMFNLKTEDTAMYYCVRD-------GNWWGQGTSVTVSS | 115 |
| 70 | 1N23VH3-5 | YYNPSLKSRISITRDTSKNQYYLQLNSVTTEDTATYYCARYNSLLRLGAMDYWGQGTSVTVSS | 120 |
| 71 | 1N23VH3-7 | YYNPSLKSRISITRDTSKNQYYLQLNSVTTEDTATYYCARYNSLLRLGAMDYWGQGTSVTVSS | 120 |
| 72 | 1N23VH2-1 | YYNPSLKSRISITRDTSKNQYYLQLNSVTTEDTATYYCARYNSLLRLGAMDYWGQGTSVTVSS | 120 |
| 73 | 1K23VH2-1_0910 | YYNPSLKSRISITRDTSKNQYYLQLNSVTTEDTATYYCARYNSLLRLGAMDYWGQGTSVTVSS | 120 |
| 74 | 1K23VH1-4_0907 | YYNPSLKSRISITRDTSKNQYYLQLNSVTTEDTATYYCARYNSLLRLGAMDYWGQGTSVTVSS | 120 |
| 75 | 1K23VH1-10_0907 | YYNPSLKSRISITRDTSKNQYYLQLNSVTTEDTATYYCARYNSLLRLGAMDYWGQGTSVTVSS | 120 |
| 76 | 1N23VH1-5 | YYNPSLKSRISITRDTSKNQYYLQLNSVTTEDTATYYCARYNSLLRLGAMDYWGQGTSVTVSS | 120 |
| 77 | 1K23VH8-4_0907 | YYNPSLKSRISITRDTSKNQYYLQLNSVTTEDTATYYCARYNSLLRLGAMDYWGQGTSVTVSS | 120 |
| 78 | 1K23VH8-5_0907 | YYNPSLKSRISITRDTSKNQYYLQLNSVTTEDTATYYCARYNSLLRLGAMDYWGQGTSVTVSS | 120 |
| 79 | 1K23VH8-9_0907 | YYNPSLKSRISITRDTSKNQYYLQLNSVTTEDTATYYCARYNSLLRLGAMDYWGQGTSVTVSS | 120 |
| 80 | 1E9_VH1E3 | YYVDSVKGRFTISRDNAKNSLYLQMNSIRAEDTAVYYCARGGNS-----YYGWGQGTLVTVSS | 116 |
| 81 | 1E9_VH1D5 | YYADSVKGRFTISRDNAKNSLYLQMNSIRAEDTAVYYCARGGNS-----FRDWGQGTLVTVSS | 116 |
| 82 | 1A12_VH | YYADSVKGRFTISRDNSKNTLYLQMNSIRAEDTAVYYCAKDRED----GMDVWGQGTTVTVSA | 117 |

FIG. 10B Cont.

Unique Light Chain CDR Sequence Alignments

| SEQ ID NO. | CDR1 | SEQ ID NO. | CDR2 | SEQ ID NO. | CDR3 |
|---|---|---|---|---|---|
| 83 | QSLVHSNGNTY | 89 | KVS | 96 | SQSAHVP-WT |
| 84 | QNIVHSNGNTY | 90 | KIS | 97 | SQSTHVP-PT |
| 85 | KSLLHSNGNTY | 91 | RMS | 98 | FQGSHV--LT |
| 86 | QNI------NSF | 92 | HMS | 99 | MQHLEYP-LT |
| 87 | SNI-----GNNY | 93 | RTN | 100 | LQQLEYP-FT |
| 88 | KL------GNKY | 94 | DNN | 101 | MQGLEYP-LT |
|  |  | 95 | QDK | 102 | LQYDDFP-LT |
|  |  |  |  | 103 | SSYTSSSSWV |
|  |  |  |  | 104 | QAWDSRTVVI |

FIG. 11

Unique Heavy Chain CDR Sequence Alignments

| SEQ ID NO. | CDR1 | SEQ ID NO. | CDR2 | SEQ ID NO. | CDR3 |
|---|---|---|---|---|---|
| 105 | GYTFTSYW | 113 | IYPG--NGDT | 122 | ARG------GIAWFAY |
| 106 | GFTFTNYW | 114 | IYPG--NGET | 123 | ASGYP-------YFAY |
| 107 | GYSFTSYW | 115 | IYPG--DGET | 124 | AKG--D--GNFWFAY |
| 108 | GYTFTTFW | 116 | IHPS--DSET | 125 | ACRY-D---RSYFDY |
| 109 | GFTFNANA | 117 | IYPG--DAAT | 126 | VRS---------GDF |
| 110 | GDSVTSGY | 118 | IRSKTRNYAI | 127 | VR---D-------GWW |
| 111 | GFTFSSYW | 119 | ISYS----GNT | 128 | ARYNS-LLRLGAMDY |
| 112 | GFTFSNYG | 120 | IKRD--GSEK | 129 | ARGGN-S-----YYG |
|  |  | 121 | ISYD--GINK | 130 | ARGGN-S-----FRD |
|  |  |  |  | 131 | AKDRED----G-MDV |

ANTI-VASA ANTIBODIES, AND METHODS OF PRODUCTION AND USE THEREOF

This application is a continuation of U.S. application Ser. No. 14/856,380, filed Sep. 16, 2015, which claims the benefit of priority of U.S. Provisional Application No. 62/089,054, filed Dec. 8, 2014, and U.S. Provisional Application No. 62/051,130, filed Sep. 16, 2014, the entire contents of which are hereby incorporated by reference in their entirety.

FIELD OF THE INVENTION

The present disclosure relates generally to antibodies, their production and use. Specifically, the present disclosure pertains to antibodies which specifically bind to the human VASA protein, methods of producing such antibodies, and diagnostic, therapeutic and clinical methods of using such antibodies.

BACKGROUND

The VASA protein was identified in *Drosophila* as a component of the germplasm that encodes a DEAD-family ATP-dependent RNA helicase (Liang et al. (1994), *Development*, 120:1201-11; Lasko et al. (1988), *Nature* 335:611-17). The molecular function of VASA is directed to binding target mRNAs involved in germ cell establishment, oogenesis, and translation onset (Gavis et al. (1996), *Development* 110:521-28). VASA is required for pole cell formation and is exclusively restricted to the germ cell lineage throughout development.

Vasa homolog genes have been isolated in various animal species, and VASA can be used as a molecular marker for the germ cell lineage in most animal species (Noce et al. (2001), *Cell Structure and Function* 26:131-36). Castrillon et al. (2000), *Proc. Natl. Acad. Sci.* (*USA*) 97(17):958590-9590, for example, demonstrated that the human Vasa gene is expressed in ovary and testis but is undetectable in somatic tissues.

The existence of mammalian female germline stem cells, also known as oogonial stem cells or ovarian stem cells (OSCs) or egg precursor cells, in the somatic tissue of mammalian ovaries was first described in Johnson et al. (2004), *Nature* 428:145-50, and has now been confirmed by other research groups (e.g., Zou et al. (2009), *Nature Cell Biology*, published online DOI: 10.1038/ncb1869; Telfer & Albertini (2012), *Nature Medicine* 18(3):353-4). The potential use of OSCs to produce oocytes for use in artificial reproduction technologies (ART), including in vitro fertilization (IVF), or as sources of highly functional mitochondria for mitochondrial transfer to oocytes, as well as the use of OSCs to treat various symptoms of menopause, have been described in the scientific and patent literature (e.g., Tilly & Telfer (2009), *Mol. Hum. Repro.* 15(7):393-8; Zou et al. (2009), supra; Telfer & Albertini (2012), supra; White et al. (2012), *Nature Medicine* 18(3):413-21; WO 2005/121321; U.S. Pat. No. 7,955,846; U.S. Pat. No. 8,652,840; WO2012/142500; U.S. Pat. No. 8,642,329 and U.S. Pat. No. 8,647,869).

When OSCs were first characterized by Johnson et al. (2004), supra, it was demonstrated that the cells expressed the VASA protein, and antibodies against the VASA protein have been used to isolate OSCs from ovarian tissue homogenates (e.g., Zou et al. (2009), supra; White et al. (2012), supra). Moreover, White et al. (2012), supra, demonstrated that antibodies to an N-terminal domain of VASA could not be used to isolate viable VASA-expressing OSCs whereas antibodies to a C-terminal domain could effectively isolate the cells, suggesting that the C-terminal domain, but not the N-terminal domain, was extracellular and thus accessible to the antibodies.

The production of anti-VASA polyclonal antibodies was first described in Castrillon et al. (2000), supra, and WO01/36445. Polyclonal antibodies directed to the C-terminal portion of human VASA protein are commercially available from Abcam plc (Cambridge, UK; Product Code AB13840), and R&D Systems, Inc. (Minneapolis, Minn.; Catalog No. AF2030), and a monoclonal antibody directed against the N-terminal portion of human VASA is also commercially available from R&D Systems, Inc. (Minneapolis, Minn.; Catalog No. AF2030), There remains, however, a need for high affinity antibodies directed to the C-terminal extracellular domain of VASA for identifying (e.g., by immunohistochemistry or labeled antibodies) and isolating (e.g., by magnetic or fluorescence activated cell sorting) cells, including but not limited to OSCs, expressing VASA.

SUMMARY

Anti-VASA antibodies (mAbs), particularly humanized mAbs that specifically bind to VASA with high affinity, are disclosed. The amino acid sequences of the CDRs of the light chains and the heavy chains, as well as consensus sequences for these CDRs, of these anti-VASA mAbs are provided. The disclosure also provides nucleic acid molecules encoding the anti-VASA mAbs, expression vectors, host cells, methods for making the anti-VASA mAbs, and methods for expressing the anti-VASA mAbs. Finally, methods of using the anti-VASA mAbs to isolate and/or purify cells expressing VASA are disclosed.

These and other aspects and embodiments of the disclosure are illustrated and described below. Other systems, processes, and features will become apparent to one with skill in the art upon examination of the following drawings and detailed description. It is intended that all such additional systems, processes, and features be included within this description, be within the scope of the present invention, and be protected by the accompanying claims.

BRIEF DESCRIPTION OF THE FIGURES

FIG. 1 provides the amino acid sequence of the human VASA protein isoform 1 from GenBank Accession from NP_077726 (SEQ ID NO: 1).

FIG. 2 provides the amino acid sequence of the mouse VASA homolog protein isoform 1 from GenBank Accession from NP_001139357 (SEQ ID NO: 2).

FIG. 3 provides an amino acid alignment between the C-terminal portion of the human VASA protein (residues 690-724 of SEQ ID NO: 1) and the mouse VASA homolog (residues 691-728 of SEQ ID NO: 2).

FIG. 4A shows the region of the C-terminal domains of the VASA/DDX4 polypeptide that is reactive with an antibody of the invention and the control antibody (AB13840, Abcam plc, Cambridge, UK) and FIG. 4B shows binding of the control antibody to the VASA protein and the V1 and V2 polypeptides.

FIGS. 9A-9B show alignments of some of the VL sequences of the anti-VASA invention. The figure indicates the approximate locations of the three CDR regions (bold, underscore) and the SEQ ID NO corresponding to each sequence.

FIGS. 10A-10B show alignments of some of the VH sequences of the anti-VASA invention. The figure indicates the approximate locations of the three CDR regions (bold, underscore) and the SEQ ID NO corresponding to each sequence.

FIG. 11 shows alignments of the unique CDR sequences of the VL regions of FIG. 9.

FIG. 12 shows alignments of the unique CDR sequences of the VH regions of FIG. 10.

DETAILED DESCRIPTION

Figure 5A:
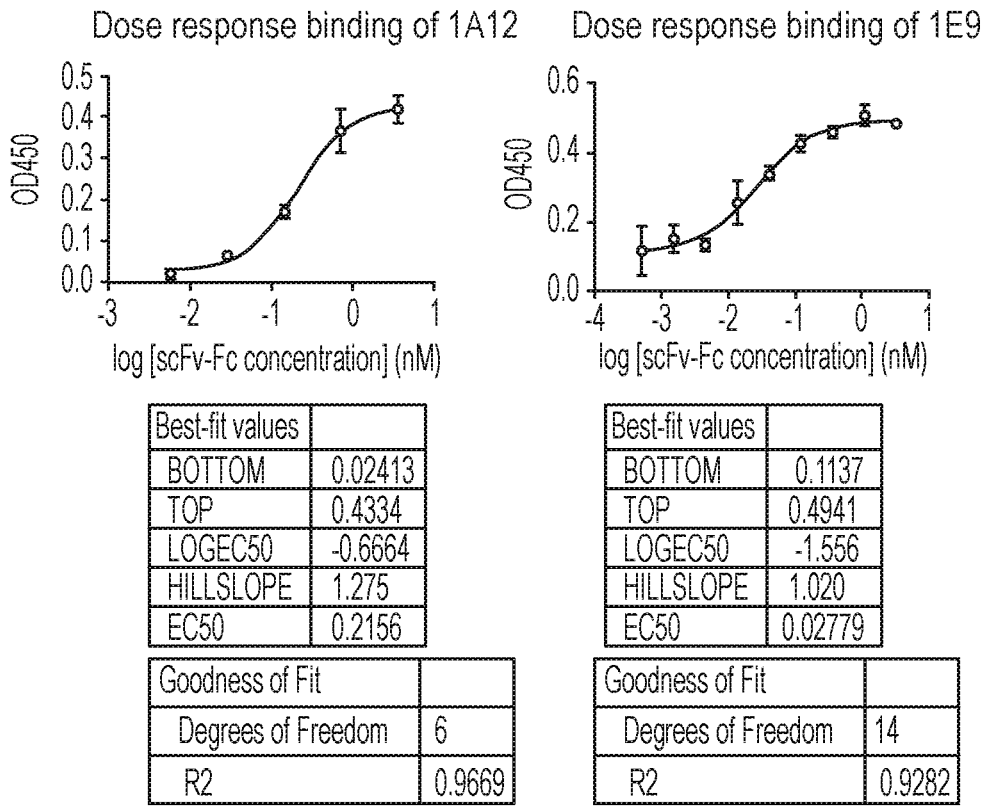
FIG. 5A shows dose response binding curves of the affinity for VASA of 1E9 and 1A12.

The present disclosure relates to isolated antibodies (Abs), particularly Abs that bind specifically to VASA with high affinity. In certain embodiments, the anti-VASA Abs are derived from particular heavy and light chain sequences and/or comprise particular structural features, such as CDR regions comprising particular amino acid sequences. This disclosure provides isolated anti-VASA Abs, methods of making such anti-VASA Abs, immunoconjugates and bispecific molecules comprising such anti-VASA Abs, and methods of expressing such anti-VASA Abs. This disclosure also relates to methods of using the anti-VASA Abs to isolate and/or purify cells expressing VASA, including mammalian female germline stem cells or oogonial stem cells (OSCs) or egg precursor cells and their progenitor cells.

In order that the present disclosure may be more readily understood, certain terms are defined. Additional definitions are set forth throughout the detailed description.

DEFINITIONS

The term "antibody" or abbreviation "Ab," as used herein, includes whole antibodies and any antigen binding fragment (i.e., "antigen-binding portion") or single chains thereof, with or without native glycosylation. A complete "antibody" refers to a glycoprotein comprising at least two heavy (H) chains and two light (L) chains inter-connected by disulfide bonds or an antigen binding portion thereof. Each heavy chain includes a heavy chain variable region ($V_H$) and a heavy chain constant region. The heavy chain constant region is comprised of three domains, $C_{H1}$, $C_{H2}$, and $C_{H3}$. Each light chain includes a light chain variable region ($V_L$) and a light chain constant region with one domain, $C_L$. The $V_H$ and $V_L$ regions can be further subdivided into complementarity determining regions (CDR) and framework regions (FR). The $V_H$ and $V_L$ regions each include three CDRs, designated CDR1, CDR2 and CDR3, that interact with an antigen (e.g., VASA).

The term "antigen-binding portion" of an antibody, as used herein, refers to one or more fragments of an antibody that retain the ability to specifically bind to an antigen (e.g., VASA). Examples of binding fragments encompassed within the term "antigen-binding portion" of an antibody include a Fab fragment, F(ab')$_2$ fragment, Fab' fragment, Fd fragment, Fv fragment, scFv fragment, dAb fragment, and an isolated CDR.

The term "monoclonal antibody" or "monoclonal antibody preparation," as used herein, refers to a preparation of antibody molecules consisting essentially of antibodies having a single heavy chain amino acid sequence and a single light chain amino acid sequence (but which may have heterogeneous glycosylation).

The term "humanized antibody," as used herein, includes antibodies having constant region and variable region framework regions (FRs) but not CDRs derived from human germline immunoglobulin sequences.

The term "recombinant antibody," as used herein, includes all antibodies prepared, expressed, created, or isolated by recombinant means. In certain embodiments, recombinant antibodies are isolated from a host cell transformed to express the antibody (e.g., from a transfectoma). In other embodiments, recombinant antibodies are isolated from a recombinant, combinatorial antibody library, such as a phage display library. Recombinant antibodies may also be prepared, expressed, created, or isolated by any other means that involve splicing of human immunoglobulin gene sequences to other DNA sequences.

The term "isotype," as used herein, refers to the heavy chain class (e.g., IgA, IgD, IgE, IgG, and IgM for human antibodies) or light chain class (e.g., kappa or lambda in humans) encoded by the constant region genes. The term "subtype" refers to subclasses within the subtype (e.g., IgA$_1$, IgA$_2$, IgG$_1$, IgG$_2$, IgG$_3$, IgG$_4$ in humans).

The phrase "an antibody specific for" a specified antigen is used interchangeably herein with the phrase "an antibody which specifically binds to" a specified antigen. As used herein, the term "K$_a$" refers to the association rate and the term "K$_d$" to the dissociation rate of a particular antibody-antigen complex. The term "K$_D$" refers to the dissociation constant, which is obtained from the ratio of K$_d$ to K$_a$ and expressed as a molar concentration (M). According to some embodiments, an antibody that "specifically binds to human VASA" is intended to refer to an antibody that binds to human VASA with a K$_D$ of 5×10$^{-8}$ M or less, more preferably 1×10$^{-8}$ M or less.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Anti-VASA Antibodies

The invention provides a variety of new antibodies with high affinity against the human VASA protein, particularly the C-terminal region. The antibodies may comprise the complete VH and VL regions disclosed herein, or may comprise only the CDR sequences disclosed herein. In addition, based upon CDR sequences disclosed herein, sequence motifs for CDR sequences are provided, and the antibodies may comprise CDR sequences defined by the motifs.

The CDR sequences of the invention (including both the CDRs disclosed in FIGS. 11 and 12 and the CDRs defined by the sequence motifs disclosed herein) can be combined with other immunoglobulin sequences according to methods well known in the art to produce immunoglobulin molecules with antigen-binding specificity determined by the CDRs of the invention.

In some embodiments, the CDRs of the invention are combined with framework region (FR) and constant domain (CH or CL) sequences from other antibodies. For example, although some of the CDRs disclosed herein are derived from murine hybridomas and have murine FR and constant domain sequences, they can be recombined with human or other mammalian FR and constant domain sequences to produce humanized or other recombinant antibodies. The production of such recombinant antibodies is well known to those of skill in the art and requires only routine experimentation.

The type of constant regions included in such recombinant antibodies can be chosen according to their intended use. For example, if the antibodies are intended for therapeutic use to target VASA-expressing cells for destruction, heavy chain constant domains (i.e., Fc regions) of IgG subtypes can be used. If the antibodies are intended only as reagents for labeling cells (e.g., for fluorescence-activated cell sorting (FACS)), a complete antibody, antigen binding fragment (Fab), single-chain variable fragment (Fsc), single domain antibody (sdAb) or even non-antibody immunoglobulin molecule (e.g., an MHC receptor extracellular domain) can be used with the CDRs of the invention.

The CDRs of the invention can be selected independently such that the CDR1, CDR2 and CDR3 sequences of a given variable light (VL) chain or variable heavy (VH) chain can be chosen from different original VL and VH chains, from different VL and VH CDR motifs, or from a combination of the disclosed CDRs and motifs. However, sequences for light chain CDRs should be selected from the disclosed VL CDRs or VL CDR motifs, and sequences for heavy chain CDRs should be selected from the disclosed VH CDRs or VH CDR motifs. Similarly, the sequences for CDR1 regions should be selected from the disclosed CDR1 or CDR1 motif sequences, the sequences for CDR2 regions should be selected from the disclosed CDR2 or CDR2 motif sequences, and the sequences for CDR3 regions should be selected from the disclosed CDR3 or CDR3 motif sequences, for VL or VH chains as appropriate.

Methods of Using Anti-VASA Antibodies to Detect or Isolate Cells

The anti-VASA antibodies of the invention can be used in standard methods of immunoaffinity purification, immunohistochemistry and immunotherapy, but with specific application to cells and tissue expressing the VASA protein.

For example, the anti-VASA antibodies of the invention can be used to isolate cells expressing VASA from a mixed population of cells including only a fraction of cells that express VASA. For example, female germline stem cells or oogonial stem cells or their precursors have been discovered to be present in ovarian tissue at very low proportions. Ovarian tissue (e.g., ovarian surface epithelial and/or cortex) can be excised, dissociated into individual cells, and subjected to techniques such as FACs using fluorescently-labeled anti-VASA antibodies or immunoaffinity purification using immobilized anti-VASA antibodies. The isolated VASA-expressing cells have various utilities in assisted reproductive technologies, as described above.

Alternatively, immunohistochemistry may be performed using the anti-VASA antibodies of the invention to identify cells or tissues expressing VASA and/or to quantify VASA expression in such cells.

In addition, the anti-VASA antibodies of the invention can be used therapeutically to target VASA-expressing cells for destruction either by antibody-dependent cell-mediated cytotoxicity (ADCC) or immunotoxins comprising anti-VASA antibodies of the invention conjugated to radio- or chemo-toxic moieties. Antibody-drug conjugates of the anti-VASA antibodies of the invention could also be used to deliver therapeutic drugs to VASA-expressing cells.

Nucleic Acid Molecules Encoding Anti-VASA Antibodies

The invention also provides nucleic acid molecules encoding the anti-VASA antibodies of the invention. Such nucleic acids can be designed using standard tables for the universal genetic code to choose codons which will encode the desired amino acid sequence, or specialized codon tables can be used that reflect codon biases characteristic of different organisms. Thus, for example, to optimize expression of the anti-VASA antibodies of the invention in CHO cells, a nucleic acid encoding the desired antibody can be designed using a codon table optimized for CHO cells.

The nucleic acids encoding the anti-VASA antibodies of the invention can be included in a wide variety of vectors known in the art, including cloning vectors (e.g., bacterial or mammalian cloning vectors), transformation vectors (e.g., homologous recombination, viral integration or autonomously replicating vectors) and expression vectors (e.g., high copy number, inducible or constitutive mammalian expression vectors).

Cells Expressing Anti-VASA Antibodies

Also provided are host cells expressing heterologous sequences encoding the anti-VASA antibodies of the invention. Such host cells can be useful for commercial production of the anti-VASA antibodies of the invention, and can be produced by transforming appropriate host cells with expression vectors described above.

In some embodiments the invention provides mammalian cells, including CHO cells, expressing the anti-VASA antibodies of the invention. However, those of skill in the art can express the antibodies in a variety of host cells, including bacterial, yeast, insect and mammalian systems. See, e.g., Verma et al. (1998), *J. Immunol. Methods* 216(1-2):165-81, incorporated by reference in its entirety herein.

Examples

Immunogenic Peptides

The following peptides were used as immunogens to generate antibodies against the C-terminal domain of human VASA and to screen for antibodies with high affinity binding to VASA:

VASA-1 (V1) immunogen: SQAPNPVDDE (SEQ ID NO: 1 residues 712-721)

VASA-2 (V2) immunogen: GKSTLNTAGF (SEQ ID NO: 1 residues 700-709)

As shown in FIG. 3, these immunogens comprise amino acid sequences from the C-terminal domain of VASA that are highly conserved between the human VASA protein and the mouse VASA homolog.

Hybridoma Generation

Hybridomas were formed in separate experiments with the VASA peptide immunogens V1 and V2 (above). Peptides were conjugated to carrier proteins by standard methods. Conjugated peptides were used to immunize mice, and to increase the immune response through boosting with the conjugated peptide. Following a period of increased antibody titer in the sera, animals were sacrificed and spleens removed. Splenic B cells were fused to mouse fusion partner cell lines (SP2-0) for isolation and cloning. Hybridomas were formed by outgrowth at limiting dilution, and clones were developed by cloning titration experiments. The presence of VASA-reactive antibodies was examined by ELISA assays. Hybridomas were derived by outgrowth and stabilization of cells plated at limiting dilution cell cloning.

The binding of the VASA-reactive antibodies in the region of the C-terminal domains of the VASA/DDX4 polypeptide was compared with the binding control antibodies (AB13840, Abcam plc, Cambridge, UK) to delineate the similarity of the binding epitopes. Exemplary results are shown in FIG. 4.

Analysis of Hybridomas

Hybridomas were injected intraperitoneally into mice and, after allowing for a period of growth, ascites fluid was collected and purified, all using standard procedures, and then analyzed by ELISA.

Figure 7A:
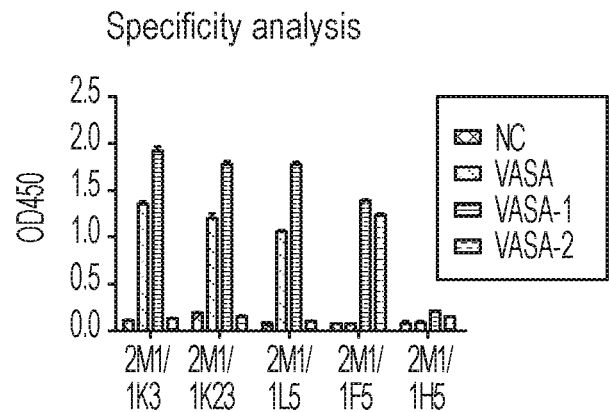
FIG. 7A shows the results of binding experiments with three anti-VASA hybridoma antibodies (2M1/1K3, 2M1/1K23 and 2M1/1L5) and two negative controls (2M1/1F5 and 2M1/1H5) which are not VASA-specific.
Figure 7B:
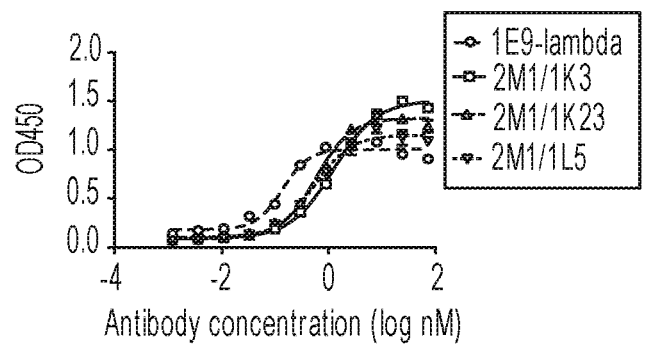
FIG. 7B shows dose response curves of four VASA-specific hybridoma antibodies (2M1/1K3, 2M1/1K23 and 2M1/1L5) compared to 1E9-lambda.
Figure 7C:
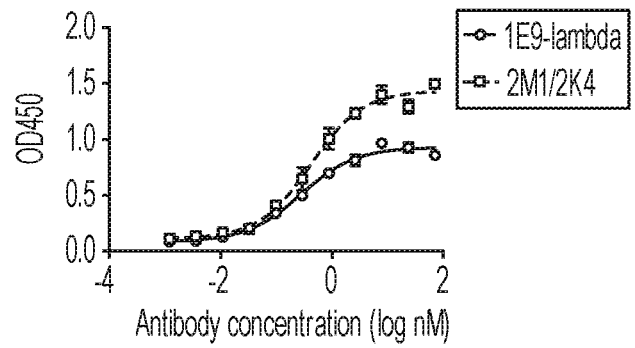
FIG. 7C shows dose response curves of the VASA-specific hybridoma antibody 2M1/2K4 compared to 1E9-lambda.

Binding of the ascites-derived antibodies to the VASA, VASA-1 and VASA-2 polypeptides was used to select antibodies for further analysis. For example, as shown in FIG. 7, the binding of four anti-VASA hybridoma antibodies (2M1/1K3, 2M1/1K23, 2M1/1L5 and 2M1/2K4) were compared to two negative controls (2M1/1F5 and 2M1/1H5) which are not VASA-specific and/or to the 1E9-lambda antibody (described below).

Recombinant Library Panning

As an alternative to hybridoma technology, the generation of antibodies against amino acid residues 700-724 of human VASA/DDX4 was conducted using phage display technology. The phage display library was formed from a pool of normal B cells from ~40 blood donors. Phage were used to display the scFv chain of an antibody The results of panning the human naïve scFv library against the VASA/DDX4 700-724 peptide were as shown in Table 1 below:

TABLE 1

| Peptide | Round | Titer of output phage (cfu/ml) | Titer of rescued phage (cfu/ml) | ELISA results |
|---------|-------|-------------------------------|--------------------------------|---------------|
| VASA | 1$^{st}$ | 10$^7$ | 10$^{13}$ | / |
| | 2$^{nd}$ | 10$^7$ | 10$^{13}$ | / |
| | 3$^{rd}$ | 10$^7$ | 10$^{12}$ | No positive clones |
| | 4$^{th}$ | 10$^7$ | 10$^{13}$ | Two positive clones |
| | 5$^{th}$ | 10$^7$ | 10$^{13}$ | Several positive clones |
| | 6$^{th}$ | 10$^7$ | / | / |

ELISA results of single colonies identified after 3 and 4 rounds of selection are shown in Tables 2-4 below. Two clones were of note: "1A12" (plate 1, row A, column 12) and "1E9" (plate 1, row E, column 9).

TABLE 2

| plate 1 | | | | | | | | | | | | |
|---|---|---|---|---|---|---|---|---|---|---|---|---|
| | 3 rounds | | | | | | 4 rounds | | | | | |
| | VASA peptide | | | | | | | | | | | |
| | 1 | 2 | 3 | 4 | 5 | 6 | 7 | 8 | 9 | 10 | 11 | 12 |
| A. | 0.062 | 0.061 | 0.057 | 0.063 | 0.065 | 0.092 | 0.059 | 0.059 | 0.059 | 0.060 | 0.059 | 0.550 |
| B. | 0.055 | 0.058 | 0.056 | 0.056 | 0.064 | 0.073 | 0.060 | 0.057 | 0.060 | 0.58 | 0.063 | 0.059 |
| C. | 0.065 | 0.058 | 0.060 | 0.063 | 0.069 | 0.072 | 0.069 | 0.063 | 0.066 | 0.061 | 0.070 | 0.063 |
| D. | 0.072 | 0.064 | 0.067 | 0.066 | 0.061 | 0.062 | 0.069 | 0.069 | 0.070 | 0.070 | 0.117 | 0.071 |
| E. | 0.778 | 0.058 | 0.055 | 0.071 | 0.056 | 0.059 | 0.057 | 0.056 | 0.458 | 0.064 | 0.060 | 0.059 |
| F. | 0.057 | 0.059 | 0.059 | 0.060 | 0.059 | 0.062 | 0.063 | 0.057 | 0.059 | 0.057 | 0.059 | 0.056 |
| G. | 0.058 | 0.055 | 0.056 | 0.082 | 0.061 | 0.066 | 0.061 | 0.057 | 0.056 | 0.058 | 0.068 | 0.055 |
| H. | 0.044 | 0.058 | 0.058 | 0.056 | 0.053 | 0.096 | 0.056 | 0.052 | 0.056 | 0.054 | 0.054 | 0.056 |
| | non-relevant peptide | | | | | | | | | | | |
| | 1 | 2 | 3 | 4 | 5 | 6 | 7 | 8 | 9 | 10 | 11 | 12 |
| A. | 0.085 | 0.063 | 0.062 | 0.069 | 0.056 | 0.089 | 0.054 | 0.059 | 0.056 | 0.057 | 0.057 | 0.061 |
| B. | 0.062 | 0.053 | 0.054 | 0.06 | 0.09 | 0.066 | 0.063 | 0.054 | 0.054 | 0.058 | 0.058 | 0.062 |
| C. | 0.064 | 0.063 | 0.071 | 0.069 | 0.069 | 0.067 | 0.062 | 0.06 | 0.057 | 0.062 | 0.064 | 0.057 |
| D. | 0.094 | 0.063 | 0.067 | 0.069 | 0.069 | 0.067 | 0.071 | 0.067 | 0.067 | 0.066 | 0.135 | 0.061 |
| E. | 0.078 | 0.058 | 0.059 | 0.116 | 0.055 | 0.057 | 0.054 | 0.064 | 0.061 | 0.054 | 0.056 | 0.059 |
| F. | 0.062 | 0.056 | 0.056 | 0.056 | 0.055 | 0.064 | 0.063 | 0.057 | 0.062 | 0.056 | 0.054 | 0.058 |
| G. | 0.057 | 0.06 | 0.059 | 0.066 | 0.056 | 0.064 | 0.057 | 0.057 | 0.057 | 0.055 | 0.077 | 0.055 |
| H. | 0.061 | 0.066 | 0.061 | 0.054 | 0.058 | 0.111 | 0.057 | 0.054 | 0.057 | 0.058 | 0.052 | 0.054 |

TABLE 3 plate 2-after 4 round of selection

| | 1 | 2 | 3 | 4 | 5 | 6 | 7 | 8 | 9 | 10 | 11 | 12 |
|---|---|---|---|---|---|---|---|---|---|---|---|---|
| VASA peptide | | | | | | | | | | | | |
| A. | 0.052 | 0.045 | 0.053 | 0.045 | 0.051 | 0.045 | 0.046 | 0.044 | 0.049 | 0.044 | 0.045 | 0.050 |
| B. | 0.049 | 0.051 | 0.051 | 0.045 | 0.042 | 0.054 | 0.046 | 0.045 | 0.055 | 0.045 | 0.048 | 0.053 |
| C. | 0.048 | 0.047 | 0.048 | 0.054 | 0.051 | 0.047 | 0.047 | 0.045 | 0.047 | 0.052 | 0.051 | 0.055 |
| D. | 0.062 | 0.050 | 0.048 | 0.047 | 0.059 | 0.056 | 0.059 | 0.063 | 0.048 | 0.057 | 0.052 | 0.061 |
| E. | 0.047 | 0.042 | 0.042 | 0.045 | 0.051 | 0.041 | 0.047 | 0.042 | 0.044 | 0.052 | 0.050 | 0.054 |
| F. | 0.047 | 0.049 | 0.040 | 0.042 | 0.046 | 0.043 | 0.046 | 0.042 | 0.052 | 0.045 | 0.051 | 0.054 |
| G. | 0.047 | 0.052 | 0.045 | 0.041 | 0.039 | 0.051 | 0.048 | 0.049 | 0.052 | 0.043 | 0.054 | 0.050 |
| H. | 0.055 | 0.048 | 0.054 | 0.042 | 0.043 | 0.048 | 0.048 | 0.049 | 0.051 | 0.051 | 0.048 | 0.054 |
| non-relevant peptide | | | | | | | | | | | | |
| A. | 0.047 | 0.053 | 0.050 | 0.042 | 0.053 | 0.053 | 0.041 | 0.043 | 0.042 | 0.053 | 0.053 | 0.054 |
| B. | 0.052 | 0.053 | 0.054 | 0.054 | 0.053 | 0.043 | 0.043 | 0.045 | 0.053 | 0.045 | 0.055 | 0.054 |
| C. | 0.052 | 0.047 | 0.054 | 0.053 | 0.055 | 0.045 | 0.045 | 0.043 | 0.053 | 0.055 | 0.057 | 0.053 |
| D. | 0.047 | 0.049 | 0.054 | 0.056 | 0.047 | 0.049 | 0.054 | 0.051 | 0.056 | 0.062 | 0.065 | 0.062 |
| E. | 0.052 | 0.045 | 0.042 | 0.045 | 0.041 | 0.051 | 0.040 | 0.047 | 0.041 | 0.056 | 0.053 | 0.054 |
| F. | 0.052 | 0.053 | 0.041 | 0.045 | 0.052 | 0.053 | 0.054 | 0.052 | 0.533 | 0.049 | 0.045 | 0.053 |
| G. | 0.051 | 0.053 | 0.049 | 0.050 | 0.051 | 0.043 | 0.049 | 0.052 | 0.053 | 0.053 | 0.054 | 0.051 |
| H. | 0.055 | 0.052 | 0.054 | 0.053 | 0.045 | 0.051 | 0.051 | 0.051 | 0.052 | 0.062 | 0.054 | 0.053 |

TABLE 4 plate 3-after 4 rounds of selection

| | 1 | 2 | 3 | 4 | 5 | 6 | 7 | 8 | 9 | 10 | 11 | 12 |
|---|---|---|---|---|---|---|---|---|---|---|---|---|
| VASA peptide | | | | | | | | | | | | |
| A. | 0.074 | 0.052 | 0.058 | 0.076 | 0.052 | 0.063 | 0.052 | 0.055 | 0.040 | 0.052 | 0.054 | 0.072 |
| B. | 0.047 | 0.041 | 0.052 | 0.064 | 0.072 | 0.051 | 0.059 | 0.048 | 0.053 | 0.048 | 0.054 | 0.053 |
| C. | 0.051 | 0.042 | 0.042 | 0.044 | 0.053 | 0.056 | 0.052 | 0.048 | 0.044 | 0.048 | 0.060 | 0.056 |
| D | 0.057 | 0.049 | 0.045 | 0.051 | 0.053 | 0.046 | 0.067 | 0.047 | 0.046 | 0.046 | 0.059 | 0.058 |
| E. | 0.054 | 0.046 | 0.042 | 0.126 | 0.041 | 0.047 | 0.051 | 0.040 | 0.042 | 0.043 | 0.048 | 0.073 |
| F. | 0.077 | 0.045 | 0.040 | 0.047 | 0.042 | 0.040 | 0.042 | 0.039 | 0.041 | 0.053 | 0.051 | 0.051 |
| G. | 0.178 | 0.056 | 0.044 | 0.041 | 0.051 | 0.050 | 0.055 | 0.042 | 0.042 | 0.051 | 0.044 | 0.052 |
| H. | 0.054 | 0.042 | 0.045 | 0.041 | 0.049 | 0.039 | 0.045 | 0.089 | 0.050 | 0.051 | 0.061 | 0.055 |
| non-relevant peptide | | | | | | | | | | | | |
| A. | 0.050 | 0.056 | 0.055 | 0.049 | 0.053 | 0.055 | 0.051 | 0.059 | 0.051 | 0.044 | 0.047 | 0.054 |
| B. | 0.058 | 0.075 | 0.061 | 0.064 | 0.073 | 0.061 | 0.053 | 0.054 | 0.059 | 0.056 | 0.059 | 0.063 |
| C. | 0.076 | 0.056 | 0.053 | 0.054 | 0.056 | 0.053 | 0.053 | 0.053 | 0.057 | 0.063 | 0.049 | 0.061 |
| D. | 0.069 | 0.052 | 0.052 | 0.058 | 0.056 | 0.048 | 0.059 | 0.059 | 0.056 | 0.052 | 0.051 | 0.056 |
| E. | 0.047 | 0.056 | 0.050 | 0.118 | 0.063 | 0.067 | 0.052 | 0.053 | 0.054 | 0.053 | 0.056 | 0.054 |
| F. | 0.053 | 0.054 | 0.054 | 0.052 | 0.054 | 0.054 | 0.053 | 0.053 | 0.043 | 0.056 | 0.046 | 0.056 |
| G. | 0.063 | 0.056 | 0.054 | 0.045 | 0.045 | 0.049 | 0.050 | 0.053 | 0.053 | 0.052 | 0.055 | 0.053 |
| H. | 0.058 | 0.055 | 0.054 | 0.047 | 0.053 | 0.048 | 0.050 | 0.051 | 0.054 | 0.053 | 0.053 | 0.058 |

ELISA results of single colonies identified after 5 rounds of selection are shown in Tables 5-7 below. Clones of note included 1A11, 1B4, 1B7, 1D4, 1D5, 1E2, 1E3, 1F7, 1G3, 1G12, 2B8, 2C7, 2E11, 2F1, 2G8, 2G10, 2H9, 3B2, 3B5, 3B7, 3D11, 3E5, 3E12, 3F6 and 3H11.

TABLE 5 plate 1-after 5 rounds of selection

VASA peptide

|   | 1 | 2 | 3 | 4 | 5 | 6 | 7 | 8 | 9 | 10 | 11 | 12 |
|---|---|---|---|---|---|---|---|---|---|----|----|----|
| A. | 0.049 | 0.049 | 0.122 | 0.135 | 0.050 | 0.129 | 0.051 | 0.089 | 0.077 | 0.084 | 0.227 | 0.077 |
| B. | 0.051 | 0.197 | 0.056 | 0.212 | 0.067 | 0.099 | 0.280 | 0.109 | 0.122 | 0.094 | 0.049 | 0.053 |
| C. | 0.181 | 0.168 | 0.062 | 0.059 | 0.105 | 0.051 | 0.127 | 0.098 | 0.101 | 0.093 | 0.061 | 0.080 |
| D. | 0.057 | 0.186 | 0.143 | 0.408 | 0.527 | 0.057 | 0.178 | 0.061 | 0.124 | 0.060 | 0.061 | 0.077 |
| E. | 0.159 | 0.342 | 0.230 | 0.046 | 0.047 | 0.042 | 0.120 | 0.119 | 0.053 | 0.119 | 0.126 | 0.064 |
| F. | 0.160 | 0.177 | 0.160 | 0.086 | 0.048 | 0.134 | 0.248 | 0.053 | 0.079 | 0.054 | 0.159 | 0.052 |
| G. | 0.167 | 0.119 | 0.246 | 0.085 | 0.049 | 0.050 | 0.050 | 0.052 | 0.050 | 0.102 | 0.053 | 0.458 |
| H. | 0.126 | 0.136 | 0.096 | 0.050 | 0.048 | 0.049 | 0.060 | 0.049 | 0.058 | 0.104 | 0.066 | 0.052 | non-relevant peptide

|   | 1 | 2 | 3 | 4 | 5 | 6 | 7 | 8 | 9 | 10 | 11 | 12 |
|---|---|---|---|---|---|---|---|---|---|----|----|----|
| A. | 0.053 | 0.054 | 0.051 | 0.052 | 0.053 | 0.054 | 0.054 | 0.050 | 0.051 | 0.044 | 0.050 | 0.052 |
| B. | 0.056 | 0.054 | 0.053 | 0.053 | 0.052 | 0.052 | 0.062 | 0.053 | 0.052 | 0.053 | 0.054 | 0.053 |
| C. | 0.056 | 0.055 | 0.056 | 0.056 | 0.056 | 0.053 | 0.053 | 0.052 | 0.052 | 0.051 | 0.054 | 0.053 |
| D. | 0.060 | 0.060 | 0.060 | 0.057 | 0.065 | 0.059 | 0.058 | 0.061 | 0.052 | 0.056 | 0.057 | 0.055 |
| E. | 0.052 | 0.083 | 0.051 | 0.053 | 0.043 | 0.043 | 0.042 | 0.039 | 0.043 | 0.050 | 0.053 | 0.057 |
| F. | 0.052 | 0.052 | 0.050 | 0.050 | 0.041 | 0.040 | 0.048 | 0.043 | 0.050 | 0.053 | 0.052 | 0.052 |
| G. | 0.051 | 0.051 | 0.048 | 0.049 | 0.052 | 0.043 | 0.054 | 0.046 | 0.052 | 0.051 | 0.053 | 0.061 |
| H. | 0.052 | 0.048 | 0.046 | 0.049 | 0.044 | 0.050 | 0.050 | 0.049 | 0.049 | 0.051 | 0.051 | 0.052 |

TABLE 6 plate 2-after 5 rounds of selection

VASA peptide

|   | 1 | 2 | 3 | 4 | 5 | 6 | 7 | 8 | 9 | 10 | 11 | 12 |
|---|---|---|---|---|---|---|---|---|---|----|----|----|
| A. | 0.075 | 0.051 | 0.067 | 0.050 | 0.049 | 0.069 | 0.150 | 0.094 | 0.081 | 0.050 | 0.043 | 0.103 |
| B. | 0.136 | 0.054 | 0.107 | 0.075 | 0.059 | 0.052 | 0.120 | 0.318 | 0.159 | 0.095 | 0.152 | 0.052 |
| C. | 0.103 | 0.056 | 0.055 | 0.052 | 0.140 | 0.053 | 0.210 | 0.056 | 0.116 | 0.054 | 0.140 | 0.114 |
| D. | 0.098 | 0.141 | 0.058 | 0.114 | 0.104 | 0.057 | 0.070 | 0.077 | 0.079 | 0.049 | 0.138 | 0.054 |
| E. | 0.071 | 0.065 | 0.058 | 0.077 | 0.044 | 0.050 | 0.121 | 0.051 | 0.050 | 0.049 | 0.212 | 0.083 |
| F. | 0.210 | 0.051 | 0.046 | 0.110 | 0.043 | 0.063 | 0.043 | 0.056 | 0.052 | 0.057 | 0.051 | 0.062 |
| G. | 0.054 | 0.078 | 0.064 | 0.060 | 0.053 | 0.051 | 0.054 | 0.475 | 0.055 | 0.272 | 0.076 | 0.061 |
| H. | 0.050 | 0.050 | 0.050 | 0.054 | 0.050 | 0.054 | 0.051 | 0.050 | 0.290 | 0.055 | 0.061 | 0.056 | non-relevant peptide

|   | 1 | 2 | 3 | 4 | 5 | 6 | 7 | 8 | 9 | 10 | 11 | 12 |
|---|---|---|---|---|---|---|---|---|---|----|----|----|
| A. | 0.040 | 0.041 | 0.044 | 0.041 | 0.040 | 0.048 | 0.046 | 0.047 | 0.040 | 0.045 | 0.044 | 0.045 |
| B. | 0.039 | 0.052 | 0.039 | 0.047 | .042 | 0.050 | 0.052 | 0.060 | 0.053 | 0.042 | 0.045 | 0.043 |
| C. | 0.036 | 0.043 | 0.051 | 0.041 | 0.042 | 0.051 | 0.053 | 0.062 | 0.052 | 0.053 | 0.050 | 0.040 |
| D. | 0.047 | 0.055 | 0.048 | 0.046 | 0.047 | 0.051 | 0.049 | 0.058 | 0.048 | 0.052 | 0.054 | 0.052 |
| E. | 0.051 | 0.051 | 0.040 | 0.039 | 0.043 | 0.041 | 0.040 | 0.040 | 0.040 | 0.043 | 0.067 | 0.046 |
| F. | 0.054 | 0.051 | 0.046 | 0.045 | .47 | 0.040 | 0.043 | 0.050 | 0.043 | 0.049 | 0.048 | 0.040 |
| G. | 0.038 | 0.050 | 0.047 | 0.040 | 0.039 | 0.039 | 0.045 | 0.060 | 0.041 | 0.048 | 0.050 | 0.044 |
| H. | 0.039 | 0.058 | 0.039 | 0.040 | 0.049 | 0.048 | 0.050 | 0.049 | 0.058 | 0.048 | 0.044 | 0.049 |

TABLE 7

| plate 3-after 5 rounds of selection | | | | | | | | | | | | |
|---|---|---|---|---|---|---|---|---|---|---|---|---|
| VASA peptide | | | | | | | | | | | | |
| | 1 | 2 | 3 | 4 | 5 | 6 | 7 | 8 | 9 | 10 | 11 | 12 |
| A. | 0.047 | 0.122 | 0.105 | 0.176 | 0.177 | 0.102 | 0.040 | 0.164 | 0.104 | 0.109 | 0.169 | 0.081 |
| B. | 0.048 | 0.218 | 0.094 | 0.054 | 0.314 | 0.155 | 0.287 | 0.146 | 0.052 | 0.166 | 0.054 | 0.054 |
| C. | 0.199 | 0.059 | 0.052 | 0.105 | 0.060 | 0.054 | 0.118 | 0.152 | 0.054 | 0.145 | 0.055 | 0.053 |
| D. | 0.053 | 0.096 | 0.066 | 0.056 | 0.058 | 0.077 | 0.055 | 0.048 | 0.196 | 0.155 | 0.259 | 0.133 |
| E. | 0.139 | 0.052 | 0.052 | 0.046 | 0.471 | 0.089 | 0.199 | 0.052 | 0.049 | 0.042 | 0.173 | 0.244 |
| F. | 0.055 | 0.051 | 0.068 | 0.046 | 0.093 | 0.412 | 0.083 | 0.041 | 0.129 | 0.052 | 0.053 | 0.053 |
| G. | 0.101 | 0.056 | 0.058 | 0.039 | 0.051 | 0.050 | 0.075 | 0.046 | 0.042 | 0.044 | 0.070 | 0.052 |
| H. | 0.135 | 0.083 | 0.062 | 0.052 | 0.052 | 0.050 | 0.056 | 0.071 | 0.073 | 0.094 | 0.200 | 0.050 |
| non-relevant peptide | | | | | | | | | | | | |
| | 1 | 2 | 3 | 4 | 5 | 6 | 7 | 8 | 9 | 10 | 11 | 12 |
| A. | 0.055 | 0.056 | 0.053 | 0.051 | 0.054 | 0.056 | 0.054 | 0.45 | 0.049 | 0.053 | 0.055 | 0.053 |
| B. | 0.057 | 0.057 | 0.054 | 0.055 | 0.059 | 0.056 | 0.056 | 0.044 | 0.058 | 0.052 | 0.054 | 0.055 |
| C. | 0.057 | 0.055 | 0.056 | 0.054 | 0.049 | 0.052 | 0.043 | 0.052 | 0.055 | 0.055 | 0.050 | 0.055 |
| D. | 0.060 | 0.062 | 0.059 | 0.058 | 0.061 | 0.058 | 0.057 | 0.047 | 0.059 | 0.058 | 0.061 | 0.059 |
| E. | 0.056 | 0.045 | 0.048 | 0.055 | 0.071 | 0.048 | 0.046 | 0.043 | 0.048 | 0.056 | 0.056 | 0.059 |
| F. | 0.054 | 0.045 | 0.055 | 0.047 | 0.053 | 0.070 | 0.044 | 0.052 | 0.053 | 0.053 | 0.054 | 0.055 |
| G. | 0.052 | 0.055 | 0.049 | 0.049 | 0.041 | 0.047 | 0.044 | 0.046 | 0.054 | 0.053 | 0.053 | 0.051 |
| H. | 0.053 | 0.052 | 0.057 | 0.041 | 0.046 | 0.044 | 0.051 | 0.051 | 0.052 | 0.052 | 0.048 | 0.050 |

Clones shown in bold were PCR amplified.
Conversion to scFv-Fc Fusion and Expression in Mammalian Cells After 5 rounds of panning, DNA digestion patterns showed that many clones from the 5$^{th}$ round of panning were the same, indicating that additional rounds of selection and ELISA analysis were not needed.

Figure 5B:
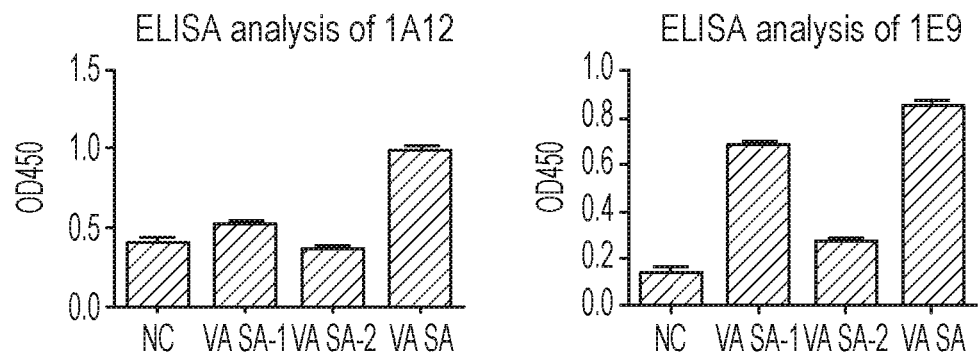
FIG. 5B shows the results of ELISA assays with the VASA, V1 and V2 peptides that suggest that 1E9 binds the same epitope as the commercially available rabbit polyclonal antibody (AB13840, Abcam plc, Cambridge, UK). NC=negative control; VASA=SEQ ID NO: 1 residues 700-724; VASA-1=V1 or SEQ ID NO: 1 residues 712-721; VASA-2=V2 or SEQ ID NO: 1 residues 700-709.

Two unique clones (1A12, 1E9) were selected for conversion to scFv-Fc fusions for expression in mammalian cells and for ELISA and FACS analysis. FIG. 5A shows dose response binding curves that indicated that 1E9 had an EC50 of 0.02779 nM and 1A12 had an EC50 of 0.2156 nM. In addition, FIG. 5B shows the results of ELISA assays with the V1 and V2 VASA peptides which suggest that 1E9 binds the same epitope as the commercially available rabbit polyclonal antibody (AB13840, Abcam plc, Cambridge, UK).

Figure 6A:
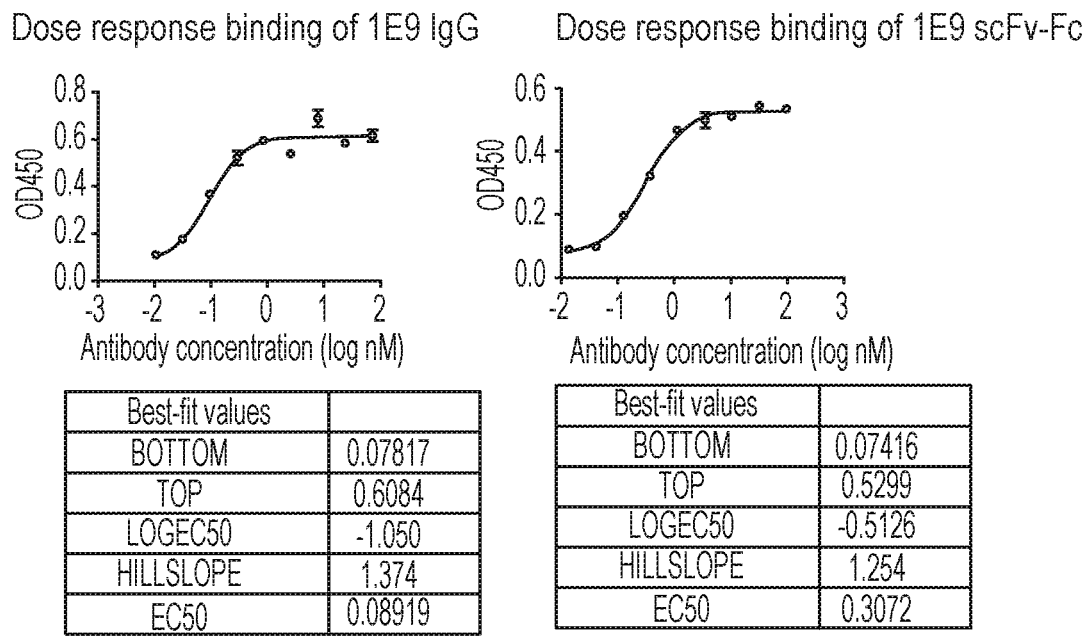
FIG. 6A shows dose response binding curves of the affinity for VASA of the IgG and scFv-Fc forms of 1E9.
Figure 6B:
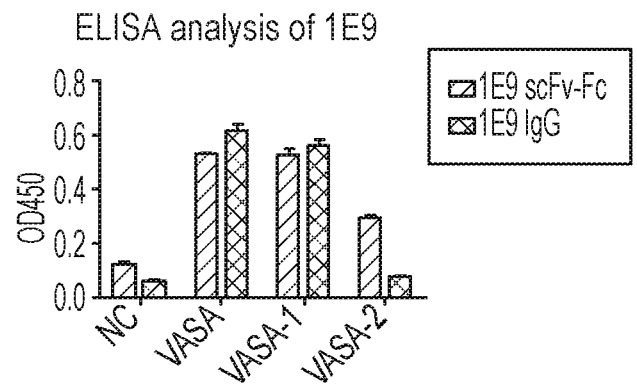
FIG. 6B shows the results of ELISA assays of the binding of the IgG and scFv-Fc forms of 1E9 with the VASA, V1 and V2 peptides. NC=negative control; VASA=SEQ ID NO: 1 residues 700-724; VASA-1=V1 or SEQ ID NO: 1 residues 712-721; VASA-2=V2 or SEQ ID NO: 1 residues 700-709.

Two different forms of the 1E9 antibody were compared: IgG and scFv-Fc. As shown in FIG. 6A, 1E9 IgG had an EC50 of 0.08919 nM and the 1E9 scFv-Fc had an EC50 of 0.3072 nM. In addition, as shown in FIG. 6B, both forms were specific towards the VASA-1 epitope.

Synthetic Antibody Gene Production

The following steps were employed to produce synthetic antibody genes:

(1) Subtype Determination of Hybridoma Antibodies.

Figure 8:
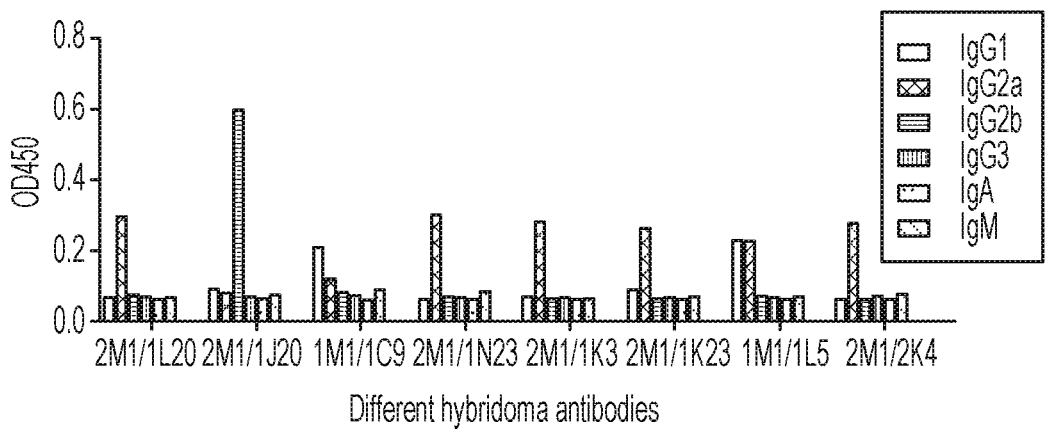
FIG. 8 shows the result of subtyping analysis for anti-VASA antibodies from eight hybridomas (2M1/1L20, 2M1/1J20, 1M1/1C9, 2M1/1N3, 2M1/1K23, 1M1/1L5 and 2M1/2K4).

The IgG subtypes of the hybridoma antibodies were determined using commercially available kits according to manufacturer's protocols (e.g., Mouse Monoclonal Antibody Isotyping Kit, Catalog No, MMTI, AbDSerotech, Kidlington, UK). FIG. 8 shows the result of subtyping analysis for anti-VASA antibodies from eight hybridomas (2M1/1L20, 2M1/1J20, 1M1/1C9, 2M1/1N3, 2M1/1K23, 1M1/1L5 and 2M1/2K4). All of the antibodies were IgG1, IgG2a or IgG2b.

(2) Degenerate Primer Synthesis.

Based on the subtype information for the eight hybridoma antibodies tested, degenerate primers for mouse IgG VH and VL were designed using sequence information from a mouse IgG database (i.e., the International Immunogenetics Information System® or MGT database; see Lefranc et al. (2003), *Leukemia* 17:260-266, and Alamyar et al. (2012), *Methods Mol. Biol.* 2012; 882:569-604). Ten degenerate forward primers were designed and synthesized for the VH chain and ten for the VL chain (9 for kappa and one for lambda chains). In addition, two degenerate reverse primers for the VH chain (one for the IgG1 and IgG2b subtypes, and one for the IgG2a subtype) and five for the VL chain (four for kappa and one for lambda chains) were designed and synthesized.

(3) RNA Extraction, Amplification, Cloning and Sequencing.

RNA was extracted from hybridoma cells by standard techniques, first strand cDNA synthesis was performed by standard techniques using gene-specific and oligo(dT) primers, and the cDNA was amplified using gene-specific primers. The amplified DNA was then ligated into a commercially available bacterial cloning vector (pMD18-T, Sino Biological, Inc., Beijing, China). Standard methodologies were conducted to transform the ligation products into *E. coli* DH5a, and to sequence positive clones.

Antibody Sequence Analyses

Clones producing potentially useful anti-Vasa antibodies were DNA sequenced and the corresponding amino acid sequences were deduced. Sequences are disclosed for eight antibodies derived from the hybridomas described above (i.e., 1N23, 1K23, 2K4, 1C9, 1J20, 1L20, 1K3, 1L5), four additional antibodies derived from hybridomas produced under contract (i.e., CTA4/5, CTB4/11, CTC2/6, CTD2/6) and two antibodies derived from phage display (i.e., 1A12 and 1E9).

Variable Light Chain Sequences

VL of 1N23.

Positive VL clones from the 1N23 hybridoma were sequenced and six were found to encode functional VL chains. These six clones were designated 1N23VL5-5, 1N23VL5-8_0816, 1N23VL1-8, 1N23VL1-2_0820, 1N23VL1-4_0820 and 1N23VL1-2.

VL of 1K23.

Positive VL clones from the 1K23 hybridoma were sequenced and four were found to encode functional VL chains. These four clones were designated 1K23VL2-5, 1K23VL2-6, 1K23VL2-8_0822 and 1K23VL2-3_0829.

VL of 2K4.

Positive VL clones from the 2K4 hybridoma were sequenced and eight were found to encode functional VL chains. These eight clones were designated 2K4VL1-3_0820, 2K4VL1-4, 2K4VL1-1, 2K4VL1-6_0820, 2K4VL2-5_0816, 2K4VL2-4, 2K4VL2-6_0816 and 2K4VL2-5.

VL of 1C9.

Positive VL clones from the 1C9 hybridoma were sequenced and three were found to encode functional VL chains. These three clones were designated 1C9VL2-4, 1C9VL2-6 and 1C9VL2-3_0816.

VL of 1J20.

Positive VL clones from the 1J20 hybridoma were sequenced and three were found to encode functional VL chains. These three clones were designated 1J20VL5-2_0907, 1J20VL5-6_0907 and 1J20VL4-3_0907.

VL of 1L20.

Positive VL clones from the 1L20 hybridoma were sequenced and one was found to encode a functional VL chain. That clone was designated 1L20VL5-0912_091.

VL of 1K3.

Positive VL clones from the 1K3 hybridoma were sequenced and four were found to encode functional VL chains. These four clones were designated 1K3VL2-5, 1K3VL2-5, 1K3VL2-3 and 1K3VL2-4.

VL of 1L5.

Positive VL clones from the 1L5 hybridoma were sequenced and two were found to encode functional VL chains. These two clones were designated 1L5VL2-4 and 1L5VL3-1.

Additional VLs.

VL sequences were obtained for four additional hybridoma antibodies designated CTA4 VL, CTB4 VL, CTC6 VL, CTD6 VL.

VL Sequence Alignments.

Alignments of all of the VL sequences described above are shown in FIG. 9. The figure indicates the approximate locations of the three CDR regions (bold, underscore) and the SEQ ID NO corresponding to each sequence.

Unique VL CDR Sequences.

Alignments of the unique CDR sequences of the VLs of FIG. 9 are shown in FIG. 11. Of the 34 VL sequences, there are only 5 unique CDR1 sequences, 6 unique CDR2 sequences and 8 unique CDR3 sequences, as shown in FIG. 11.

VL CDR Consensus Sequences.

Based on the sequences disclosed in FIG. 11, as well as structure/function characteristics of the naturally occurring amino acids, consensus sequences for the VL CDRs can be determined.

One consensus sequence is VL CDR1 Motif 1:

(SEQ ID NO: 132)
$X_1\ X_2\ X_3\ X_4\ X_5\ X_6\ X_7\ X_8\ X_9\ X_{10}\ X_{11}$ where $X_1$ is Q, N, K, R, S or T; $X_2$ is S, T, C, N or Q; $X_3$ is I, L, V, M or A; $X_4$ is V, L, I, M, A or absent; $X_5$ is H, K, R or absent; $X_6$ is S, T, C or absent; $X_7$ is N, Q or absent; $X_8$ is G, A or absent; $X_9$ is N or Q; $X_{10}$ is T, S, C, N or Q; and $X_{11}$ is Y, F or W. In some embodiments, $X_1$ is limited to Q, K or S; and/or $X_2$ is limited to S or N; and/or $X_3$ is limited to I or L; and/or $X_4$ is limited to V, L or absent; and/or $X_5$ is limited to H or absent; and/or $X_6$ is limited to S or absent; and/or $X_7$ is limited to N or absent; and/or $X_8$ is limited to G or absent; and/or $X_9$ is limited to N; and/or $X_{10}$ is limited to T, S or N; and/or $X_{11}$ is limited to Y or F. In some embodiments, the subsequence $X_1\ X_2\ X_3$ is limited to Q N I; in some embodiments, the subsequence $X_1\ X_2\ X_3$ is limited to Q S L; and in some embodiments, the subsequence $X_1\ X_2\ X_3$ is limited to K S L. In addition, in some embodiments, when $X_1\ X_2\ X_3$ is Q S L or Q N I, then $X_4$ is V; whereas in other embodiments, when $X_1\ X_2\ X_3$ is K S L, then $X_4$ is L. In some embodiments, when $X_9\ X_{10}$ is N T, then $X_{11}$ is Y.

Noting in particular that the VL CDR1 sequences of SEQ ID NOs: 86-88 are quite distinct from the others in FIG. 11, an alternative consensus sequence is VL CDR1 Motif 2:

(SEQ ID NO: 133)
$X_1\ X_2\ X_3\ X_4\ X_5\ X_6\ X_7\ X_8\ X_9\ X_{10}\ X_{11}$ where $X_1$ is Q, N, K or R; $X_2$ is S, T, C, N or Q; $X_3$ is I, L, V, M or A; $X_4$ is V, L, I, M or A; $X_5$ is H, K or R; $X_6$ is S, T or C; $X_7$ is N or Q; $X_8$ is G or A; $X_9$ is N or Q; $X_{10}$ is T, S or C; and $X_{11}$ is Y, F or W. In some embodiments, $X_1$ is limited to Q or K; and/or $X_2$ is limited to S or N; and/or $X_3$ is limited to I or L; and/or $X_4$ is limited to V or L; and/or $X_5$ is limited to H; and/or $X_6$ is limited to S; and/or $X_7$ is limited to N; and/or $X_8$ is limited to G; and/or $X_9$ is limited to N; and/or $X_{10}$ is limited to T; and/or $X_{11}$ is limited to Y. In some embodiments, the subsequence $X_1\ X_2\ X_3$ is limited to Q N I; in some embodiments, the subsequence $X_1\ X_2\ X_3$ is limited to Q S L; and in some embodiments, the subsequence $X_1\ X_2\ X_3$ is limited to K S L. In addition, in some embodiments, when $X_1\ X_2\ X_3$ is Q S L or Q N I, then $X_4$ is V; whereas in other embodiments, when $X_1\ X_2\ X_3$ is K S L, then $X_4$ is L. In some embodiments, when $X_9\ X_{10}$ is N T, then $X_{11}$ is Y.

For the VL CDR2, one consensus sequence is VL CDR2 Motif 1:

(SEQ ID NO: 134)
$Y_1\ Y_2\ Y_3$ where $Y_1$ is K, R or H; $Y_2$ is V, I, L, M, A, T, S or C; and $Y_3$ is S, T, C, N or Q. In some embodiments, $Y_2$ is limited to V, I, M or T; and/or $Y_3$ is limited to S or N.

Noting in particular that the VL CDR2 sequences of SEQ ID NO: 94 is quite distinct from the others in FIG. 11, an alternative consensus sequence is VL CDR2 Motif 2:

(SEQ ID NO: 135)
$Y_1\ Y_2\ Y_3$ where $Y_1$ is D or E; $Y_2$ is N or Q; and $Y_3$ is N or Q. In some embodiments, $Y_1$ is limited to D; and/or $Y_2$ is limited to N; and/or $Y_3$ is limited to N.

Similarly, noting that the VL CDR2 sequences of SEQ ID NO: 95 is quite distinct from the others in FIG. 11, an alternative consensus sequence is VL CDR2 Motif 3:

$$Y_1\ Y_2\ Y_3 \quad \text{(SEQ ID NO: 136)}$$

where $Y_1$ is Q or N; $Y_2$ is D or E; and $Y_3$ is K, R or H. In some embodiments, $Y_1$ is limited to Q; and/or $Y_2$ is limited to D; and/or $Y_3$ is limited to K.

For the VL CDR3, one consensus sequence is VL CDR3 Motif 1:

$$Z_1\ Z_2\ Z_3\ Z_4\ Z_5\ Z_6\ Z_7\ Z_8\ Z_9\ Z_{10} \quad \text{(SEQ ID NO: 137)}$$

where $Z_1$ is S, T, C, F, Y, M, L, V, I or A; $Z_2$ is Q, N, S, T or C; $Z_3$ is 5, T, C, G, A, H, K, R, Q, N, Y, F or W; $Z_4$ is A, G, S, T, C, L, I, V, M, D or E; $Z_5$ is H, K, R, E, D, S, T or C; $Z_6$ is V, L, I, M, A, Y, F, W, S, T or C; $Z_7$ is P, S, T, C or absent; $Z_8$ is 5, T, C or absent; $Z_9$ is W, P, L, I, V, M, A, F, or Y; and $Z_{10}$ is T, S, C, V, L, I, M, A. In some embodiments, $Z_1$ is limited to S, F, M or L; and/or $Z_2$ is limited to Q or S; and/or $Z_3$ is limited to S, G, H, Q or Y; and/or $Z_4$ is limited to A, S, T, L, or D; and/or $Z_5$ is limited to H, E, D or S; and/or $Z_6$ is limited to V, Y, F, or S; and/or $Z_7$ is limited to P, S or absent; and/or $Z_8$ is limited to S or absent; and/or $Z_9$ is limited to W, P, L or F; and/or $Z_{10}$ is limited to T or V.

Noting in particular that the VL CDR3 sequences of SEQ ID NOs: 96-98 have a positive charge at position $Z_5$ whereas the others in FIG. 11 do not, an alternative consensus sequence is VL CDR3 Motif 2:

$$Z_1\ Z_2\ Z_3\ Z_4\ Z_5\ Z_6\ Z_7\ Z_8\ Z_9\ Z_{10} \quad \text{(SEQ ID NO: 138)}$$

where $Z_1$ is S, T, C, F or Y; $Z_2$ is Q or N; $Z_3$ is 5, T, C, G or A; $Z_4$ is A, G, S, T or C; $Z_5$ is H, K or R; $Z_6$ is V, L, I, M or A; $Z_7$ is P or absent; $Z_8$ is absent; $Z_9$ is W, P, L, I, V, M, A, F or Y; and $Z_{10}$ is T, S, or C. In some embodiments, $Z_1$ is limited to S or F; and/or $Z_2$ is limited to Q; and/or $Z_3$ is limited to S or G; and/or $Z_4$ is limited to A, S or T; and/or $Z_5$ is limited to H; and/or $Z_6$ is limited to V; and/or $Z_7$ is limited to P or absent; and/or $Z_8$ is limited to absent; and/or $Z_9$ is limited to W, P, L or F; and/or $Z_{10}$ is limited to T.

Noting in particular that the VL CDR3 sequences of SEQ ID NOs: 99-102 have a negative charge at position $Z_5$ whereas the others in FIG. 11 do not, an alternative consensus sequence is VL CDR3 Motif 3:

$$Z_1\ Z_2\ Z_3\ Z_4\ Z_5\ Z_6\ Z_7\ Z_8\ Z_9\ Z_{10} \quad \text{(SEQ ID NO: 139)}$$

where $Z_1$ is M, C, L, I, V, A; $Z_2$ is Q or N; $Z_3$ is H, K, R, Q, N, G, A, Y or F; $Z_4$ is L, I, V, M, A, D or E; $Z_5$ is E or D; $Z_6$ is Y or F; $Z_7$ is P; $Z_8$ is absent; $Z_9$ is W, P, L, I, V, M, A, F or Y; and $Z_{10}$ is T, S, or C. In some embodiments, $Z_1$ is limited to M or L; and/or $Z_2$ is limited to Q; and/or $Z_3$ is limited to H, Q, G or Y; and/or $Z_4$ is limited to L or D; and/or $Z_5$ is limited to E or D; and/or $Z_6$ is limited to Y or F; and/or $Z_7$ is limited to P; and/or $Z_8$ is limited to absent; and/or $Z_9$ is limited to W, P, L or F; and/or $Z_{10}$ is limited to T.

Noting in particular that the VL CDR3 sequence of SEQ ID NO: 103 is quite distinct from the others in FIG. 11, an alternative consensus sequence is VL CDR3 Motif 4:

$$Z_1\ Z_2\ Z_3\ Z_4\ Z_5\ Z_6\ Z_7\ Z_8\ Z_9\ Z_{10} \quad \text{(SEQ ID NO: 140)}$$

where $Z_1$ is S, T or C; $Z_2$ is S, T or C; $Z_3$ is Y or F; $Z_4$ is T, S, or C; $Z_5$ is S, T or C; $Z_6$ is S, T or C; $Z_7$ is S, T or C; $Z_8$ is S, T or C; $Z_9$ is W, P, F or Y; and $Z_{10}$ is V, L, I, M, A, T, S or C. In some embodiments, $Z_1$ is limited to S or T; and/or $Z_2$ is limited to S or T; and/or $Z_3$ is limited to Y; and/or $Z_4$ is limited to T or S; and/or $Z_5$ is limited to S or T; and/or $Z_6$ is limited to S or T; and/or $Z_7$ is limited to S or T; and/or $Z_8$ is limited to S or T; and/or $Z_9$ is limited to W, P or F; and/or $Z_{10}$ is limited to V, L, I, T or S. In some embodiments, $Z_1$ is limited to S; and/or $Z_2$ is limited to S; and/or $Z_3$ is limited to Y; and/or $Z_4$ is limited to T; and/or $Z_5$ is limited to S; and/or $Z_6$ is limited to S; and/or $Z_7$ is limited to S; and/or $Z_8$ is limited to S; and/or $Z_9$ is limited to W; and/or $Z_{10}$ is limited to V.

Finally, noting in particular that the VL CDR3 sequence of SEQ ID NO: 104 is quite distinct from the others in FIG. 11, an alternative consensus sequence is VL CDR3 Motif 5:

$$Z_1\ Z_2\ Z_3\ Z_4\ Z_5\ Z_6\ Z_7\ Z_8\ Z_9\ Z_{10} \quad \text{(SEQ ID NO: 141)}$$

where $Z_1$ is Q or N; $Z_2$ is A or G; $Z_3$ is W, Y or F; $Z_4$ is D or E; $Z_5$ is S, T or C; $Z_6$ is R, K or H; $Z_7$ is T, S or C; $Z_8$ is V, I, L, M or A; $Z_9$ is V, I, L, M or A; and $Z_{10}$ is I, L, V, M or A. In some embodiments, $Z_1$ is limited to Q; and/or $Z_2$ is limited to A; and/or $Z_3$ is limited to W; and/or $Z_4$ is limited to D; $Z_5$ is limited to S; and/or $Z_6$ is limited to R; and/or $Z_7$ is limited to T; and/or $Z_8$ is limited to V; and/or $Z_9$ is limited to V; and/or $Z_{10}$ is limited to I.

Variable Heavy Chain Sequences

VH of 1N23.

Positive VH clones from the 1N23 hybridoma were sequenced and all four were found to encode functional VH chains. These four clones were designated 1N23VH3-5, 1N23VH3-7, 1N23VH2-1 and 1N23VH1-5.

VH of 1K23.

Positive VH clones from the 1K23 hybridoma were sequenced and six were found to encode functional VH chains. These six clones were designated 1K23VH2-1_0910, 1K23VH1-4_0907, 1K23VH1-10_0907, 1K23VH8-4_0907, 1K23VH8-5_0907 and 1K23VH8-9_0907.

VH of 2K4.

Positive VH clones from the 2K4 hybridoma were sequenced and four were found to encode functional VH chains. These four clones were designated 2K4VH3-8, 2K4VH2-8, 2K4VH1-1 and 2K4VH1-4.

VH of 1C9.

Positive VH clones from the 1C9 hybridoma were sequenced and eight were found to encode functional VL chains. These eight clones included four unique sequences which are designated 1C9VH2-404-8_1024, 1C9VH2-405-12_1024, 1C9VH2-411-1_1024 and 1C9VH2-406-4_1024.

VH of 1J20.

Positive VH clones from the 1J20 hybridoma were sequenced and two were found to encode functional VH chains. These two clones were designated 1J20VH1-7_0910 and 1J20VH1-1-6_0829.

VH of 1L20.

Positive VH clones from the 1L20 hybridoma were sequenced and three were found to encode functional VH chains. These three clones were designated 1L20VH2-3_0903, 1L20VH2-1_0907 and 1L20VH2-3_0910.

VH of 1K3.

Positive VH clones from the 1K3 hybridoma were sequenced and five were found to encode functional VH chains. These five clones were designated 1K3VH6-7, 1K3VH6-8_0816, 1K3VH3-4, 1K3VH3-4 and 1K3VH3-3_0816.

VH of 1L5.

Positive VH clones from the 1L5 hybridoma were sequenced and nine were found to encode functional VH chains. These nine clones were designated 1L5VH003-5-8_0907, 1L5VH003-6-3_0907, 1L5VH001-7-6_0907, 1L5VH001-6-5_0907, 1L5VH001-6-11_0907, 1L5VH003-6-2_0910, 1L5VH001-6-12_0907, 1L5VH003-3-4_0907 and 1L5VH003-3-8_0907.

Additional VHs.

VH sequences were obtained for four additional hybridoma antibodies designated CTA5_VH, CTB11_VH, CTC2_VH, CTD2_VH.

VH Sequence Alignments.

Alignments of all of the VH sequences described above are shown in FIG. 10. The figure indicates the approximate locations of the three CDR regions (bold, underscore) and the SEQ ID NO corresponding to each sequence.

Unique VH CDR Sequences.

Alignments of the unique CDR sequences of the VHs of FIG. 10 are shown in FIG. 12. Of the 43 VH sequences, there are only 8 unique CDR1 sequences, 9 unique CDR2 sequences and 10 unique CDR3 sequences, as shown in FIG. 12.

VH CDR Consensus Sequences.

Based on the sequences disclosed in FIG. 12, as well as structure/function characteristics of the naturally occurring amino acids, consensus sequences for the VH CDRs can be determined.

For the VH CDR1, one consensus sequence is VH CDR1 Motif 1:

$$X_1\ X_2\ X_3\ X_4\ X_5\ X_6\ X_7\ X_8 \quad \text{(SEQ ID NO: 142)}$$

where $X_1$ is G or A; $X_2$ is Y, F, W, D or E; $X_3$ is T, S, C or M; $X_4$ is F, Y, W, V, L, I, M or A; $X_5$ is T, S, C, N, or Q; $X_6$ is S, T, C, A or G; $X_7$ is Y, F, W, N, Q, G or A; and $X_8$ is W, A, G, Y or F. In some embodiments, $X_1$ is limited to G; and/or $X_2$ is limited to Y, F or D; and/or $X_3$ is limited to T or S; and/or $X_4$ is limited to F or V; and/or $X_5$ is limited to T, S or N; and/or $X_6$ is limited to S, T or A; and/or $X_7$ is limited to Y, F, N or G; and/or $X_8$ is limited to W, A or Y. In some embodiments, the subsequence $X_1\ X_2\ X_3$ is limited to G Y T; and in some embodiments, the subsequence $X_1\ X_2\ X_3$ is limited to G F T. In addition, in some embodiments, the subsequence $X_1\ X_7\ X_8$ is limited to S Y W.

Noting in particular that the VH CDR1 sequence of SEQ ID NOs: 109-110 and 112 are quite distinct from the others in FIG. 12, an alternative consensus sequence is VH CDR1 Motif 2:

$$X_1\ X_2\ X_3\ X_4\ X_5\ X_6\ X_7\ X_8 \quad \text{(SEQ ID NO: 143)}$$

where $X_1$ is G or A; $X_2$ is Y, F or W; $X_3$ is T, S, C or M; $X_4$ is F, Y or W; $X_5$ is T, S or C; $X_6$ is S, T or C; $X_7$ is Y, F or W; and $X_8$ is W. In some embodiments, $X_1$ is limited to G; and/or $X_2$ is limited to Y or F; and/or $X_3$ is limited to T or S; and/or $X_4$ is limited to F; and/or $X_5$ is limited to T or S; and/or $X_6$ is limited to S or T; and/or $X_7$ is limited to Y or F; and/or $X_8$ is limited to W. In some embodiments, the subsequence $X_1\ X_2\ X_3$ is limited to G Y T; and in some embodiments, the subsequence $X_1\ X_2\ X_3$ is limited to G F T. In addition, in some embodiments, the subsequence $X_1\ X_7\ X_8$ is limited to S Y W.

For the VH CDR2, one consensus sequence is VH CDR2 Motif 1:

$$Y_1\ Y_2\ Y_3\ Y_4\ Y_5\ Y_6\ Y_7\ Y_8\ Y_9\ Y_{10} \quad \text{(SEQ ID NO: 144)}$$

where $Y_1$ is I, L, V, M or A; $Y_2$ is Y, F, H, R, K, S or T; $Y_3$ is P, S, T, Y, F, R, K or H; $Y_4$ is G, A, S, T, K, R, H, D or E; $Y_5$ is T, S or absent; $Y_6$ is R, K, H or absent; $Y_7$ is N, Q, D, E, G, A or absent; $Y_8$ is G, A, S, T, Y or F; $Y_9$ is D, E, A, G, N or Q; and $Y_{10}$ is T, S, I, L, V, M, A, K, R or H. In some embodiments, $Y_1$ is limited to I; and/or $Y_2$ is limited to Y, H, R, K or S; and/or $Y_3$ is limited to P, S, Y or R; and/or $Y_4$ is limited to G, S, K or D; and/or $Y_5$ is limited to T or absent; and/or $Y_6$ is limited to R or absent; and/or $Y_7$ is limited to N, D, G or absent; and/or $Y_8$ is limited to G, A, S or Y; and/or $Y_9$ is limited to D, E, A or N; and/or $Y_{10}$ is limited to T, I or K.

Noting in particular that the VH CDR2 sequence of SEQ ID NO: 120-121 are quite distinct from the others in FIG. 12, an alternative consensus sequence is VH CDR2 Motif 2:

$$Y_1\ Y_2\ Y_3\ Y_4\ Y_5\ Y_6\ Y_7\ Y_8\ Y_9\ Y_{10} \quad \text{(SEQ ID NO: 145)}$$

where $Y_1$ is I, L, V, M or A; $Y_2$ is Y, F, H, R, K, S or T; $Y_3$ is P, S, T, Y or F; $Y_4$ is G, A, S, T, K, R or H; $Y_5$ is T, S or absent; $Y_6$ is R, K, H or absent; $Y_7$ is N, Q, D, E or absent; $Y_8$ is G, A, S, T, Y or F; $Y_9$ is D, E, A, G, N or Q; and $Y_{10}$ is T, S, I, L, V, M or A. In some embodiments, $Y_1$ is limited to I; and/or $Y_2$ is limited to Y, H, R or S; and/or $Y_3$ is limited to P, S or Y; and/or $Y_4$ is limited to G, S or K; and/or $Y_5$ is limited to T or absent; and/or $Y_6$ is limited to R or absent; and/or $Y_7$ is limited to N, D or absent; and/or $Y_8$ is limited to G, A, S or Y; and/or $Y_9$ is limited to D, E, A or N; and/or $Y_{10}$ is limited to T or I.

For the VH CDR3, one consensus sequence is VH CDR3 Motif 1:

$$Z_1\ Z_2\ Z_3\ Z_4\ Z_5\ Z_6\ Z_7\ Z_8\ Z_9\ Z_{10}\ Z_{11}\ Z_{12}\ Z_{13}\ Z_{14}\ Z_{15} \quad \text{(SEQ ID NO: 146)}$$

where $Z_1$ is A, G, V, L, I or M; $Z_2$ is R, K, H, C or M; $Z_3$ is G, A, R, K, H, S, T, Y, F, W, D, E or absent; $Z_4$ is Y, F, W, N, Q, G, A, R, K, H or absent; $Z_5$ is S, T, N, Q, E, D or absent; $Z_6$ is D, E or absent; $Z_7$ is L, I, V, M, A, S, T or absent; $Z_8$ is L, I, V, M, A or absent; $Z_9$ is G, A, R, K, H or absent; $Z_{10}$ is I, L, V, M, A, N, Q, R, K, H or absent; $Z_{11}$ is A, M, F, Y, W, S, T, G or absent; $Z_{12}$ is W, Y, F, A, G or absent; $Z_{13}$ is F, Y, W, G, A, M or C; $Z_{14}$ is A, G, M, D, E, W, Y or F; and $Z_{15}$ is Y, F, W, G, A or V. In some embodiments, $Z_1$ is limited to A or V; and/or $Z_2$ is limited to R, K or C; and/or $Z_3$ is limited to G, R, S, Y, D or absent;

and/or $Z_4$ is limited to Y, N, G, R or absent; and/or $Z_5$ is limited to S, N, E or absent; and/or $Z_6$ is limited to D or absent; and/or $Z_7$ is limited to L, S or absent; and/or $Z_8$ is limited to L or absent; and/or $Z_9$ is limited to G, R or absent; and/or $Z_{10}$ is limited to I, N, R, L or absent; and/or $Z_{11}$ is limited to A, F, S, G or absent; and/or $Z_{12}$ is limited to W, Y, A or absent; and/or $Z_{13}$ is limited to F, Y, G or M; and/or $Z_{14}$ is limited to A, D, W or Y; and/or $Z_{15}$ is limited to Y, F, W or G.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter, which is limited only by the claims which follow.

We claim:

1. A cell transformed with a nucleic acid molecule encoding a heavy chain or light chain of an antibody that specifically binds to a human VASA protein comprising an immunoglobulin heavy chain and an immunoglobulin light chain,
   a) wherein the variable region of said light chain comprises:
      (i) a CDR1 region comprising an amino acid sequence selected from the group consisting of SEQ ID NOs: 83-88;
      (ii) a CDR2 region comprising an amino acid sequence selected from the group consisting of SEQ ID NOs: 89-95; and
      (iii) a CDR3 region comprising an amino acid sequence selected from the group consisting of SEQ ID NOs: 96-104; and
   b) wherein the variable region of said heavy chain comprises:
      (i) a CDR1 region comprising an amino acid sequence selected from the group consisting of SEQ ID NOs: 105-112;
      (ii) a CDR2 region comprising an amino acid sequence selected from the group consisting of SEQ ID NOs: 113-121; and
      (iii) a CDR3 region comprising an amino acid sequence selected from the group consisting of SEQ ID NOs: 122-131.

2. The cell of claim 1, wherein said nucleic acid molecule is selected from the group consisting of a cloning vector, an expression vector, a heterologous recombination vector, and a viral integration vector.

3. The cell of claim 1, wherein said cell is a mammalian cell.

4. The cell of claim 3, wherein said cell is a rodent cell.

5. The cell of claim 3, wherein said cell is a Chinese Hamster Ovary (CHO) cell.

6. The cell of claim 3, wherein said cell is a human cell.

* * * * *

SEQUENCE LISTING

```
<160> NUMBER OF SEQ ID NOS: 148

<210> SEQ ID NO 1
<211> LENGTH: 724
<212> TYPE: PRT
<213> ORGANISM: Homo sapiens

<400> SEQUENCE: 1

Met Gly Asp Glu Asp Trp Glu Ala Glu Ile Asn Pro His Met Ser Ser
1               5                   10                  15

Tyr Val Pro Ile Phe Glu Lys Asp Arg Tyr Ser Gly Glu Asn Gly Asp
            20                  25                  30

Asn Phe Asn Arg Thr Pro Ala Ser Ser Ser Glu Met Asp Asp Gly Pro
        35                  40                  45

Ser Arg Arg Asp His Phe Met Lys Ser Gly Phe Ala Ser Gly Arg Asn
    50                  55                  60

Phe Gly Asn Arg Asp Ala Gly Glu Cys Asn Lys Arg Asp Asn Thr Ser
65                  70                  75                  80

Thr Met Gly Gly Phe Gly Val Gly Lys Ser Phe Gly Asn Arg Gly Phe
                85                  90                  95

Ser Asn Ser Arg Phe Glu Asp Gly Asp Ser Ser Gly Phe Trp Arg Glu
            100                 105                 110

Ser Ser Asn Asp Cys Glu Asp Asn Pro Thr Arg Asn Arg Gly Phe Ser
        115                 120                 125

Lys Arg Gly Gly Tyr Arg Asp Gly Asn Asn Ser Glu Ala Ser Gly Pro
    130                 135                 140

Tyr Arg Arg Gly Gly Arg Gly Ser Phe Arg Gly Cys Arg Gly Gly Phe
145                 150                 155                 160

Gly Leu Gly Ser Pro Asn Asn Asp Leu Asp Pro Asp Glu Cys Met Gln
                165                 170                 175

Arg Thr Gly Gly Leu Phe Gly Ser Arg Arg Pro Val Leu Ser Gly Thr
            180                 185                 190

Gly Asn Gly Asp Thr Ser Gln Ser Arg Ser Gly Ser Gly Ser Glu Arg
        195                 200                 205

Gly Gly Tyr Lys Gly Leu Asn Glu Glu Val Ile Thr Gly Ser Gly Lys
    210                 215                 220

Asn Ser Trp Lys Ser Glu Ala Glu Gly Gly Glu Ser Ser Asp Thr Gln
225                 230                 235                 240

Gly Pro Lys Val Thr Tyr Ile Pro Pro Pro Pro Glu Asp Glu Asp
                245                 250                 255

Ser Ile Phe Ala His Tyr Gln Thr Gly Ile Asn Phe Asp Lys Tyr Asp
            260                 265                 270

Thr Ile Leu Val Glu Val Ser Gly His Asp Ala Pro Pro Ala Ile Leu
        275                 280                 285

Thr Phe Glu Glu Ala Asn Leu Cys Gln Thr Leu Asn Asn Asn Ile Ala
    290                 295                 300
```

-continued

```
Lys Ala Gly Tyr Thr Lys Leu Thr Pro Val Gln Lys Tyr Ser Ile Pro
305                 310                 315                 320

Ile Ile Leu Ala Gly Arg Asp Leu Met Ala Cys Ala Gln Thr Gly Ser
                325                 330                 335

Gly Lys Thr Ala Ala Phe Leu Leu Pro Ile Leu Ala His Met Met His
            340                 345                 350

Asp Gly Ile Thr Ala Ser Arg Phe Lys Glu Leu Gln Glu Pro Glu Cys
        355                 360                 365

Ile Ile Val Ala Pro Thr Arg Glu Leu Val Asn Gln Ile Tyr Leu Glu
    370                 375                 380

Ala Arg Lys Phe Ser Phe Gly Thr Cys Val Arg Ala Val Val Ile Tyr
385                 390                 395                 400

Gly Gly Thr Gln Leu Gly His Ser Ile Arg Gln Ile Val Gln Gly Cys
                405                 410                 415

Asn Ile Leu Cys Ala Thr Pro Gly Arg Leu Met Asp Ile Ile Gly Lys
            420                 425                 430

Glu Lys Ile Gly Leu Lys Gln Ile Lys Tyr Leu Val Leu Asp Glu Ala
        435                 440                 445

Asp Arg Met Leu Asp Met Gly Phe Gly Pro Glu Met Lys Lys Leu Ile
    450                 455                 460

Ser Cys Pro Gly Met Pro Ser Lys Glu Gln Arg Gln Thr Leu Met Phe
465                 470                 475                 480

Ser Ala Thr Phe Pro Glu Glu Ile Gln Arg Leu Ala Ala Glu Phe Leu
                485                 490                 495

Lys Ser Asn Tyr Leu Phe Val Ala Val Gly Gln Val Gly Gly Ala Cys
            500                 505                 510

Arg Asp Val Gln Gln Thr Val Leu Gln Val Gly Gln Phe Ser Lys Arg
        515                 520                 525

Glu Lys Leu Val Glu Ile Leu Arg Asn Ile Gly Asp Glu Arg Thr Met
    530                 535                 540

Val Phe Val Glu Thr Lys Lys Lys Ala Asp Phe Ile Ala Thr Phe Leu
545                 550                 555                 560

Cys Gln Glu Lys Ile Ser Thr Thr Ser Ile His Gly Asp Arg Glu Gln
                565                 570                 575

Arg Glu Arg Glu Gln Ala Leu Gly Asp Phe Arg Phe Gly Lys Cys Pro
            580                 585                 590

Val Leu Val Ala Thr Ser Val Ala Ala Arg Gly Leu Asp Ile Glu Asn
        595                 600                 605

Val Gln His Val Ile Asn Phe Asp Leu Pro Ser Thr Ile Asp Glu Tyr
    610                 615                 620

Val His Arg Ile Gly Arg Thr Gly Arg Cys Gly Asn Thr Gly Arg Ala
625                 630                 635                 640

Ile Ser Phe Phe Asp Leu Glu Ser Asp Asn His Leu Ala Gln Pro Leu
                645                 650                 655

Val Lys Val Leu Thr Asp Ala Gln Gln Asp Val Pro Ala Trp Leu Glu
            660                 665                 670

Glu Ile Ala Phe Ser Thr Tyr Ile Pro Gly Phe Ser Gly Ser Thr Arg
        675                 680                 685

Gly Asn Val Phe Ala Ser Val Asp Thr Arg Lys Gly Lys Ser Thr Leu
    690                 695                 700

Asn Thr Ala Gly Phe Ser Ser Gln Ala Pro Asn Pro Val Asp Asp
705                 710                 715                 720

Glu Ser Trp Asp
```

<210> SEQ ID NO 2
<211> LENGTH: 728
<212> TYPE: PRT
<213> ORGANISM: Mus musculus

<400> SEQUENCE: 2

Met Gly Asp Glu Asp Trp Glu Ala Glu Ile Leu Lys Pro His Val Ser
1               5                   10                  15

Ser Tyr Val Pro Val Phe Glu Lys Asp Lys Tyr Ser Ser Gly Ala Asn
            20                  25                  30

Gly Asp Thr Phe Asn Arg Thr Ser Ala Ser Ser Glu Met Glu Asp Gly
        35                  40                  45

Pro Ser Gly Arg Asp Asp Phe Met Arg Ser Gly Phe Pro Ser Gly Arg
50                  55                  60

Ser Leu Gly Ser Arg Asp Ile Gly Glu Ser Ser Lys Lys Glu Asn Thr
65                  70                  75                  80

Ser Thr Thr Gly Gly Phe Gly Arg Gly Lys Gly Phe Gly Asn Arg Gly
                85                  90                  95

Phe Leu Asn Asn Lys Phe Glu Glu Gly Asp Ser Ser Gly Phe Trp Lys
            100                 105                 110

Glu Ser Asn Asn Asp Cys Glu Asp Asn Gln Thr Arg Ser Arg Gly Phe
        115                 120                 125

Ser Lys Arg Gly Gly Cys Gln Asp Gly Asn Asp Ser Glu Ala Ser Gly
130                 135                 140

Pro Phe Arg Arg Gly Gly Arg Gly Ser Phe Arg Gly Cys Arg Gly Gly
145                 150                 155                 160

Phe Gly Leu Gly Arg Pro Asn Ser Glu Ser Asp Gln Asp Gln Gly Thr
                165                 170                 175

Gln Arg Gly Gly Gly Leu Phe Gly Ser Arg Lys Pro Ala Ala Ser Asp
            180                 185                 190

Ser Gly Asn Gly Asp Thr Tyr Gln Ser Arg Ser Gly Ser Gly Arg Gly
        195                 200                 205

Gly Tyr Lys Gly Leu Asn Glu Glu Val Val Thr Gly Ser Gly Lys Asn
210                 215                 220

Ser Trp Lys Ser Glu Thr Glu Gly Gly Glu Ser Ser Asp Ser Gln Gly
225                 230                 235                 240

Pro Lys Val Thr Tyr Ile Pro Pro Pro Glu Asp Glu Asp Ser
                245                 250                 255

Ile Phe Ala His Tyr Gln Thr Gly Ile Asn Phe Asp Lys Tyr Asp Thr
            260                 265                 270

Ile Leu Val Glu Val Ser Gly His Asp Ala Pro Pro Ala Ile Leu Thr
        275                 280                 285

Phe Glu Glu Ala Asn Leu Cys Gln Thr Leu Asn Asn Asn Ile Ala Lys
290                 295                 300

Ala Gly Tyr Thr Lys Leu Thr Pro Val Gln Lys Tyr Ser Ile Pro Ile
305                 310                 315                 320

Val Leu Ala Gly Arg Asp Leu Met Ala Cys Ala Gln Thr Gly Ser Gly
                325                 330                 335

Lys Thr Ala Ala Phe Leu Leu Pro Ile Leu Ala His Met Met Arg Asp
            340                 345                 350

Gly Ile Thr Ala Ser Arg Phe Lys Glu Leu Gln Glu Pro Glu Cys Ile
        355                 360                 365

Ile Val Ala Pro Thr Arg Glu Leu Ile Asn Gln Ile Tyr Leu Glu Ala

```
                    370                 375                 380
Arg Lys Phe Ser Phe Gly Thr Cys Val Arg Ala Val Ile Tyr Gly
385                 390                 395                 400

Gly Thr Gln Phe Gly His Ser Val Arg Gln Ile Val Gln Gly Cys Asn
                405                 410                 415

Ile Leu Cys Ala Thr Pro Gly Arg Leu Met Asp Ile Ile Gly Lys Glu
                420                 425                 430

Lys Ile Gly Leu Lys Gln Val Lys Tyr Leu Val Leu Asp Glu Ala Asp
                435                 440                 445

Arg Met Leu Asp Met Gly Phe Gly Pro Glu Met Lys Lys Leu Ile Ser
450                 455                 460

Cys Pro Gly Met Pro Ser Lys Glu Gln Arg Gln Thr Leu Leu Phe Ser
465                 470                 475                 480

Ala Thr Phe Pro Glu Glu Ile Gln Arg Leu Ala Gly Asp Phe Leu Lys
                485                 490                 495

Ser Ser Tyr Leu Phe Val Ala Val Gly Gln Val Gly Gly Ala Cys Arg
                500                 505                 510

Asp Val Gln Gln Thr Ile Leu Gln Val Gly Gln Tyr Ser Lys Arg Glu
                515                 520                 525

Lys Leu Val Glu Ile Leu Arg Asn Ile Gly Asp Glu Arg Thr Met Val
                530                 535                 540

Phe Val Glu Thr Lys Lys Lys Ala Asp Phe Ile Ala Thr Phe Leu Cys
545                 550                 555                 560

Gln Glu Lys Ile Ser Thr Thr Ser Ile His Gly Asp Arg Glu Gln Arg
                565                 570                 575

Glu Arg Glu Gln Ala Leu Gly Asp Phe Arg Cys Gly Lys Cys Pro Val
                580                 585                 590

Leu Val Ala Thr Ser Val Ala Ala Arg Gly Leu Asp Ile Glu Asn Val
                595                 600                 605

Gln His Val Ile Asn Phe Asp Leu Pro Ser Thr Ile Asp Glu Tyr Val
                610                 615                 620

His Arg Ile Gly Arg Thr Gly Arg Cys Gly Asn Thr Gly Arg Ala Ile
625                 630                 635                 640

Ser Phe Phe Asp Thr Asp Ser Asp Asn His Leu Ala Gln Pro Leu Val
                645                 650                 655

Lys Val Leu Ser Asp Ala Gln Gln Asp Val Pro Ala Trp Leu Glu Glu
                660                 665                 670

Ile Ala Phe Ser Thr Tyr Val Pro Pro Ser Phe Ser Ser Thr Arg
                675                 680                 685

Gly Gly Ala Val Phe Ala Ser Val Asp Thr Arg Lys Asn Tyr Gln Gly
                690                 695                 700

Lys His Thr Leu Asn Thr Ala Gly Ile Ser Ser Ser Gln Ala Pro Asn
705                 710                 715                 720

Pro Val Asp Asp Glu Ser Trp Asp
                725
```

<210> SEQ ID NO 3
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Phe Ile Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Phe Cys Ser Gln Ser
                85                  90                  95

Ala His Val Pro Trp Thr Phe Gly Gly Gly Thr Lys Leu Glu Ile Lys
            100                 105                 110
```

<210> SEQ ID NO 4
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Ser Ile Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Phe Cys Ser Gln Ser
                85                  90                  95

Ala His Val Pro Trp Thr Phe Gly Gly Gly Thr Lys Leu Glu Ile Lys
            100                 105                 110
```

<210> SEQ ID NO 5
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

```
Leu Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80
```

Asn Arg Val Glu Ala Glu Asp Leu Gly Val Tyr Phe Cys Ser Gln Ser
                85                  90                  95

Ala His Val Pro Trp Thr Phe Gly Gly Gly Thr Lys Leu Glu Asp Trp
            100                 105                 110

<210> SEQ ID NO 6
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ser Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Phe Cys Ser Gln Ser
                85                  90                  95

Ala His Val Pro Trp Thr Phe Gly Gly Gly Thr Lys Leu Glu Asp Trp
            100                 105                 110

<210> SEQ ID NO 7
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Tyr Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Phe Cys Ser Gln Ser
                85                  90                  95

Ala His Val Pro Trp Thr Phe Gly Gly Gly Thr Lys Leu Glu Ile Lys
            100                 105                 110

<210> SEQ ID NO 8
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Gln Val Leu Met Thr Gln Ala Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Phe Cys Ser Gln Ser
                85                  90                  95

Ala His Val Pro Trp Thr Phe Gly Gly Gly Thr Lys Leu Glu Ile Lys
            100                 105                 110
```

<210> SEQ ID NO 9
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

```
Arg Phe Gln Val Ser Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Phe Cys Ser Gln Ser
                85                  90                  95

Ala His Val Pro Trp Thr Phe Gly Gly Gly Thr Lys Leu Glu Ile Lys
            100                 105                 110
```

<210> SEQ ID NO 10
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Val Phe Val Met Thr Gln Ala Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
```

```
                65                  70                  75                  80
Asn Arg Val Glu Ala Glu Asp Leu Gly Val Tyr Phe Cys Ser Gln Ser
                    85                  90                  95

Ala His Val Pro Trp Thr Phe Gly Gly Gly Thr Lys Leu Glu Ile Lys
                100                 105                 110

<210> SEQ ID NO 11
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Leu Ile Val Met Thr Gln Ala Pro Leu Ser Leu Pro Val Ser Leu Gly
1               5                   10                  15

Asp Gln Ala Ser Thr Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Phe Cys Ser Gln Ser
                    85                  90                  95

Ala His Val Pro Trp Thr Phe Gly Gly Gly Thr Lys Leu Glu Ile Lys
                100                 105                 110

<210> SEQ ID NO 12
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ser Ile Val Met Thr Gln Ala Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Phe Cys Ser Gln Ser
                    85                  90                  95

Ala His Val Pro Trp Thr Phe Gly Gly Gly Thr Lys Lys Thr Gly Ser
                100                 105                 110

<210> SEQ ID NO 13
<211> LENGTH: 112
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 13

Ser Val Leu Met Thr Gln Thr Pro Leu Ser Leu Pro Val Ser Leu Gly
1               5                   10                  15

Asp Gln Ala Ser Ile Ser Ser Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Gly Gly Thr Lys Leu Glu Ile Lys
            100                 105                 110

<210> SEQ ID NO 14
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Leu Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Leu Thr Phe Gly Gly Gly Thr Lys Leu Glu Ile Lys
            100                 105                 110

<210> SEQ ID NO 15
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Leu Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

```
Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Leu Thr Phe Gly Gly Gly Thr Lys Leu Glu Ile Lys
            100                 105                 110
```

<210> SEQ ID NO 16
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Leu Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Leu Thr Phe Gly Gly Gly Thr Lys Leu Glu Ile Lys
            100                 105                 110
```

<210> SEQ ID NO 17
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Leu Ile Val Met Thr Gln Ala Ala Pro Ser Val Pro Val Thr Pro Gly
1               5                   10                  15

Glu Ser Val Ser Ile Ser Cys Arg Ser Thr Lys Ser Leu Leu His Ser
                20                  25                  30

Asn Gly Asn Thr Tyr Leu Ser Trp Phe Leu Gln Arg Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Ile Lys
            100                 105                 110
```

<210> SEQ ID NO 18
<211> LENGTH: 112
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 18

Tyr Ile Val Met Thr Gln Ala Ala Pro Ser Val Pro Val Thr Pro Gly
1               5                   10                  15

Glu Ser Val Ser Ile Ser Cys Arg Ser Thr Lys Ser Leu Leu His Ser
            20                  25                  30

Asn Gly Asn Thr Tyr Leu Ser Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Ile Lys
            100                 105                 110

<210> SEQ ID NO 19
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ser Gly Leu Met Thr Gln Ala Ala Pro Ser Val Pro Val Thr Pro Gly
1               5                   10                  15

Glu Ser Val Ser Ile Ser Cys Arg Ser Thr Lys Ser Leu Leu His Ser
            20                  25                  30

Asn Gly Asn Thr Tyr Leu Ser Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Leu Lys
            100                 105                 110

<210> SEQ ID NO 20
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Pro Gly Leu Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45
```

```
Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Ile Lys
            100                 105                 110
```

<210> SEQ ID NO 21
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Ser Leu Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Ile Lys
            100                 105                 110
```

<210> SEQ ID NO 22
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Ser Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Gly Asp Val Gly Val Tyr Tyr Cys Met Gln His
                85                  90                  95

Leu Glu Tyr Pro Leu Thr Phe Gly Ala Gly Thr Lys Leu Glu Ile Lys
            100                 105                 110
```

<210> SEQ ID NO 23
<211> LENGTH: 112

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Ile Val Met Thr Gln Ser Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Leu Lys
            100                 105                 110

<210> SEQ ID NO 24
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Val Met Thr Gln Ser Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Leu Lys
            100                 105                 110

<210> SEQ ID NO 25
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Ile Val Leu Thr Gln Ser Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
```

```
                35                  40                  45
Pro Gln Leu Leu Val Tyr Arg Met Ser Asn Leu Ala Ser Gly Val Pro
         50                  55                  60
Asp Arg Phe Ser Gly Ser Gly Ser Gly Thr Ala Phe Thr Leu Arg Ile
 65                  70                  75                  80
Ser Arg Val Glu Ala Glu Asp Val Gly Val Tyr Tyr Cys Met Gln His
                 85                  90                  95
Leu Glu Tyr Pro Leu Thr Phe Gly Ala Gly Thr Lys Leu Glu Leu Lys
                100                 105                 110

<210> SEQ ID NO 26
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Gly Val Met Thr Gln Ser Ala Pro Ser Val Pro Val Thr Pro Gly
 1               5                  10                  15
Glu Ser Val Ser Ile Ser Cys Arg Ser Ser Lys Ser Leu Leu His Ser
                20                  25                  30
Asn Gly Asn Thr Tyr Leu Tyr Trp Phe Leu Gln Arg Pro Gly Gln Ser
                35                  40                  45
Pro Gln Leu Leu Ile Tyr Arg Met Ser Asn Leu Ala Ser Gly Val Pro
         50                  55                  60
Asp Arg Phe Ser Gly Ser Gly Ser Gly Thr Ala Phe Thr Leu Arg Ile
 65                  70                  75                  80
Ser Arg Val Glu Ala Glu Asp Val Gly Val Tyr Tyr Cys Met Gln His
                 85                  90                  95
Leu Glu Tyr Pro Leu Thr Phe Gly Ala Gly Thr Lys Leu Glu Leu Lys
                100                 105                 110

<210> SEQ ID NO 27
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Leu Ile Val Met Thr Gln Ala Ala Pro Ser Val Pro Val Thr Pro Gly
 1               5                  10                  15
Glu Ser Val Ser Ile Ser Cys Arg Ser Ser Lys Ser Leu Leu His Ser
                20                  25                  30
Asn Gly Asn Thr Tyr Leu Tyr Trp Phe Leu Gln Arg Pro Gly Gln Ser
                35                  40                  45
Pro Gln Leu Leu Ile Tyr Arg Met Ser Asn Leu Ala Ser Gly Val Pro
         50                  55                  60
Asp Arg Phe Ser Gly Ser Gly Ser Gly Thr Ala Phe Thr Leu Arg Ile
 65                  70                  75                  80
Ser Arg Val Glu Ala Glu Asp Val Gly Val Tyr Tyr Cys Met Gln His
                 85                  90                  95
Leu Glu Tyr Pro Leu Thr Phe Gly Ala Gly Thr Lys Leu Glu Leu Lys
                100                 105                 110
```

<210> SEQ ID NO 28
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Leu Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Leu Arg
            100                 105                 110
```

<210> SEQ ID NO 29
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

```
Ser Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Leu Lys
            100                 105                 110
```

<210> SEQ ID NO 30
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Val Phe Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30
```

Asn Gly Asn Thr Tyr Leu Tyr Trp Phe Leu Gln Arg Pro Gly Gln Ser
             35                  40                  45

Pro Gln Leu Leu Ile Tyr Arg Met Ser Asn Leu Ala Ser Gly Val Pro
 50                  55                  60

Asp Arg Phe Ser Gly Ser Gly Ser Gly Thr Ala Phe Thr Leu Arg Ile
 65                  70                  75                  80

Ser Arg Val Glu Ala Glu Asp Val Gly Val Tyr Tyr Cys Met Gln His
                 85                  90                  95

Leu Glu Tyr Pro Leu Thr Phe Gly Ala Gly Thr Lys Leu Glu Leu Lys
                100                 105                 110

<210> SEQ ID NO 31
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Ile Val Met Thr Gln Ala Ala Pro Ser Val Pro Val Thr Pro Gly
 1               5                  10                  15

Glu Ser Val Ser Ile Ser Cys Arg Ser Ser Lys Ser Leu Leu His Ser
                 20                  25                  30

Asn Gly Asn Thr Tyr Leu Tyr Trp Phe Leu Gln Arg Pro Gly Gln Ser
             35                  40                  45

Pro Gln Leu Leu Ile Tyr Arg Met Ser Asn Leu Ala Ser Gly Val Pro
 50                  55                  60

Asp Arg Phe Ser Gly Ser Gly Ser Gly Thr Ala Phe Thr Leu Arg Ile
 65                  70                  75                  80

Ser Arg Val Ala Ala Glu Asp Val Gly Val Tyr Tyr Cys Leu Gln Gln
                 85                  90                  95

Leu Glu Tyr Pro Phe Thr Phe Gly Gly Gly Thr Lys Leu Glu Ile Lys
                100                 105                 110

<210> SEQ ID NO 32
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Leu Ile Val Ile Thr Gln Ala Ala Pro Ser Val Pro Val Thr Pro Gly
 1               5                  10                  15

Glu Ser Val Ser Ile Ser Cys Arg Ser Ser Lys Ser Leu Leu His Ser
                 20                  25                  30

Asn Gly Asn Thr Tyr Leu Tyr Trp Phe Leu Gln Arg Pro Gly Gln Ser
             35                  40                  45

Pro Gln Leu Leu Ile Tyr Arg Met Ser Asn Leu Ala Ser Gly Val Pro
 50                  55                  60

Asp Arg Phe Ser Gly Ser Gly Ser Gly Thr Ala Phe Thr Leu Arg Ile
 65                  70                  75                  80

Ser Arg Val Glu Ala Glu Asp Val Gly Val Tyr Tyr Cys Leu Gln Gln
                 85                  90                  95

Leu Glu Tyr Pro Phe Thr Phe Gly Gly Gly Thr Lys Leu Glu Ile Lys
                100                 105                 110

```
<210> SEQ ID NO 33
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asp Ile Val Met Thr Gln Ala Ala Pro Ser Val Ser Val Thr Pro Gly
1               5                   10                  15

Glu Ser Val Ser Ile Ser Cys Arg Ser Thr Lys Ser Leu Leu His Ser
            20                  25                  30

Asn Gly Asn Thr Tyr Leu Tyr Trp Leu Leu Gln Arg Pro Gly Gln Ser
        35                  40                  45

Pro Gln Arg Leu Ile Tyr His Met Ser Asn Leu Ala Ser Gly Val Pro
    50                  55                  60

Asp Arg Phe Ser Gly Arg Gly Ser Gly Thr Asp Phe Thr Leu Arg Ile
65                  70                  75                  80

Ser Arg Val Glu Ala Glu Asp Val Gly Val Tyr Tyr Cys Met Gln Gly
                85                  90                  95

Leu Glu Tyr Pro Leu Thr Phe Gly Ala Gly Thr Lys Leu Glu Leu Lys
            100                 105                 110

<210> SEQ ID NO 34
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Ile Val Met Thr Gln Ala Ala Pro Ser Val Ser Val Thr Pro Gly
1               5                   10                  15

Glu Ser Val Ser Ile Ser Cys Arg Ser Thr Lys Ser Leu Leu His Ser
            20                  25                  30

Asn Gly Asn Thr Tyr Leu Tyr Trp Leu Leu Gln Arg Pro Gly Gln Ser
        35                  40                  45

Pro Gln Arg Leu Ile Tyr His Met Ser Asn Leu Ala Ser Gly Val Pro
    50                  55                  60

Asp Arg Phe Ser Gly Arg Gly Ser Gly Thr Asp Phe Thr Leu Arg Ile
65                  70                  75                  80

Ser Arg Val Glu Ala Glu Asp Val Gly Val Tyr Tyr Cys Met Gln Gly
                85                  90                  95

Leu Glu Tyr Pro Leu Thr Phe Gly Ala Gly Thr Lys Leu Glu Leu Lys
            100                 105                 110

<210> SEQ ID NO 35
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Ile Lys Met Thr Gln Ser Pro Ser Ser Val Phe Ala Ser Leu Gly
1               5                   10                  15
```

```
Glu Arg Val Thr Ile Thr Cys Lys Ala Ser Gln Asn Ile Asn Ser Phe
            20                  25                  30

Leu Thr Trp Phe His Gln Lys Pro Gly Lys Ser Pro Thr Thr Leu Ile
        35                  40                  45

Tyr Arg Thr Asn Arg Leu Leu Asp Gly Val Pro Ser Arg Phe Ser Gly
    50                  55                  60

Ser Gly Ser Gly Gln Asp Tyr Ser Leu Thr Ile Asn Ser Leu Glu Phe
65                  70                  75                  80

Glu Asp Met Gly Ile Tyr Tyr Cys Leu Gln Tyr Asp Asp Phe Pro Leu
                85                  90                  95

Thr Phe Gly Ala Gly Thr Lys Val Glu Leu Lys
            100                 105

<210> SEQ ID NO 36
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Lys Met Thr Gln Ser Pro Ser Ser Val Phe Ala Ser Leu Gly
1               5                   10                  15

Glu Arg Val Thr Ile Thr Cys Lys Ala Ser Gln Asn Ile Asn Ser Phe
            20                  25                  30

Leu Thr Trp Phe His Gln Lys Pro Gly Lys Ser Pro Thr Thr Leu Ile
        35                  40                  45

Tyr Arg Thr Asn Arg Leu Leu Asp Gly Val Pro Ser Arg Phe Ser Gly
    50                  55                  60

Ser Gly Ser Gly Gln Asp Tyr Ser Leu Thr Ile Asn Ser Leu Glu Leu
65                  70                  75                  80

Glu Asp Met Gly Ile Tyr Tyr Cys Leu Gln Tyr Asp Asp Phe Pro Leu
                85                  90                  95

Thr Phe Gly Ala Gly Thr Lys Val Glu Leu Lys
            100                 105

<210> SEQ ID NO 37
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ser Tyr Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ser Ser Tyr Thr Ser Ser Ser
                85                  90                  95
```

```
Ser Trp Val Phe Gly Gly Gly Thr Lys Val Thr Val Leu Gly
            100                 105                 110

<210> SEQ ID NO 38
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ser Tyr Val Leu Thr Gln Pro Pro Ser Val Ser Val Ser Pro Gly Gln
1               5                   10                  15

Thr Ala Ser Val Thr Cys Ser Gly Asp Lys Leu Gly Asn Lys Tyr Ala
            20                  25                  30

Ser Trp Tyr Gln Gln Lys Pro Gly Gln Ser Pro Val Leu Val Ile Tyr
        35                  40                  45

Gln Asp Lys Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Arg Thr Val Val
                85                  90                  95

Ile Gly Arg Gly Thr Lys Leu Thr Val Leu Gly
            100                 105

<210> SEQ ID NO 39
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Leu Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Ala Ile Tyr Pro Gly Asn Gly Asp Thr Arg Tyr Thr Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Gly Gly Ile Ala Trp Phe Ala Tyr Trp Gly Gln Gly Thr Leu
            100                 105                 110

Val Thr Val Ser Ala
        115

<210> SEQ ID NO 40
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 40

Leu Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Ala Ile Tyr Pro Gly Asn Gly Asp Thr Arg Tyr Thr Gln Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Gly Gly Ile Ala Trp Phe Ala Tyr Trp Gly Gln Gly Thr Leu
            100                 105                 110

Val Thr Val Ser Ala
        115

<210> SEQ ID NO 41
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Leu Val Gln Leu Lys Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Ala Ile Tyr Pro Gly Asn Gly Asp Thr Arg Tyr Thr Gln Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Gly Gly Ile Ala Trp Phe Ala Tyr Trp Gly Gln Gly Thr Leu
            100                 105                 110

Val Thr Val Ser Ala
        115

<210> SEQ ID NO 42
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Leu Val Gln Leu Lys Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile

```
            35                  40                  45
Gly Ala Ile Tyr Pro Gly Asn Gly Asp Thr Arg Tyr Thr Gln Lys Phe
        50                  55                  60
Lys Gly Lys Ala Thr Leu Thr Ala Asp Lys Ser Ser Thr Ala Tyr
 65                  70                  75                  80
Met Gln Leu Ser Ser Leu Ala Ser Glu Asp Ser Ala Val Tyr Tyr Cys
                85                  90                  95
Ala Arg Gly Gly Ile Ala Trp Phe Ala Tyr Trp Gly Gln Gly Thr Leu
            100                 105                 110
Val Thr Val Ser Ala
        115

<210> SEQ ID NO 43
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Ser Val Gln Leu Lys Gln Ser Gly Ala Glu Leu Ala Arg Pro Gly Ala
 1               5                  10                  15
Ser Val Lys Leu Ser Cys Lys Ala Ser Gly Tyr Thr Phe Thr Ser Tyr
            20                  25                  30
Trp Met Gln Trp Val Lys Gln Arg Pro Gly Gln Gly Leu Glu Trp Ile
        35                  40                  45
Gly Ala Ile Tyr Pro Gly Asn Gly Asp Thr Arg Tyr Thr Gln Lys Phe
    50                  55                  60
Lys Gly Lys Ala Thr Leu Thr Ala Asp Lys Ser Ser Thr Ala Tyr
 65                  70                  75                  80
Met Gln Leu Ser Ser Leu Ala Ser Glu Asp Ser Ala Val Tyr Tyr Cys
                85                  90                  95
Ala Arg Gly Gly Ile Ala Trp Phe Ala Tyr Trp Gly Gln Gly Thr Leu
            100                 105                 110
Val Thr Val Ser Ala
        115

<210> SEQ ID NO 44
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ser Val Gln Leu Lys Gln Ser Gly Ala Glu Leu Ala Arg Pro Gly Ala
 1               5                  10                  15
Ser Val Lys Leu Ser Cys Lys Ala Ser Gly Tyr Thr Phe Thr Ser Tyr
            20                  25                  30
Trp Met Gln Trp Val Lys Gln Arg Pro Gly Gln Gly Leu Glu Trp Ile
        35                  40                  45
Gly Ala Ile Tyr Pro Gly Asn Gly Asp Thr Arg Tyr Thr Gln Lys Phe
    50                  55                  60
Lys Gly Lys Ala Thr Leu Thr Ala Asp Lys Ser Ser Thr Ala Tyr
 65                  70                  75                  80
Met Gln Leu Ser Ser Leu Ala Ser Glu Asp Ser Ala Val Tyr Tyr Cys
```

```
                85                  90                  95
Ala Arg Gly Gly Ile Ala Trp Phe Ala Tyr Trp Gly Gln Gly Thr Leu
                100                 105                 110

Val Thr Val Ser Ala
        115

<210> SEQ ID NO 45
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Arg Ser Gln Leu Lys Glu Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
                20                  25                  30

Trp Met Gln Trp Val Lys Gln Arg Pro Gly Gln Gly Leu Glu Trp Ile
            35                  40                  45

Gly Ala Ile Tyr Pro Gly Asn Gly Asp Thr Arg Tyr Thr Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Gly Gly Ile Ala Trp Phe Ala Tyr Trp Gly Gln Gly Thr Leu
                100                 105                 110

Val Thr Val Ser Ala
        115

<210> SEQ ID NO 46
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Ser Val Lys Leu Gln Glu Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
                20                  25                  30

Trp Met Gln Trp Val Lys Gln Arg Pro Gly Gln Gly Leu Glu Trp Ile
            35                  40                  45

Gly Ala Ile Tyr Pro Gly Asn Gly Asp Thr Arg Tyr Thr Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Gly Gly Ile Ala Trp Phe Ala Tyr Trp Gly Gln Gly Thr Leu
                100                 105                 110

Val Thr Val Ser Ala
        115
```

<210> SEQ ID NO 47
<211> LENGTH: 117
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 47

```
Ser Val Lys Leu Gln Glu Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Ala Ile Tyr Pro Gly Asn Gly Asp Thr Arg Tyr Thr Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Gly Gly Ile Ala Trp Phe Ala Tyr Trp Gly Gln Gly Thr Leu
            100                 105                 110

Val Thr Val Ser Ala
        115
```

<210> SEQ ID NO 48
<211> LENGTH: 116
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 48

```
Gln Val Gln Leu Gln Pro Ser Gly Ala Glu Leu Ala Arg Pro Gly Ala
1               5                   10                  15

Ser Val Lys Leu Ser Cys Lys Ala Ser Gly Phe Thr Phe Thr Asn Tyr
            20                  25                  30

Trp Met Gln Trp Ile Lys Gln Arg Pro Gly Gln Gly Leu Glu Trp Ile
        35                  40                  45

Gly Ala Ile Tyr Pro Gly Asn Gly Glu Thr Arg His Thr Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Ser Gly Tyr Pro Tyr Phe Ala Tyr Trp Gly Gln Gly Thr Leu Val
            100                 105                 110

Thr Val Ser Ala
        115
```

<210> SEQ ID NO 49
<211> LENGTH: 116
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 49

-continued

```
Gln Val Gln Leu Gln Pro Ser Gly Ala Glu Leu Ala Arg Pro Gly Ala
1               5                   10                  15

Ser Val Lys Leu Ser Cys Lys Ala Ser Gly Phe Thr Phe Thr Asn Tyr
            20                  25                  30

Trp Met Gln Trp Ile Lys Gln Arg Pro Gly Gln Gly Leu Glu Trp Ile
        35                  40                  45

Gly Ala Ile Tyr Pro Gly Asp Gly Glu Thr Arg His Thr Gln Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Ala Ser Glu Asp Ser Ala Val Tyr Tyr Cys
            85                  90                  95

Ala Ser Gly Tyr Pro Tyr Phe Ala Tyr Trp Gly Gln Gly Thr Leu Val
            100                 105                 110

Thr Val Ser Ala
        115

<210> SEQ ID NO 50
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Val Gln Leu Gln Pro Ser Gly Ala Glu Leu Ala Arg Pro Gly Ala
1               5                   10                  15

Pro Val Lys Leu Ser Cys Lys Ala Ser Gly Phe Thr Phe Thr Asn Tyr
            20                  25                  30

Trp Met Gln Trp Ile Lys Gln Arg Pro Gly Gln Gly Leu Glu Trp Ile
        35                  40                  45

Gly Ala Ile Tyr Pro Gly Asp Gly Glu Thr Arg His Thr Gln Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Ala Ser Glu Asp Ser Ala Val Tyr Tyr Cys
            85                  90                  95

Ala Ser Gly Tyr Pro Tyr Phe Ala Tyr Trp Gly Gln Gly Thr Leu Val
            100                 105                 110

Thr Val Ser Ala
        115

<210> SEQ ID NO 51
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Val Gln Leu Gln Pro Ser Gly Ala Glu Leu Ala Arg Pro Gly Ala
1               5                   10                  15

Ser Val Lys Leu Ser Cys Lys Ala Ser Gly Phe Thr Phe Thr Asn Tyr
            20                  25                  30

Trp Met Gln Trp Ile Lys Gln Arg Pro Gly Gln Gly Leu Glu Trp Ile
        35                  40                  45
```

-continued

Gly Ala Ile Tyr Pro Gly Asp Gly Glu Thr Arg His Thr Gln Lys Phe
            50                  55                  60

Lys Gly Lys Ala Thr Leu Ser Ala Asp Lys Ser Ser Ser Thr Ala Tyr
 65                  70                  75                  80

Met Gln Leu Ser Ser Leu Ala Ser Glu Asp Ser Ala Val Tyr Tyr Cys
                 85                  90                  95

Ala Ser Gly Tyr Pro Tyr Phe Ala Tyr Trp Gly Gln Gly Thr Leu Val
            100                 105                 110

Thr Val Ser Ala
        115

<210> SEQ ID NO 52
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Val Gln Leu Lys Glu Ser Gly Ala Glu Leu Ala Arg Pro Gly Ala
 1               5                  10                  15

Ser Val Lys Leu Ser Cys Lys Ala Ser Gly Tyr Thr Phe Thr Ser Tyr
             20                  25                  30

Trp Met Gln Trp Val Lys Gln Arg Pro Gly Gln Gly Leu Glu Trp Ile
         35                  40                  45

Gly Ala Ile Tyr Pro Gly Asn Gly Asp Thr Arg Tyr Thr Gln Lys Phe
     50                  55                  60

Lys Gly Lys Ala Thr Leu Thr Ala Asp Lys Ser Ser Ser Thr Ala Asn
 65                  70                  75                  80

Met Gln Leu Ser Ser Leu Ala Ser Glu Asp Ser Ala Val Tyr Tyr Cys
                 85                  90                  95

Ala Lys Gly Asp Gly Asn Phe Trp Phe Ala Tyr Trp Gly Gln Gly Thr
            100                 105                 110

Leu Val Thr Val Ser Ala
        115

<210> SEQ ID NO 53
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Gln Leu Lys Glu Ser Gly Ala Glu Leu Ala Arg Pro Gly Ala
 1               5                  10                  15

Ser Val Lys Leu Ser Cys Lys Ala Ser Gly Tyr Thr Phe Thr Ser Tyr
             20                  25                  30

Trp Met Gln Trp Val Lys Gln Arg Pro Gly Gln Gly Leu Glu Trp Ile
         35                  40                  45

Gly Ala Ile Tyr Pro Gly Asn Gly Asp Thr Arg Tyr Thr Gln Lys Phe
     50                  55                  60

Lys Gly Lys Ala Thr Leu Thr Ala Asp Lys Ser Ser Ser Thr Ala Asn
 65                  70                  75                  80

Met Gln Leu Ser Ser Leu Ala Ser Glu Asp Ser Ala Val Tyr Tyr Cys
                 85                  90                  95

```
Ala Lys Gly Asp Gly Asn Phe Trp Phe Ala Tyr Trp Gly Gln Gly Thr
            100                 105                 110

Leu Val Thr Val Ser Ala
            115

<210> SEQ ID NO 54
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Val Gln Leu Lys Glu Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Ala Ile Tyr Pro Gly Asn Gly Asp Thr Arg Tyr Thr Gln Lys Phe
    50                  55                  60

Lys Gly Lys Ala Thr Leu Thr Ala Asp Lys Ser Ser Ser Thr Ala Asn
65                  70                  75                  80

Met Gln Leu Ser Gly Leu Ala Ser Glu Asp Ser Ala Val Tyr Tyr Cys
                85                  90                  95

Ala Lys Gly Asp Gly Asn Phe Trp Phe Ala Tyr Trp Gly Gln Gly Thr
            100                 105                 110

Leu Val Thr Val Ser Ala
            115

<210> SEQ ID NO 55
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Val Lys Leu Gln Glu Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Ala Ile Tyr Pro Gly Asn Gly Asp Thr Arg Tyr Thr Gln Lys Phe
    50                  55                  60

Lys Gly Lys Ala Thr Leu Thr Ala Asp Lys Ser Ser Ser Thr Ala Asn
65                  70                  75                  80

Met Gln Leu Ser Ser Leu Ala Ser Glu Asp Ser Ala Val Tyr Tyr Cys
                85                  90                  95

Ala Lys Gly Asp Gly Asn Phe Trp Phe Ala Tyr Trp Gly Gln Gly Thr
            100                 105                 110

Leu Val Thr Val Ser Ala
            115

<210> SEQ ID NO 56
```

```
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Val Gln Leu Gln Gln Ser Gly Ala Glu Leu Ala Arg Pro Gly Ala
1               5                   10                  15

Ser Val Lys Leu Ser Arg Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Ala Ile Tyr Pro Gly Asn Gly Asp Thr Arg Tyr Thr Gln Lys Phe
    50                  55                  60

Lys Gly Lys Ala Thr Leu Thr Ala Asp Lys Ser Ser Thr Ala Asn
65                  70                  75                  80

Met Gln Leu Ser Ser Leu Ala Ser Glu Asp Ser Ala Val Tyr Tyr Cys
                85                  90                  95

Ala Lys Gly Asp Gly Asn Phe Trp Phe Ala Tyr Trp Gly Gln Gly Thr
            100                 105                 110

Leu Val Thr Val Ser Ala
        115

<210> SEQ ID NO 57
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Val Gln Leu Gln Gln Ser Gly Ala Ala Leu Val Arg Pro Gly Ala
1               5                   10                  15

Ser Val Lys Leu Ser Cys Lys Ala Ser Gly Tyr Ser Phe Thr Ser Tyr
            20                  25                  30

Trp Met Asn Trp Val Lys Gln Arg Pro Gly Leu Gly Leu Glu Trp Ile
        35                  40                  45

Gly Met Ile His Pro Ser Asp Ser Glu Thr Arg Leu Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Cys Arg Tyr Asp Arg Ser Tyr Phe Asp Tyr Trp Gly Gln Gly Thr
            100                 105                 110

Thr Leu Thr Val Ser Ser
        115

<210> SEQ ID NO 58
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58
```

```
Glu Val Gln Leu Gln Gln Ser Gly Ala Ala Leu Val Arg Pro Gly Ala
1               5                   10                  15

Ser Val Lys Leu Ser Cys Lys Ala Ser Gly Tyr Ser Phe Thr Ser Tyr
            20                  25                  30

Trp Met Asn Trp Val Lys Gln Arg Pro Gly Leu Gly Leu Glu Trp Ile
        35                  40                  45

Gly Met Ile His Pro Ser Asp Ser Glu Thr Arg Leu Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
            85                  90                  95

Ala Cys Arg Tyr Asp Arg Ser Tyr Phe Asp Tyr Trp Gly Gln Gly Thr
            100                 105                 110

Thr Leu Thr Val Ser Ser
        115

<210> SEQ ID NO 59
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Gln Gln Ser Gly Ala Ala Leu Val Arg Pro Gly Ala
1               5                   10                  15

Ser Val Lys Leu Ser Cys Lys Ala Ser Gly Tyr Ser Phe Thr Ser Tyr
            20                  25                  30

Trp Met Asn Trp Val Lys Gln Arg Pro Gly Leu Gly Leu Glu Trp Ile
        35                  40                  45

Gly Met Ile His Pro Ser Asp Ser Glu Thr Arg Leu Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
            85                  90                  95

Ala Cys Arg Tyr Asp Arg Ser Tyr Phe Asp Tyr Trp Gly Gln Gly Thr
            100                 105                 110

Thr Leu Thr Val Ser Ser
        115

<210> SEQ ID NO 60
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Val Gln Leu Gln Gln Ser Gly Ala Ala Leu Val Arg Pro Gly Ala
1               5                   10                  15

Ser Val Lys Leu Ser Cys Lys Ala Ser Gly Tyr Ser Phe Thr Ser Tyr
            20                  25                  30

Trp Met Asn Trp Val Lys Gln Arg Pro Gly Leu Gly Leu Glu Trp Ile
        35                  40                  45
```

```
Gly Met Ile His Pro Ser Asp Ser Glu Thr Arg Leu Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Cys Arg Tyr Asp Arg Ser Tyr Phe Asp Tyr Trp Gly Gln Gly Thr
                100                 105                 110

Thr Leu Thr Val Ser Ser
            115

<210> SEQ ID NO 61
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Val Gln Leu Gln Gln Ser Gly Ala Ala Leu Val Arg Pro Gly Ala
1               5                   10                  15

Ser Val Lys Leu Ser Cys Lys Ala Ser Gly Tyr Ser Phe Thr Ser Tyr
                20                  25                  30

Trp Met Asn Trp Val Lys Gln Arg Pro Gly Leu Gly Leu Glu Trp Ile
            35                  40                  45

Gly Met Ile His Pro Ser Asp Ser Glu Thr Arg Leu Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Cys Arg Tyr Asp Arg Ser Tyr Phe Asp Tyr Trp Gly Gln Gly Thr
                100                 105                 110

Thr Leu Thr Val Ser Ser
            115

<210> SEQ ID NO 62
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Glu Val Gln Leu Gln Gln Ser Gly Ala Ala Leu Val Arg Pro Gly Ala
1               5                   10                  15

Ser Val Lys Leu Ser Cys Lys Ala Ser Gly Tyr Ser Phe Thr Ser Tyr
                20                  25                  30

Trp Met Asn Trp Val Lys Gln Arg Pro Gly Leu Gly Leu Glu Trp Ile
            35                  40                  45

Gly Met Ile His Pro Ser Asp Ser Glu Thr Arg Leu Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95
```

```
Ala Cys Arg Tyr Asp Arg Ser Tyr Phe Asp Tyr Trp Gly Gln Gly Thr
            100                 105                 110

Thr Leu Thr Val Ser Ser
        115

<210> SEQ ID NO 63
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Arg Val Gln Leu Gln Gln Ser Gly Ala Ala Leu Val Arg Pro Gly Ala
1               5                   10                  15

Ser Val Lys Leu Ser Cys Lys Ala Ser Gly Tyr Ser Phe Thr Ser Tyr
            20                  25                  30

Trp Met Asn Trp Val Lys Gln Arg Pro Gly Leu Gly Leu Glu Trp Ile
        35                  40                  45

Gly Met Ile His Pro Ser Asp Ser Glu Thr Arg Leu Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Cys Arg Tyr Asp Arg Ser Tyr Phe Asp Tyr Trp Gly Gln Gly Thr
            100                 105                 110

Thr Leu Thr Val Ser Ser
        115

<210> SEQ ID NO 64
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Val Gln Leu Lys Gln Ser Gly Ala Ala Leu Val Arg Pro Gly Ala
1               5                   10                  15

Ser Val Lys Leu Ser Cys Lys Ala Ser Gly Tyr Ser Phe Thr Ser Tyr
            20                  25                  30

Trp Met Asn Trp Val Lys Gln Arg Pro Gly Leu Gly Leu Glu Trp Ile
        35                  40                  45

Gly Met Ile His Pro Ser Asp Ser Glu Thr Arg Leu Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Cys Arg Tyr Asp Arg Ser Tyr Phe Asp Tyr Trp Gly Gln Gly Thr
            100                 105                 110

Thr Leu Thr Val Ser Ser
        115

<210> SEQ ID NO 65
<211> LENGTH: 118
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Leu Lys Gln Ser Gly Ala Ala Leu Val Arg Pro Gly Ala
1               5                   10                  15

Ser Val Lys Leu Ser Cys Lys Ala Ser Gly Tyr Ser Phe Thr Ser Tyr
            20                  25                  30

Trp Met Asn Trp Val Lys Gln Arg Pro Gly Leu Gly Leu Glu Trp Ile
        35                  40                  45

Gly Met Ile His Pro Ser Asp Ser Glu Thr Arg Leu Asn Gln Lys Phe
    50                  55                  60

Lys Asp Lys Ala Thr Leu Thr Val Asp Lys Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Cys Arg Tyr Asp Arg Ser Tyr Phe Asp Tyr Trp Gly Gln Gly Thr
            100                 105                 110

Thr Leu Thr Val Ser Ser
            115

<210> SEQ ID NO 66
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Val Gln Leu Gln Gln Pro Gly Ser Glu Phe Val Lys Pro Gly Ala
1               5                   10                  15

Ser Val Arg Leu Ser Arg Lys Ser Ser Gly Tyr Thr Phe Thr Thr Phe
            20                  25                  30

Trp Ile Asn Trp Val Arg Gln Arg Pro Gly Gln Gly Leu Glu Trp Ile
        35                  40                  45

Gly Asn Ile Tyr Pro Gly Asp Ala Ala Thr Arg Phe Asn Glu Lys Phe
    50                  55                  60

Lys Gly Lys Ala Thr Leu Ser Val Asp Thr Ser Ser Thr Thr Ala Tyr
65                  70                  75                  80

Met His Leu Phe Ser Leu Thr Ser Asp Asp Ser Ala Val Tyr Tyr Cys
                85                  90                  95

Val Arg Ser Gly Asp Phe Trp Gly Gln Gly Thr Thr Leu Thr Val Ser
            100                 105                 110

Ser

<210> SEQ ID NO 67
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Val Gln Leu Gln Gln Pro Gly Ser Glu Phe Val Lys Pro Gly Ala
1               5                   10                  15
```

```
Ser Val Arg Leu Ser Cys Lys Ser Gly Tyr Thr Phe Thr Thr Phe
            20                  25                  30

Trp Ile Asn Trp Val Arg Gln Arg Pro Gly Gln Gly Leu Glu Trp Ile
        35                  40                  45

Gly Asn Ile Tyr Pro Gly Asp Ala Ala Thr Arg Phe Asn Glu Lys Phe
50                  55                  60

Lys Gly Lys Ala Thr Leu Ser Val Asp Thr Ser Ser Thr Thr Ala Tyr
65                  70                  75                  80

Met His Leu Phe Ser Leu Thr Ser Asp Asp Ser Ala Val Tyr Tyr Cys
                85                  90                  95

Val Arg Ser Gly Asp Phe Trp Gly Gln Gly Thr Thr Leu Thr Val Ser
            100                 105                 110

Ser

<210> SEQ ID NO 68
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Glu Val Arg Leu Val Glu Thr Gly Gly Gly Leu Val Gln Pro Glu Gly
1               5                   10                  15

Ser Leu Lys Leu Ser Cys Ala Ala Ser Gly Phe Thr Phe Asn Ala Asn
            20                  25                  30

Ala Met Asn Trp Val Arg Gln Val Pro Gly Lys Gly Leu Glu Trp Val
        35                  40                  45

Ala Arg Ile Arg Ser Lys Thr Arg Asn Tyr Ala Ile Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Phe Asn Leu Lys Thr Glu Asp Thr Ala Met Tyr
                85                  90                  95

Tyr Cys Val Arg Asp Gly Trp Trp Gly Gln Gly Thr Ser Val Thr
            100                 105                 110

Val Ser Ser
        115

<210> SEQ ID NO 69
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Glu Val Arg Leu Val Glu Thr Gly Gly Gly Leu Val Gln Pro Glu Gly
1               5                   10                  15

Ser Leu Lys Leu Ser Cys Ala Ala Ser Gly Phe Thr Phe Asn Ala Asn
            20                  25                  30

Ala Met Asn Trp Val Arg Gln Val Pro Gly Lys Gly Leu Glu Trp Val
        35                  40                  45

Ala Arg Ile Arg Ser Lys Thr Arg Asn Tyr Ala Ile Tyr Tyr Ala Asp
    50                  55                  60
```

```
Ser Val Lys Asp Arg Phe Thr Ile Ser Arg Asp Asp Ser Gln Ser Met
 65                  70                  75                  80

Leu Tyr Leu Gln Met Phe Asn Leu Lys Thr Glu Asp Thr Ala Met Tyr
                 85                  90                  95

Tyr Cys Val Arg Asp Gly Trp Trp Trp Gly Gln Gly Thr Ser Val Thr
                100                 105                 110

Val Ser Ser
        115

<210> SEQ ID NO 70
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Leu Val Gln Leu Lys Gln Ser Gly Pro Ser Leu Val Lys Pro Ser Gln
 1               5                  10                  15

Thr Leu Ser Leu Thr Cys Ser Val Thr Gly Asp Ser Val Thr Ser Gly
                 20                  25                  30

Tyr Trp Asn Trp Ile Arg Lys Phe Pro Gly Asn Lys Leu Glu Tyr Met
             35                  40                  45

Gly Tyr Ile Ser Tyr Ser Gly Asn Thr Tyr Tyr Asn Pro Ser Leu Lys
 50                  55                  60

Ser Arg Ile Ser Ile Thr Arg Asp Thr Ser Lys Asn Gln Tyr Tyr Leu
 65                  70                  75                  80

Gln Leu Asn Ser Val Thr Thr Glu Asp Thr Ala Thr Tyr Tyr Cys Ala
                 85                  90                  95

Arg Tyr Asn Ser Leu Leu Arg Leu Gly Ala Met Asp Tyr Trp Gly Gln
                100                 105                 110

Gly Thr Ser Val Thr Val Ser Ser
        115                 120

<210> SEQ ID NO 71
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Leu Val Gln Leu Lys Gln Ser Gly Pro Ser Leu Val Lys Pro Ser Gln
 1               5                  10                  15

Thr Leu Ser Leu Thr Cys Ser Val Thr Gly Asp Ser Val Thr Ser Gly
                 20                  25                  30

Tyr Trp Asn Trp Ile Arg Lys Phe Pro Gly Asn Lys Leu Glu Tyr Met
             35                  40                  45

Gly Tyr Ile Ser Tyr Ser Gly Asn Thr Tyr Tyr Asn Pro Ser Leu Lys
 50                  55                  60

Ser Arg Ile Ser Ile Thr Arg Asp Thr Ser Lys Asn Gln Tyr Tyr Leu
 65                  70                  75                  80

Gln Leu Asn Ser Val Thr Thr Glu Asp Thr Ala Thr Tyr Tyr Cys Ala
                 85                  90                  95

Arg Tyr Asn Ser Leu Leu Arg Leu Gly Ala Met Asp Tyr Trp Gly Gln
                100                 105                 110
```

```
Gly Thr Ser Val Thr Val Ser Ser
        115                 120
```

<210> SEQ ID NO 72
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

```
Leu Val Gln Leu Lys Glu Ser Gly Pro Ser Leu Val Lys Pro Ser Gln
1               5                   10                  15

Thr Leu Ser Leu Thr Cys Ser Val Thr Gly Asp Ser Val Thr Ser Gly
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Asn Thr Tyr Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Asn Ser Leu Leu Arg Leu Gly Ala Met Asp Tyr Trp Gly Gln
            100                 105                 110

Gly Thr Ser Val Thr Val Ser Ser
        115                 120
```

<210> SEQ ID NO 73
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

```
Ser Val Gln Leu Lys Glu Ser Gly Pro Ser Leu Val Lys Pro Ser Gln
1               5                   10                  15

Thr Leu Ser Leu Thr Cys Ser Val Thr Gly Asp Ser Val Thr Ser Gly
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Asn Thr Tyr Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Asn Ser Leu Leu Arg Leu Gly Ala Met Asp Tyr Trp Gly Gln
            100                 105                 110

Gly Thr Ser Val Thr Val Ser Ser
        115                 120
```

<210> SEQ ID NO 74
<211> LENGTH: 120
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 74

Asp Val Lys Leu Gln Glu Ser Gly Pro Ser Leu Val Lys Pro Ser Gln
1               5                   10                  15

Thr Leu Ser Leu Thr Cys Ser Val Thr Gly Asp Ser Val Thr Ser Gly
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Asn Thr Tyr Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Asn Ser Leu Leu Arg Leu Gly Ala Met Asp Tyr Trp Gly Gln
            100                 105                 110

Gly Thr Ser Val Thr Val Ser Ser
        115                 120

<210> SEQ ID NO 75
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Asp Val Lys Leu Gln Glu Ser Gly Pro Ser Leu Val Lys Pro Ser Gln
1               5                   10                  15

Thr Leu Ser Leu Thr Cys Ser Val Thr Gly Asp Ser Val Thr Ser Gly
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Asn Thr Tyr Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Asn Ser Leu Leu Arg Leu Gly Ala Met Asp Tyr Trp Gly Gln
            100                 105                 110

Gly Thr Ser Val Thr Val Ser Ser
        115                 120

<210> SEQ ID NO 76
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Leu Val Lys Leu Gln Glu Ser Gly Pro Ser Leu Val Lys Pro Ser Gln
1               5                   10                  15

Thr Leu Ser Leu Thr Cys Ser Val Thr Gly Asp Ser Val Thr Ser Gly

```
                    20                  25                  30

Tyr Trp Asn Trp Ile Arg Lys Phe Pro Gly Asn Lys Leu Glu Tyr Met
                35                  40                  45

Gly Tyr Ile Ser Tyr Ser Gly Asn Thr Tyr Tyr Asn Pro Ser Leu Lys
            50                  55                  60

Ser Arg Ile Ser Ile Thr Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Asn Ser Leu Leu Arg Leu Gly Ala Met Asp Tyr Trp Gly Gln
                100                 105                 110

Gly Thr Ser Val Thr Val Ser Ser
        115                 120

<210> SEQ ID NO 77
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Val Lys Leu Val Glu Ser Gly Pro Ser Leu Val Lys Pro Ser Gln
1               5                   10                  15

Thr Leu Ser Leu Thr Cys Ser Val Thr Gly Asp Ser Val Thr Ser Gly
                20                  25                  30

Tyr Trp Asn Trp Ile Arg Lys Phe Pro Gly Asn Lys Leu Glu Tyr Met
                35                  40                  45

Gly Tyr Ile Ser Tyr Ser Gly Asn Thr Tyr Tyr Asn Pro Ser Leu Lys
            50                  55                  60

Ser Arg Ile Ser Ile Thr Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Asn Ser Leu Leu Arg Leu Gly Ala Met Asp Tyr Trp Gly Gln
                100                 105                 110

Gly Thr Ser Val Thr Val Ser Ser
        115                 120

<210> SEQ ID NO 78
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Glu Val Lys Leu Val Glu Ser Gly Pro Ser Leu Val Lys Pro Ser Gln
1               5                   10                  15

Thr Leu Ser Leu Thr Cys Ser Val Thr Gly Asp Ser Val Thr Ser Gly
                20                  25                  30

Tyr Trp Asn Trp Ile Arg Lys Phe Pro Gly Asn Lys Leu Glu Tyr Met
                35                  40                  45

Gly Tyr Ile Ser Tyr Ser Gly Asn Thr Tyr Tyr Asn Pro Ser Leu Lys
            50                  55                  60

Ser Arg Ile Ser Ile Thr Arg Asp Thr Ser Lys Asn Gln Tyr Tyr Leu
```

```
                65                  70                  75                  80
Gln Leu Asn Ser Val Thr Thr Glu Asp Thr Ala Thr Tyr Tyr Cys Ala
                    85                  90                  95

Arg Tyr Asn Ser Leu Leu Arg Leu Gly Ala Met Asp Tyr Trp Gly Gln
                100                 105                 110

Gly Thr Ser Val Thr Val Ser Ser
            115                 120

<210> SEQ ID NO 79
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Val Lys Leu Val Glu Ser Gly Pro Ser Leu Val Lys Pro Ser Gln
1               5                   10                  15

Thr Leu Ser Leu Thr Cys Ser Val Thr Gly Asp Ser Val Thr Ser Gly
                20                  25                  30

Tyr Trp Asn Trp Ile Arg Lys Phe Pro Gly Asn Lys Leu Glu Tyr Met
            35                  40                  45

Gly Tyr Ile Ser Tyr Ser Gly Asn Thr Tyr Asn Pro Ser Leu Lys
        50                  55                  60

Ser Arg Ile Ser Ile Thr Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                    85                  90                  95

Arg Tyr Asn Ser Leu Leu Arg Leu Gly Ala Met Asp Tyr Trp Gly Gln
                100                 105                 110

Gly Thr Ser Val Thr Val Ser Ser
            115                 120

<210> SEQ ID NO 80
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gln Val Gln Leu Gln Gln Ser Gly Gly Gly Leu Val Lys Pro Gly Gly
1               5                   10                  15

Ser Leu Arg Leu Ser Cys Thr Ala Ser Gly Phe Thr Phe Ser Ser Tyr
                20                  25                  30

Trp Met Thr Trp Val Arg Gln Ala Pro Gly Lys Gly Leu Glu Trp Val
            35                  40                  45

Ala Asn Ile Lys Arg Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                    85                  90                  95

Ala Arg Gly Gly Asn Ser Tyr Tyr Gly Trp Gly Gln Gly Thr Leu Val
                100                 105                 110

Thr Val Ser Ser
```

<210> SEQ ID NO 81
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Val Gln Leu Gln Gln Ser Gly Gly Gly Leu Val Lys Pro Gly Gly
1               5                   10                  15

Ser Leu Arg Leu Ser Cys Thr Ala Ser Gly Phe Thr Phe Ser Ser Tyr
            20                  25                  30

Trp Met Thr Trp Val Arg Gln Ala Pro Gly Lys Gly Leu Glu Trp Val
        35                  40                  45

Ala Asn Ile Lys Arg Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asn Ser Phe Arg Asp Trp Gly Gln Gly Thr Leu Val
            100                 105                 110

Thr Val Ser Ser
        115

<210> SEQ ID NO 82
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gln Val Asn Leu Arg Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Ala Ile Ser Tyr Asp Gly Ile Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Glu Asp Gly Met Asp Val Trp Gly Gln Gly Thr Thr
            100                 105                 110

Val Thr Val Ser Ala
        115

<210> SEQ ID NO 83
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 83

Gln Ser Leu Val His Ser Asn Gly Asn Thr Tyr
1               5                   10

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gln Asn Ile Val His Ser Asn Gly Asn Thr Tyr
1               5                   10

<210> SEQ ID NO 85
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Lys Ser Leu Leu His Ser Asn Gly Asn Thr Tyr
1               5                   10

<210> SEQ ID NO 86
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln Asn Ile Asn Ser Phe
1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ser Asn Ile Gly Asn Asn Tyr
1               5

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Lys Leu Gly Asn Lys Tyr
1               5

<210> SEQ ID NO 89

```
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Lys Val Ser
1

<210> SEQ ID NO 90
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Lys Ile Ser
1

<210> SEQ ID NO 91
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Met Ser
1

<210> SEQ ID NO 92
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

His Met Ser
1

<210> SEQ ID NO 93
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Arg Thr Asn
1

<210> SEQ ID NO 94
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94
```

```
Asp Asn Asn
1

<210> SEQ ID NO 95
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gln Asp Lys
1

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ser Gln Ser Ala His Val Pro Trp Thr
1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ser Gln Ser Thr His Val Pro Pro Thr
1               5

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Phe Gln Gly Ser His Val Leu Thr
1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Met Gln His Leu Glu Tyr Pro Leu Thr
1               5

<210> SEQ ID NO 100
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 100

Leu Gln Gln Leu Glu Tyr Pro Phe Thr
1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Met Gln Gly Leu Glu Tyr Pro Leu Thr
1               5

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Leu Gln Tyr Asp Asp Phe Pro Leu Thr
1               5

<210> SEQ ID NO 103
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ser Ser Tyr Thr Ser Ser Ser Ser Trp Val
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gln Ala Trp Asp Ser Arg Thr Val Val Ile
1               5                   10

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Tyr Thr Phe Thr Ser Tyr Trp
1               5

```
<210> SEQ ID NO 106
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Phe Thr Phe Thr Asn Tyr Trp
1               5

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Tyr Ser Phe Thr Ser Tyr Trp
1               5

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Tyr Thr Phe Thr Thr Phe Trp
1               5

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Phe Thr Phe Asn Ala Asn Ala
1               5

<210> SEQ ID NO 110
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Asp Ser Val Thr Ser Gly Tyr
1               5

<210> SEQ ID NO 111
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111
```

```
Gly Phe Thr Phe Ser Ser Tyr Trp
1               5

<210> SEQ ID NO 112
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Phe Thr Phe Ser Asn Tyr Gly
1               5

<210> SEQ ID NO 113
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ile Tyr Pro Gly Asn Gly Asp Thr
1               5

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ile Tyr Pro Gly Asn Gly Glu Thr
1               5

<210> SEQ ID NO 115
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ile Tyr Pro Gly Asp Gly Glu Thr
1               5

<210> SEQ ID NO 116
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ile His Pro Ser Asp Ser Glu Thr
1               5

<210> SEQ ID NO 117
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 117

Ile Tyr Pro Gly Asp Ala Ala Thr
1               5

<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ile Arg Ser Lys Thr Arg Asn Tyr Ala Ile
1               5                   10

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ile Ser Tyr Ser Gly Asn Thr
1               5

<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ile Lys Arg Asp Gly Ser Glu Lys
1               5

<210> SEQ ID NO 121
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ile Ser Tyr Asp Gly Ile Asn Lys
1               5

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ala Arg Gly Gly Ile Ala Trp Phe Ala Tyr
1               5                   10
```

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ala Ser Gly Tyr Pro Tyr Phe Ala Tyr
1               5

<210> SEQ ID NO 124
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ala Lys Gly Asp Gly Asn Phe Trp Phe Ala Tyr
1               5                   10

<210> SEQ ID NO 125
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ala Cys Arg Tyr Asp Arg Ser Tyr Phe Asp Tyr
1               5                   10

<210> SEQ ID NO 126
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Val Arg Ser Gly Asp Phe
1               5

<210> SEQ ID NO 127
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Val Arg Asp Gly Trp Trp
1               5

<210> SEQ ID NO 128
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 128

Ala Arg Tyr Asn Ser Leu Leu Arg Leu Gly Ala Met Asp Tyr
1               5                   10

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ala Arg Gly Gly Asn Ser Tyr Tyr Gly
1               5

<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ala Arg Gly Gly Asn Ser Phe Arg Asp
1               5

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ala Lys Asp Arg Glu Asp Gly Met Asp Val
1               5                   10

<210> SEQ ID NO 132
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln, Asn, Lys, Arg, Ser or Thr
<220> FEATURE:
<221> NAME/KEY: MOD_RES
<222> LOCATION: (2)..(2)
<223> OTHER INFORMATION: Ser, Thr, Cys, Asn or Gln
<220> FEATURE:
<221> NAME/KEY: MOD_RES
<222> LOCATION: (3)..(3)
<223> OTHER INFORMATION: Ile, Leu, Val, Met or Ala
<220> FEATURE:
<221> NAME/KEY: MOD_RES
<222> LOCATION: (4)..(4)
<223> OTHER INFORMATION: Val, Leu, Ile, Met, Ala or absent
<220> FEATURE:
<221> NAME/KEY: MOD_RES
<222> LOCATION: (5)..(5)
<223> OTHER INFORMATION: His, Lys, Arg or absent
<220> FEATURE:
<221> NAME/KEY: MOD_RES
<222> LOCATION: (6)..(6)
<223> OTHER INFORMATION: Ser, Thr, Cys or absent
```

```
<220> FEATURE:
<221> NAME/KEY: MOD_RES
<222> LOCATION: (7)..(7)
<223> OTHER INFORMATION: Asn, Gln or absent
<220> FEATURE:
<221> NAME/KEY: MOD_RES
<222> LOCATION: (8)..(8)
<223> OTHER INFORMATION: Gly, Ala or absent
<220> FEATURE:
<221> NAME/KEY: MOD_RES
<222> LOCATION: (9)..(9)
<223> OTHER INFORMATION: Asn or Gln
<220> FEATURE:
<221> NAME/KEY: MOD_RES
<222> LOCATION: (10)..(10)
<223> OTHER INFORMATION: Thr, Ser, Cys, Asn or Gln
<220> FEATURE:
<221> NAME/KEY: MOD_RES
<222> LOCATION: (11)..(11)
<223> OTHER INFORMATION: Tyr, Phe or Trp
<220> FEATURE:
<223> OTHER INFORMATION: see specification as filed for detailed
      description of substitutions and preferred embodiments

<400> SEQUENCE: 132

Xaa Xaa Xaa Xaa Xaa Xaa Xaa Xaa Xaa Xaa Xaa
1               5                   10

<210> SEQ ID NO 133
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln, Asn, Lys or Arg
<220> FEATURE:
<221> NAME/KEY: MOD_RES
<222> LOCATION: (2)..(2)
<223> OTHER INFORMATION: Ser, Thr, Cys, Asn or Gln
<220> FEATURE:
<221> NAME/KEY: MOD_RES
<222> LOCATION: (3)..(3)
<223> OTHER INFORMATION: Ile, Leu, Val, Met or Ala
<220> FEATURE:
<221> NAME/KEY: MOD_RES
<222> LOCATION: (4)..(4)
<223> OTHER INFORMATION: Val, Leu, Ile, Met or Ala
<220> FEATURE:
<221> NAME/KEY: MOD_RES
<222> LOCATION: (5)..(5)
<223> OTHER INFORMATION: His, Lys or Arg
<220> FEATURE:
<221> NAME/KEY: MOD_RES
<222> LOCATION: (6)..(6)
<223> OTHER INFORMATION: Ser, Thr or Cys
<220> FEATURE:
<221> NAME/KEY: MOD_RES
<222> LOCATION: (7)..(7)
<223> OTHER INFORMATION: Asn or Gln
<220> FEATURE:
<221> NAME/KEY: MOD_RES
<222> LOCATION: (8)..(8)
<223> OTHER INFORMATION: Gly or Ala
<220> FEATURE:
<221> NAME/KEY: MOD_RES
<222> LOCATION: (9)..(9)
<223> OTHER INFORMATION: Asn or Gln
<220> FEATURE:
<221> NAME/KEY: MOD_RES
<222> LOCATION: (10)..(10)
<223> OTHER INFORMATION: Thr, Ser or Cys
<220> FEATURE:
<221> NAME/KEY: MOD_RES
```

```
<222> LOCATION: (11)..(11)
<223> OTHER INFORMATION: Tyr, Phe or Trp
<220> FEATURE:
<223> OTHER INFORMATION: see specification as filed for detailed
      description of substitutions and preferred embodiments

<400> SEQUENCE: 133

Xaa Xaa Xaa Xaa Xaa Xaa Xaa Xaa Xaa Xaa Xaa
1               5                   10

<210> SEQ ID NO 134
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Arg or His
<220> FEATURE:
<221> NAME/KEY: MOD_RES
<222> LOCATION: (2)..(2)
<223> OTHER INFORMATION: Val, Ile, Leu, Met, Ala, Thr, Ser or Cys
<220> FEATURE:
<221> NAME/KEY: MOD_RES
<222> LOCATION: (3)..(3)
<223> OTHER INFORMATION: Ser, Thr, Cys, Asn or Gln
<220> FEATURE:
<223> OTHER INFORMATION: see specification as filed for detailed
      description of substitutions and preferred embodiments

<400> SEQUENCE: 134

Xaa Xaa Xaa
1

<210> SEQ ID NO 135
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp or Glu
<220> FEATURE:
<221> NAME/KEY: MOD_RES
<222> LOCATION: (2)..(2)
<223> OTHER INFORMATION: Asn or Gln
<220> FEATURE:
<221> NAME/KEY: MOD_RES
<222> LOCATION: (3)..(3)
<223> OTHER INFORMATION: Asn or Gln

<400> SEQUENCE: 135

Xaa Xaa Xaa
1

<210> SEQ ID NO 136
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln or Asn
<220> FEATURE:
```

```
<221> NAME/KEY: MOD_RES
<222> LOCATION: (2)..(2)
<223> OTHER INFORMATION: Asp or Glu
<220> FEATURE:
<221> NAME/KEY: MOD_RES
<222> LOCATION: (3)..(3)
<223> OTHER INFORMATION: Lys, Arg or His
<220> FEATURE:
<223> OTHER INFORMATION: see specification as filed for detailed
      description of substitutions and preferred embodiments

<400> SEQUENCE: 136

Xaa Xaa Xaa
1

<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, Thr, Cys, Phe, Tyr, Met, Leu, Val, Ile or
      Ala
<220> FEATURE:
<221> NAME/KEY: MOD_RES
<222> LOCATION: (2)..(2)
<223> OTHER INFORMATION: Gln, Asn, Ser, Thr or Cys
<220> FEATURE:
<221> NAME/KEY: MOD_RES
<222> LOCATION: (3)..(3)
<223> OTHER INFORMATION: Ser, Thr, Cys, Gly, Ala, His, Lys, Arg, Gln,
      Asn, Tyr, Phe or Trp
<220> FEATURE:
<221> NAME/KEY: MOD_RES
<222> LOCATION: (4)..(4)
<223> OTHER INFORMATION: Ala, Gly, Ser, Thr, Cys, Leu, Ile, Val, Met,
      Asp or Glu
<220> FEATURE:
<221> NAME/KEY: MOD_RES
<222> LOCATION: (5)..(5)
<223> OTHER INFORMATION: His, Lys, Arg, Glu, Asp, Ser, Thr or Cys
<220> FEATURE:
<221> NAME/KEY: MOD_RES
<222> LOCATION: (6)..(6)
<223> OTHER INFORMATION: Val, Leu, Ile, Met, Ala, Tyr, Phe, Trp, Ser,
      Thr or Cys
<220> FEATURE:
<221> NAME/KEY: MOD_RES
<222> LOCATION: (7)..(7)
<223> OTHER INFORMATION: Pro, Ser, Thr, Cys or absent
<220> FEATURE:
<221> NAME/KEY: MOD_RES
<222> LOCATION: (8)..(8)
<223> OTHER INFORMATION: Ser, Thr, Cys or absent
<220> FEATURE:
<221> NAME/KEY: MOD_RES
<222> LOCATION: (9)..(9)
<223> OTHER INFORMATION: Trp, Pro, Leu, Ile, Val, Met, Ala, Phe or Tyr
<220> FEATURE:
<221> NAME/KEY: MOD_RES
<222> LOCATION: (10)..(10)
<223> OTHER INFORMATION: Thr, Ser, Cys, Val, Leu, Ile, Met or Ala
<220> FEATURE:
<223> OTHER INFORMATION: see specification as filed for detailed
      description of substitutions and preferred embodiments

<400> SEQUENCE: 137

Xaa Xaa Xaa Xaa Xaa Xaa Xaa Xaa Xaa Xaa
1               5                   10

<210> SEQ ID NO 138
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, Thr, Cys, Phe or Tyr
<220> FEATURE:
<221> NAME/KEY: MOD_RES
<222> LOCATION: (2)..(2)
<223> OTHER INFORMATION: Gln or Asn
<220> FEATURE:
<221> NAME/KEY: MOD_RES
<222> LOCATION: (3)..(3)
<223> OTHER INFORMATION: Ser, Thr, Cys, Gly or Ala
<220> FEATURE:
<221> NAME/KEY: MOD_RES
<222> LOCATION: (4)..(4)
<223> OTHER INFORMATION: Ala, Gly, Ser, Thr or Cys
<220> FEATURE:
<221> NAME/KEY: MOD_RES
<222> LOCATION: (5)..(5)
<223> OTHER INFORMATION: His, Lys or Arg
<220> FEATURE:
<221> NAME/KEY: MOD_RES
<222> LOCATION: (6)..(6)
<223> OTHER INFORMATION: Val, Leu, Ile, Met or Ala
<220> FEATURE:
<221> NAME/KEY: MOD_RES
<222> LOCATION: (7)..(7)
<223> OTHER INFORMATION: Pro or absent
<220> FEATURE:
<221> NAME/KEY: MOD_RES
<222> LOCATION: (8)..(8)
<223> OTHER INFORMATION: Trp, Pro, Leu, Ile, Val, Met, Ala, Phe or Tyr
<220> FEATURE:
<221> NAME/KEY: MOD_RES
<222> LOCATION: (9)..(9)
<223> OTHER INFORMATION: Thr, Ser or Cys
<220> FEATURE:
<223> OTHER INFORMATION: see specification as filed for detailed
      description of substitutions and preferred embodiments

<400> SEQUENCE: 138

Xaa Xaa Xaa Xaa Xaa Xaa Xaa Xaa Xaa
1               5

<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Met, Cys, Leu, Ile, Val or Ala
<220> FEATURE:
<221> NAME/KEY: MOD_RES
<222> LOCATION: (2)..(2)
<223> OTHER INFORMATION: Gln or Asn
<220> FEATURE:
<221> NAME/KEY: MOD_RES
<222> LOCATION: (3)..(3)
<223> OTHER INFORMATION: His, Lys, Arg, Gln, Asn, Gly, Ala, Tyr or Phe
<220> FEATURE:
<221> NAME/KEY: MOD_RES
<222> LOCATION: (4)..(4)
<223> OTHER INFORMATION: Leu, Ile, Val, Met, Ala, Asp or Glu
<220> FEATURE:
<221> NAME/KEY: MOD_RES
<222> LOCATION: (5)..(5)
<223> OTHER INFORMATION: Glu or Asp
```

```
<220> FEATURE:
<221> NAME/KEY: MOD_RES
<222> LOCATION: (6)..(6)
<223> OTHER INFORMATION: Tyr or Phe
<220> FEATURE:
<221> NAME/KEY: MOD_RES
<222> LOCATION: (8)..(8)
<223> OTHER INFORMATION: Trp, Pro, Leu, Ile, Val, Met, Ala, Phe or Tyr
<220> FEATURE:
<221> NAME/KEY: MOD_RES
<222> LOCATION: (9)..(9)
<223> OTHER INFORMATION: Thr, Ser or Cys
<220> FEATURE:
<223> OTHER INFORMATION: see specification as filed for detailed
      description of substitutions and preferred embodiments

<400> SEQUENCE: 139

Xaa Xaa Xaa Xaa Xaa Xaa Pro Xaa Xaa
1               5

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, Thr or Cys
<220> FEATURE:
<221> NAME/KEY: MOD_RES
<222> LOCATION: (2)..(2)
<223> OTHER INFORMATION: Ser, Thr or Cys
<220> FEATURE:
<221> NAME/KEY: MOD_RES
<222> LOCATION: (3)..(3)
<223> OTHER INFORMATION: Tyr or Phe
<220> FEATURE:
<221> NAME/KEY: MOD_RES
<222> LOCATION: (4)..(4)
<223> OTHER INFORMATION: Thr, Ser or Cys
<220> FEATURE:
<221> NAME/KEY: MOD_RES
<222> LOCATION: (5)..(5)
<223> OTHER INFORMATION: Ser, Thr or Cys
<220> FEATURE:
<221> NAME/KEY: MOD_RES
<222> LOCATION: (6)..(6)
<223> OTHER INFORMATION: Ser, Thr or Cys
<220> FEATURE:
<221> NAME/KEY: MOD_RES
<222> LOCATION: (7)..(7)
<223> OTHER INFORMATION: Ser, Thr or Cys
<220> FEATURE:
<221> NAME/KEY: MOD_RES
<222> LOCATION: (8)..(8)
<223> OTHER INFORMATION: Ser, Thr or Cys
<220> FEATURE:
<221> NAME/KEY: MOD_RES
<222> LOCATION: (9)..(9)
<223> OTHER INFORMATION: Trp, Pro, Phe or Tyr
<220> FEATURE:
<221> NAME/KEY: MOD_RES
<222> LOCATION: (10)..(10)
<223> OTHER INFORMATION: Val, Leu, Ile, Met, Ala, Thr, Ser or Cys
<220> FEATURE:
<223> OTHER INFORMATION: see specification as filed for detailed
      description of substitutions and preferred embodiments

<400> SEQUENCE: 140

Xaa Xaa Xaa Xaa Xaa Xaa Xaa Xaa Xaa Xaa
1               5                   10
```

```
<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln or Asn
<220> FEATURE:
<221> NAME/KEY: MOD_RES
<222> LOCATION: (2)..(2)
<223> OTHER INFORMATION: Ala or Gly
<220> FEATURE:
<221> NAME/KEY: MOD_RES
<222> LOCATION: (3)..(3)
<223> OTHER INFORMATION: Trp, Tyr or Phe
<220> FEATURE:
<221> NAME/KEY: MOD_RES
<222> LOCATION: (4)..(4)
<223> OTHER INFORMATION: Asp or Glu
<220> FEATURE:
<221> NAME/KEY: MOD_RES
<222> LOCATION: (5)..(5)
<223> OTHER INFORMATION: Ser, Thr or Cys
<220> FEATURE:
<221> NAME/KEY: MOD_RES
<222> LOCATION: (6)..(6)
<223> OTHER INFORMATION: Arg, Lys or His
<220> FEATURE:
<221> NAME/KEY: MOD_RES
<222> LOCATION: (7)..(7)
<223> OTHER INFORMATION: Thr, Ser or Cys
<220> FEATURE:
<221> NAME/KEY: MOD_RES
<222> LOCATION: (8)..(8)
<223> OTHER INFORMATION: Val, Ile, Leu, Met or Ala
<220> FEATURE:
<221> NAME/KEY: MOD_RES
<222> LOCATION: (9)..(9)
<223> OTHER INFORMATION: Val, Ile, Leu, Met or Ala
<220> FEATURE:
<221> NAME/KEY: MOD_RES
<222> LOCATION: (10)..(10)
<223> OTHER INFORMATION: Ile, Leu, Val, Met or Ala
<220> FEATURE:
<223> OTHER INFORMATION: see specification as filed for detailed
      description of substitutions and preferred embodiments

<400> SEQUENCE: 141

Xaa Xaa Xaa Xaa Xaa Xaa Xaa Xaa Xaa Xaa
1               5                   10

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly or Ala
<220> FEATURE:
<221> NAME/KEY: MOD_RES
<222> LOCATION: (2)..(2)
<223> OTHER INFORMATION: Tyr, Phe, Trp, Asp or Glu
<220> FEATURE:
<221> NAME/KEY: MOD_RES
<222> LOCATION: (3)..(3)
<223> OTHER INFORMATION: Thr, Ser, Cys or Met
<220> FEATURE:
<221> NAME/KEY: MOD_RES
<222> LOCATION: (4)..(4)
```

```
<223> OTHER INFORMATION: Phe, Tyr, Trp, Val, Leu, Ile, Met or Ala
<220> FEATURE:
<221> NAME/KEY: MOD_RES
<222> LOCATION: (5)..(5)
<223> OTHER INFORMATION: Thr, Ser, Cys, Asn or Gln
<220> FEATURE:
<221> NAME/KEY: MOD_RES
<222> LOCATION: (6)..(6)
<223> OTHER INFORMATION: Ser, Thr, Cys, Ala or Gly
<220> FEATURE:
<221> NAME/KEY: MOD_RES
<222> LOCATION: (7)..(7)
<223> OTHER INFORMATION: Tyr, Phe, Trp, Asn, Gln, Gly or Ala
<220> FEATURE:
<221> NAME/KEY: MOD_RES
<222> LOCATION: (8)..(8)
<223> OTHER INFORMATION: Trp, Ala, Gly, Tyr or Phe
<220> FEATURE:
<223> OTHER INFORMATION: see specification as filed for detailed
      description of substitutions and preferred embodiments

<400> SEQUENCE: 142

Xaa Xaa Xaa Xaa Xaa Xaa Xaa Xaa
1               5

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly or Ala
<220> FEATURE:
<221> NAME/KEY: MOD_RES
<222> LOCATION: (2)..(2)
<223> OTHER INFORMATION: Tyr, Phe or Trp
<220> FEATURE:
<221> NAME/KEY: MOD_RES
<222> LOCATION: (3)..(3)
<223> OTHER INFORMATION: Thr, Ser, Cys or Met
<220> FEATURE:
<221> NAME/KEY: MOD_RES
<222> LOCATION: (4)..(4)
<223> OTHER INFORMATION: Phe, Tyr or Trp
<220> FEATURE:
<221> NAME/KEY: MOD_RES
<222> LOCATION: (5)..(5)
<223> OTHER INFORMATION: Thr, Ser or Cys
<220> FEATURE:
<221> NAME/KEY: MOD_RES
<222> LOCATION: (6)..(6)
<223> OTHER INFORMATION: Ser, Thr or Cys
<220> FEATURE:
<221> NAME/KEY: MOD_RES
<222> LOCATION: (7)..(7)
<223> OTHER INFORMATION: Tyr, Phe or Trp
<220> FEATURE:
<223> OTHER INFORMATION: see specification as filed for detailed
      description of substitutions and preferred embodiments

<400> SEQUENCE: 143

Xaa Xaa Xaa Xaa Xaa Xaa Xaa Trp
1               5

<210> SEQ ID NO 144
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Ile, Leu, Val, Met or Ala
<220> FEATURE:
<221> NAME/KEY: MOD_RES
<222> LOCATION: (2)..(2)
<223> OTHER INFORMATION: Tyr, Phe, His, Arg, Lys, Ser or Thr
<220> FEATURE:
<221> NAME/KEY: MOD_RES
<222> LOCATION: (3)..(3)
<223> OTHER INFORMATION: Pro, Ser, Thr, Tyr, Phe, Arg, Lys or His
<220> FEATURE:
<221> NAME/KEY: MOD_RES
<222> LOCATION: (4)..(4)
<223> OTHER INFORMATION: Gly, Ala, Ser, Thr, Lys, Arg, His, Asp or Glu
<220> FEATURE:
<221> NAME/KEY: MOD_RES
<222> LOCATION: (5)..(5)
<223> OTHER INFORMATION: Thr, Ser or absent
<220> FEATURE:
<221> NAME/KEY: MOD_RES
<222> LOCATION: (6)..(6)
<223> OTHER INFORMATION: Arg, Lys, His or absent
<220> FEATURE:
<221> NAME/KEY: MOD_RES
<222> LOCATION: (7)..(7)
<223> OTHER INFORMATION: Asn, Gln, Asp, Glu, Gly, Ala or absent
<220> FEATURE:
<221> NAME/KEY: MOD_RES
<222> LOCATION: (8)..(8)
<223> OTHER INFORMATION: Gly, Ala, Ser, Thr, Tyr or Phe
<220> FEATURE:
<221> NAME/KEY: MOD_RES
<222> LOCATION: (9)..(9)
<223> OTHER INFORMATION: Asp, Glu, Ala, Gly, Asn or Gln
<220> FEATURE:
<221> NAME/KEY: MOD_RES
<222> LOCATION: (10)..(10)
<223> OTHER INFORMATION: Thr, Ser, Ile, Leu, Val, Met, Ala, Lys, Arg or
      His
<220> FEATURE:
<223> OTHER INFORMATION: see specification as filed for detailed
      description of substitutions and preferred embodiments

<400> SEQUENCE: 144

Xaa Xaa Xaa Xaa Xaa Xaa Xaa Xaa Xaa Xaa
1               5                   10

<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ile, Leu, Val, Met or Ala
<220> FEATURE:
<221> NAME/KEY: MOD_RES
<222> LOCATION: (2)..(2)
<223> OTHER INFORMATION: Tyr, Phe, His, Arg, Lys, Ser or Thr
<220> FEATURE:
<221> NAME/KEY: MOD_RES
<222> LOCATION: (3)..(3)
<223> OTHER INFORMATION: Pro, Ser, Thr, Tyr or Phe
<220> FEATURE:
<221> NAME/KEY: MOD_RES
<222> LOCATION: (4)..(4)
<223> OTHER INFORMATION: Gly, Ala, Ser, Thr, Lys, Arg or His
<220> FEATURE:
<221> NAME/KEY: MOD_RES
<222> LOCATION: (5)..(5)
<223> OTHER INFORMATION: Thr, Ser or absent
<220> FEATURE:
```

```
<221> NAME/KEY: MOD_RES
<222> LOCATION: (6)..(6)
<223> OTHER INFORMATION: Arg, Lys, His or absent
<220> FEATURE:
<221> NAME/KEY: MOD_RES
<222> LOCATION: (7)..(7)
<223> OTHER INFORMATION: Asn, Gln, Asp, Glu or absent
<220> FEATURE:
<221> NAME/KEY: MOD_RES
<222> LOCATION: (8)..(8)
<223> OTHER INFORMATION: Gly, Ala, Ser, Thr, Tyr or Phe
<220> FEATURE:
<221> NAME/KEY: MOD_RES
<222> LOCATION: (9)..(9)
<223> OTHER INFORMATION: Asp, Glu, Ala, Gly, Asn or Gln
<220> FEATURE:
<221> NAME/KEY: MOD_RES
<222> LOCATION: (10)..(10)
<223> OTHER INFORMATION: Thr, Ser, Ile, Leu, Val, Met or Ala
<220> FEATURE:
<223> OTHER INFORMATION: see specification as filed for detailed
      description of substitutions and preferred embodiments

<400> SEQUENCE: 145

Xaa Xaa Xaa Xaa Xaa Xaa Xaa Xaa Xaa Xaa
1               5                   10

<210> SEQ ID NO 146
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala, Gly, Val, Leu, Ile or Met
<220> FEATURE:
<221> NAME/KEY: MOD_RES
<222> LOCATION: (2)..(2)
<223> OTHER INFORMATION: Arg, Lys, His, Cys or Met
<220> FEATURE:
<221> NAME/KEY: MOD_RES
<222> LOCATION: (3)..(3)
<223> OTHER INFORMATION: Gly, Ala, Arg, Lys, His, Ser, Thr, Tyr, Phe,
      Trp, Asp, Glu or absent
<220> FEATURE:
<221> NAME/KEY: MOD_RES
<222> LOCATION: (4)..(4)
<223> OTHER INFORMATION: Tyr, Phe, Trp, Asn, Gln, Gly, Ala, Arg, Lys,
      His or absent
<220> FEATURE:
<221> NAME/KEY: MOD_RES
<222> LOCATION: (5)..(5)
<223> OTHER INFORMATION: Ser, Thr, Asn, Gln, Glu, Asp or absent
<220> FEATURE:
<221> NAME/KEY: MOD_RES
<222> LOCATION: (6)..(6)
<223> OTHER INFORMATION: Asp, Glu or absent
<220> FEATURE:
<221> NAME/KEY: MOD_RES
<222> LOCATION: (7)..(7)
<223> OTHER INFORMATION: Leu, Ile, Val, Met, Ala, Ser, Thr or absent
<220> FEATURE:
<221> NAME/KEY: MOD_RES
<222> LOCATION: (8)..(8)
<223> OTHER INFORMATION: Leu, Ile, Val, Met, Ala or absent
<220> FEATURE:
<221> NAME/KEY: MOD_RES
<222> LOCATION: (9)..(9)
<223> OTHER INFORMATION: Gly, Ala, Arg, Lys, His or absent
<220> FEATURE:
<221> NAME/KEY: MOD_RES
<222> LOCATION: (10)..(10)
<223> OTHER INFORMATION: Ile, Leu, Val, Met, Ala, Asn, Gln, Arg, Lys,
      His or absent
```

```
<220> FEATURE:
<221> NAME/KEY: MOD_RES
<222> LOCATION: (11)..(11)
<223> OTHER INFORMATION: Ala, Met, Phe, Tyr, Trp, Ser, Thr, Gly or
      absent
<220> FEATURE:
<221> NAME/KEY: MOD_RES
<222> LOCATION: (12)..(12)
<223> OTHER INFORMATION: Trp, Tyr, Phe, Ala, Gly or absent
<220> FEATURE:
<221> NAME/KEY: MOD_RES
<222> LOCATION: (13)..(13)
<223> OTHER INFORMATION: Phe, Tyr, Trp, Gly, Ala, Met or Cys
<220> FEATURE:
<221> NAME/KEY: MOD_RES
<222> LOCATION: (14)..(14)
<223> OTHER INFORMATION: Ala, Gly, Met, Asp, Glu, Trp, Tyr or Phe
<220> FEATURE:
<221> NAME/KEY: MOD_RES
<222> LOCATION: (15)..(15)
<223> OTHER INFORMATION: Tyr, Phe, Trp, Gly, Ala or Val
<220> FEATURE:
<223> OTHER INFORMATION: see specification as filed for detailed
      description of substitutions and preferred embodiments

<400> SEQUENCE: 146

Xaa Xaa Xaa Xaa Xaa Xaa Xaa Xaa Xaa Xaa Xaa Xaa Xaa Xaa Xaa
1               5                   10                  15

<210> SEQ ID NO 147
<211> LENGTH: 7
<212> TYPE: PRT
<213> ORGANISM: Unknown
<220> FEATURE:
<223> OTHER INFORMATION: Description of Unknown: Human or Mouse VASA
      peptide peptide

<400> SEQUENCE: 147

Pro Asn Pro Val Asp Asp Glu
1               5

<210> SEQ ID NO 148
<211> LENGTH: 4
<212> TYPE: PRT
<213> ORGANISM: Unknown
<220> FEATURE:
<223> OTHER INFORMATION: Description of Unknown: 'DEAD' family motif
      peptide

<400> SEQUENCE: 148

Asp Glu Ala Asp
1
```